US012233137B1

(12) United States Patent
Pomper et al.

(10) Patent No.: US 12,233,137 B1
(45) Date of Patent: Feb. 25, 2025

(54) PSMA TARGETED RADIOHALOGENATED UREA-POLYAMINOCARBOXYLATES FOR CANCER RADIOTHERAPY

(71) Applicants: The Johns Hopkins University, Baltimore, MD (US); Duke University, Durham, NC (US)

(72) Inventors: Martin G. Pomper, Baltimore, MD (US); Ronnie C. Mease, Fairfax, VA (US); Vivek Kumar, Rensselaer, NY (US); Sangeeta Ray, Ellicott City, MD (US); Michael Zalutsky, Chapel Hill, NC (US); Ganesan Vaidyanathan, Chapel Hill, NC (US)

(73) Assignees: The Johns Hopkins University, Baltimore, MD (US); Duke University, Durham, NC (US)

( * ) Notice: Subject to any disclaimer, the term of this patent is extended or adjusted under 35 U.S.C. 154(b) by 0 days.

(21) Appl. No.: 18/448,682

(22) Filed: Aug. 11, 2023

Related U.S. Application Data

(63) Continuation of application No. 16/967,488, filed as application No. PCT/US2019/016821 on Feb. 6, 2019, now Pat. No. 11,813,340.

(60) Provisional application No. 62/626,993, filed on Feb. 6, 2018.

(51) Int. Cl.
A61K 51/04 (2006.01)
A61K 47/18 (2017.01)
A61P 35/00 (2006.01)
C07B 39/00 (2006.01)
C07B 59/00 (2006.01)

(52) U.S. Cl.
CPC .......... *A61K 51/0482* (2013.01); *A61K 47/18* (2013.01); *A61P 35/00* (2018.01); *C07B 39/00* (2013.01); *C07B 59/004* (2013.01); *A61K 2121/00* (2013.01); *C12Y 304/17021* (2013.01)

(58) Field of Classification Search
CPC .............................. A61K 51/04; A61P 35/00
See application file for complete search history.

(56) References Cited

U.S. PATENT DOCUMENTS

| | | | |
|---|---|---|---|
| 7,408,079 B2 | 8/2008 | Pomper et al. | |
| 8,211,401 B2* | 7/2012 | Babich | A61P 25/18 |
| | | | 424/1.65 |
| 2004/0054190 A1 | 3/2004 | Pomper et al. | |
| 2008/0193381 A1 | 8/2008 | Babich et al. | |
| 2013/0034494 A1 | 2/2013 | Babich et al. | |
| 2016/0228587 A1 | 8/2016 | Eder et al. | |

FOREIGN PATENT DOCUMENTS

| | | | |
|---|---|---|---|
| WO | WO 03/060523 | 7/2003 | |
| WO | WO 2009/002529 | 12/2008 | |
| WO | WO 2009/026177 | 2/2009 | |
| WO | WO 2010/014933 | 2/2010 | |
| WO | WO 2010/045598 | 4/2010 | |
| WO | WO 2010/108125 | 9/2010 | |
| WO | WO 2011/106639 | 9/2011 | |
| WO | WO 2013/082338 | 6/2013 | |
| WO | WO-2013082338 A1 * | 6/2013 | ............ A61K 38/06 |
| WO | WO 2015/171792 | 11/2015 | |
| WO | WO 2017/070482 | 4/2017 | |
| WO | WO 2017/165473 | 9/2017 | |
| WO | WO 2018/222778 | 12/2018 | |
| WO | WO 2020/028323 | 2/2020 | |

OTHER PUBLICATIONS

Extended European Search Report for PCT/US2019/016821. Mailed Nov. 15, 2021. 17 pages.
International Search Report and Written Opinion for PCT/US2019/016821. Mailed May 23, 2019. 16 pages.
Berge et al., Pharmaceutical Salts. J Pharm Sci. Jan. 1977;66(1):1-19.
Eder et al., 68Ga-complex lipophilicity and the targeting property of a urea-based PSMA inhibitor for PET imaging. Bioconjug Chem. Apr. 18, 2012;23(4):688-97.
Greene et al., Protective Groups in Organic Synthesis, 3rd ed. John Wiley & Sons. 1999. TOC only. 3 pages.
Kiess et al., (2S)-2-(3-(1-Carboxy-5-(4-211At-Astatobenzamido)Pentyl)Ureido)-Pentanedioic Acid for PSMA-Targeted α-Particle Radiopharmaceutical Therapy. J Nucl Med. Oct. 2016;57(10):1569-1575.
Mease et al., Small Molecule Radiohalogenated (125I/211At), DOTA Containing PSMA Inhibitors: Metal Complexation and Competing Inhibitor Improve Biodistribution in Mice. Journal of Nuclear Medicine. 2018;59:537.
Rahbar et al., PSMA Theranostics: Current Status and Future Directions. Mol Imaging. Jan.-Dec. 2018;17:1536012118776068. 9 pages.
Sessler et al., Photoinduced energy transfer in associated, but noncovalently-linked photosynthetic model systems. J. Am. Chem. Soc. 1995, 117, 704-714.
Tykvart et al., Rational design of urea-based glutamate carboxypeptidase II (GCPII) inhibitors as versatile tools for specific drug targeting and delivery. Bioorg Med Chem. Aug. 1, 2014;22(15):4099-108.

(Continued)

Primary Examiner — Michael G. Hartley
Assistant Examiner — Jagadishwar R Samala
(74) Attorney, Agent, or Firm — Casimir Jones, SC; Jeffrey W. Childers

(57) ABSTRACT

Small molecule radiohalogenated PSMA inhibitors and metal complexes thereof and their use in radioimaging and radiotherapy for treating PSMA-related diseases, including prostate cancer, are disclosed. The combination of small molecule radiohalogenated PSMA inhibitors with a competitive PSMA ligand for reducing off-target accumulation of the radiohalogenated PSMA inhibitor also is disclosed.

20 Claims, 6 Drawing Sheets

(56) References Cited

OTHER PUBLICATIONS

Vaidyanathan et al., SIB-DOTA: a trifunctional prosthetic group potentially amenable for multi-modal labeling that enhances tumor uptake of internalizing monoclonal antibodies. Bioorg Med Chem. Dec. 15, 2012;20(24):6929-39.

* cited by examiner

[125I]2

X = 125I or 211At

[125I/211At]3

PSMA TARGETED RADIOHALOGENATED UREA-POLYAMINOCARBOXYLATES FOR CANCER RADIOTHERAPY

BACKGROUND

Prostate cancer is the leading cancer in the U.S. population and the second leading cause of cancer death in men. Therapy for locally advanced disease remains contentious and an increasing number of disparate options are available. High-sensitivity, low molecular weight imaging agents for prostate cancer using the prostate-specific membrane antigen (PSMA) as a target are currently under development. PSMA is a marker for androgen-independent disease that also is expressed on solid (nonprostate) tumor neovasculature. PSMA-based imaging agents are known in the art, however, PSMA-based radiotherapy agents can exhibit undesirable off-target effects, such as renal toxicity and dry mouth.

SUMMARY

In some aspects, the presently disclosed subject matter provides a compound of formula (I):

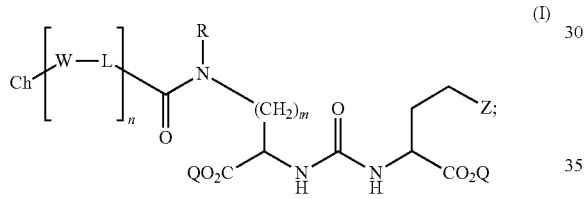

wherein: Z is tetrazole or $CO_2Q$; Q is H or a protecting group; m is an integer selected from the group consisting of 1, 2, 3, 4, and 5; R is independently H or —$CH_2$—$R^1$; wherein $R^1$ is:

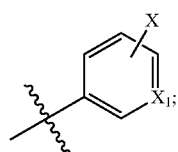

wherein $X_1$ is —$CR^3$, —C—X, or N, wherein $R^3$ is H or $C_1$-$C_4$ alkyl; wherein X is selected from the group consisting of a radioisotope of iodine, a radioisotope of bromine, and a radioisotope of astatine; or X is halogen when at least one L is a substituted arylene; L is a linker selected from the group consisting of $C_1$, $C_2$, $C_3$, $C_4$, $C_5$, and $C_6$ alkylene, $C_3$, $C_4$, $C_5$, and $C_6$ cycloalkylene, and arylene, each of which can be substituted to unsubstituted; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or $C_1$-$C_4$ alkyl; n is an integer selected from the group consisting of 1, 2, and 3; Ch is a chelating agent that can comprise a metal; and pharmaceutically acceptable salts thereof.

In particular aspects, X is selected from the group consisting of $^{125}I$, $^{123}I$, $^{131}I$, $^{124}I$, $^{211}At$, $^{77}Br$, and $^{80m}Br$. In yet more particular aspects, X is $^{125}I$ or $^{211}At$. In certain aspects, when at least one L is substituted arylene, X is halogen.

In even yet more particular aspects, the chelating agent is selected from the group consisting of:

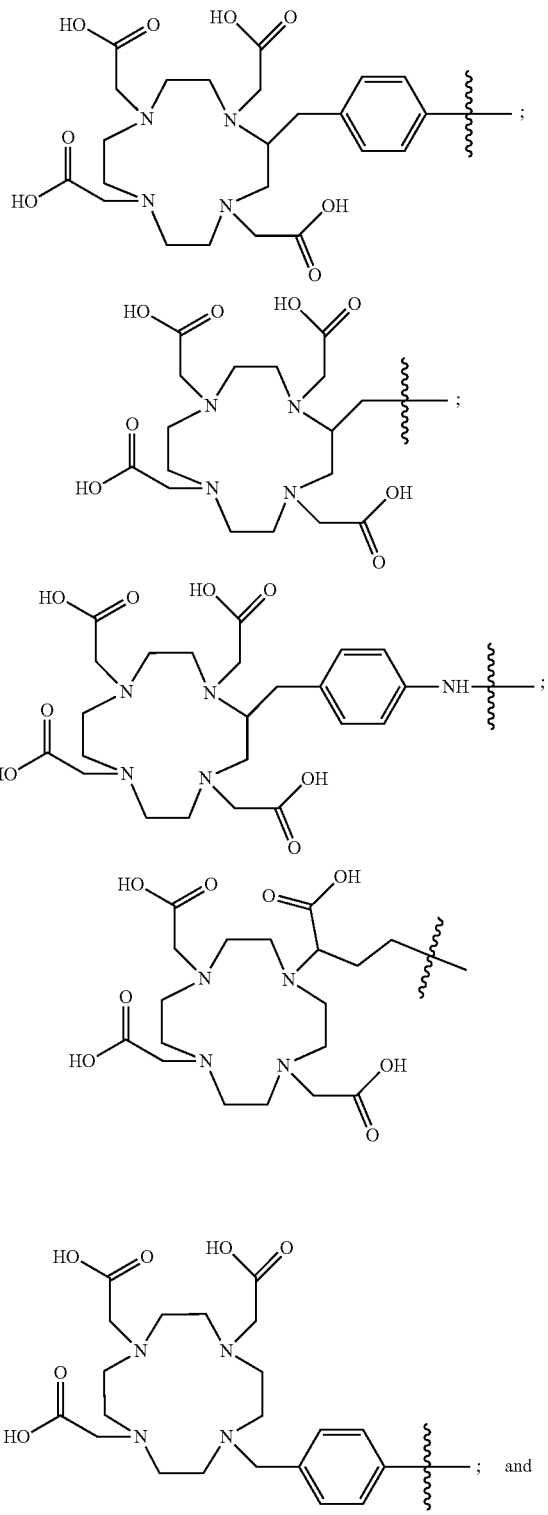

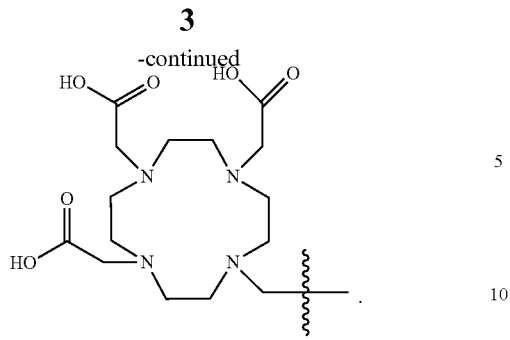

In certain aspects, the metal chelating agent comprises a metal selected from the group consisting of: Y, Lu, Tc, Zr, In, Sm, Re, Cu, Pb, Ac, Bi, Al, Ga, Re, Ho and Sc. In more certain aspects, the metal is $^{175}$Lu.

In particular aspects, the compound of formula (I) has the following formula:

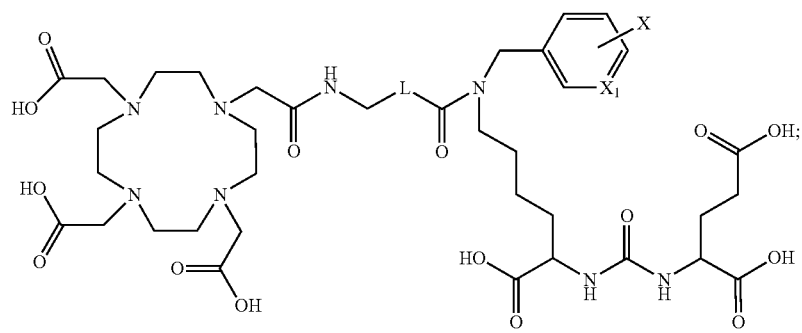

wherein L is selected from $C_1$, $C_2$, $C_3$, $C_4$, $C_5$, and $C_6$ alkylene; wherein $X_1$ is —$CR^3$, —C—X, or N, wherein $R^3$ is H or $C_1$-$C_4$ alkyl; and wherein X is selected from the group consisting of a radioisotope of iodine, a radioisotope of bromine, and a radioisotope of astatine.

In more particular aspects, the compound of claim 1, wherein the compound of formula (I) has the following formula:

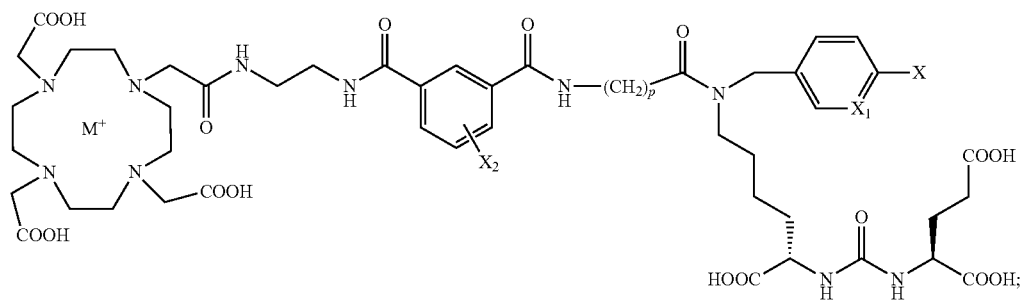

wherein: p is an integer selected from the group consisting of 1, 2, 3, 4, 5, and 6; and X is halogen; $X_1$ is —$CR^3$, —C—X, or N, wherein $R^3$ is H or $C_1$-$C_4$ alkyl; and $X_2$ is selected from the group consisting of a radioisotope of iodine, a radioisotope of bromine, and a radioisotope of astatine; and wherein $M^+$ is a metal, which can be present or absent. In certain aspects, $M^+$ is a metal selected from the group consisting of: Y, Lu, Tc, Zr, In, Sm, Re, Cu, Pb, Ac, Bi, Al, Ga, Re, Ho and Sc, and radioisotopes thereof.

In yet more particular aspects, the compound of formula (I) is selected from the group consisting of:

or cell, a germ cell, a pheochromocytoma, an esophageal tumor or cell, a stomach tumor or cell, and combinations thereof.

In particular aspects, the method further comprises administering a blocking agent in combination with the compound of formula (I), wherein the blocking agent reduces accumulation of the compound of formula (I) in one or more PSMA expressing cells in an off-target organ. In yet more particular aspects, the off-target organ is selected from the group consisting of blood, stomach, spleen, thyroid gland, salivary gland, lacrimal gland, and kidney.

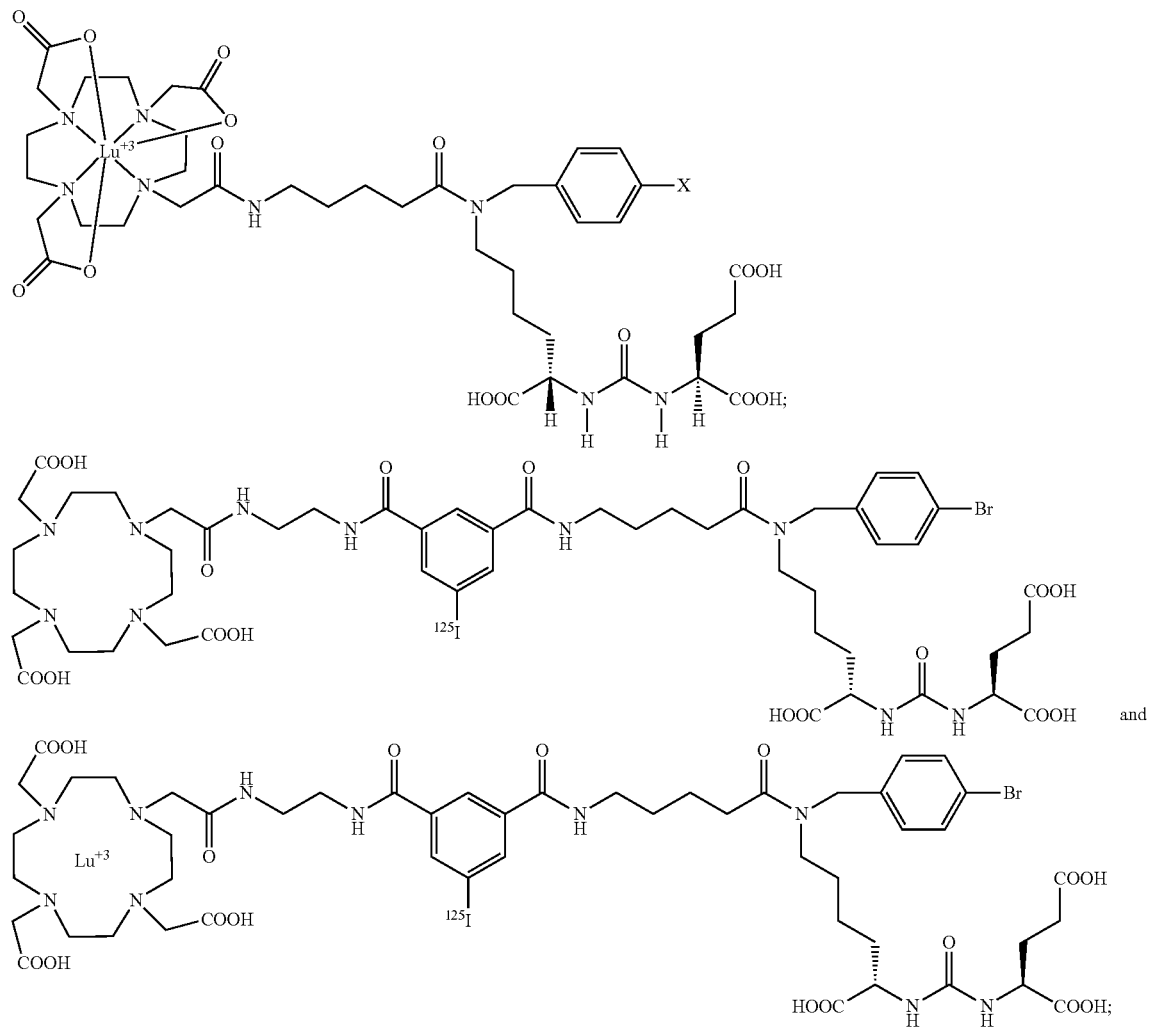

wherein X is $^{125}$I or $^{211}$At.

In other aspects, the presently disclosed subject matter provides a method for treating one or more PSMA expressing tumors or cells, the method comprising contacting the one or more PSMA expressing tumors or cells with an effective amount of a compound of formula (I).

In certain aspects, the one or more PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor In certain aspects, the blocking agent comprises a PSMA-based blocking agent. In more certain aspects, the PSMA-based blocking agent is a compound of formula (I) in which the compound is not radiohalogenated, wherein the compound of formula (I) used as a blocking agent and the compound of formula (I) used as a therapeutic agent can be the same or different.

In some aspects, the presently disclosed subject matter provides a method for imaging one or more prostate-specific membrane antigen (PSMA) tumors or cells, the method comprising contacting the one or more tumors or cells with an effective amount of a compound of formula (I) and making an image, wherein X of the compound of formula (I) is $^{124}$I and the imaging comprises positron emission tomography (PET).

In yet other aspects, the presently disclosed subject matter provides a one-pot, multi-step synthesis method for preparing a radiotherapeutic compound of formula (Ia):

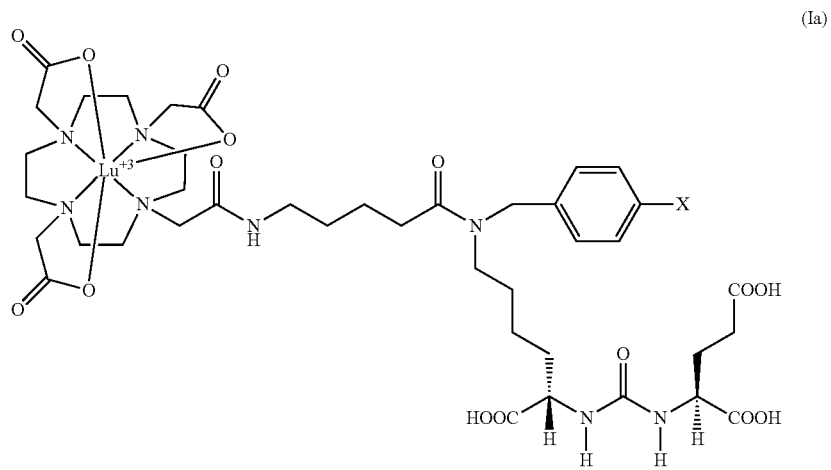

(Ia)

wherein X is a radiohalide, the method comprising:
(a) providing a precursor compound of formula (Ia'):

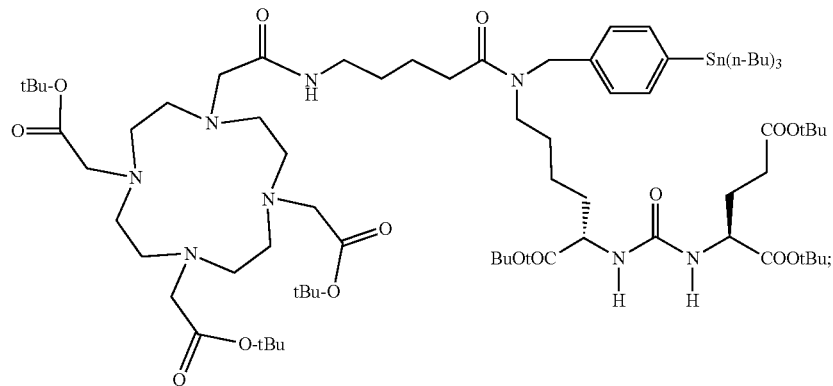

(b) contacting the precursor compound of formula (Ia') with solution comprising a radiohalide and N-chlorosuccinimide, followed by the addition of glacial acetic acid to form a radiohalogenated precursor compound of formula (Ia"):

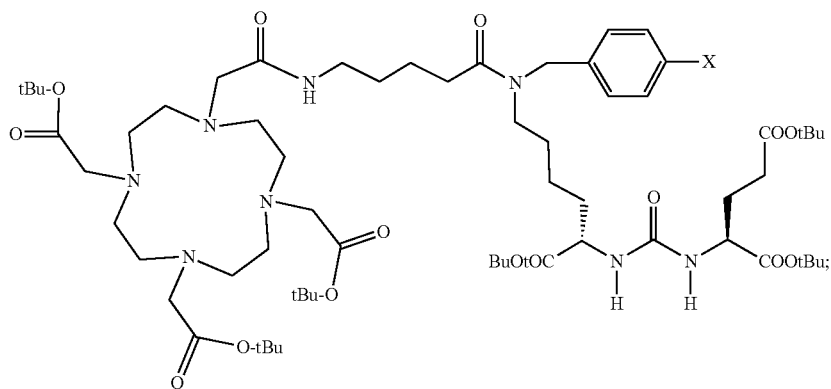

(c) contacting the radiohalogenated precursor compound of formula (Ia″) with trifluoroacetic acid to form a radiohalogenated compound of formula (Ia‴).

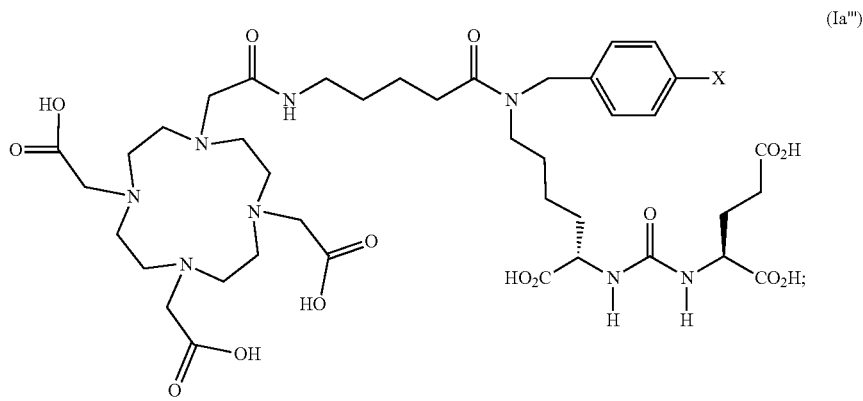

(d) contacting the radiohalogenated compound of formula (Ia‴) with NaOAc and Lu(NO$_3$)$_3$ to form a radiotherapeutic compound of formula (Ia).

In yet other aspects, the presently disclosed subject matter provides a pharmaceutical composition comprising a compound of formula (I) and a pharmaceutically acceptable carrier.

In even yet other aspects, the presently disclosed subject matter provides a kit for treating one or more PSMA expressing tumors or cells, the kit comprising a compound of formula (I). In particular aspects, the kit further comprises a blocking agent.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
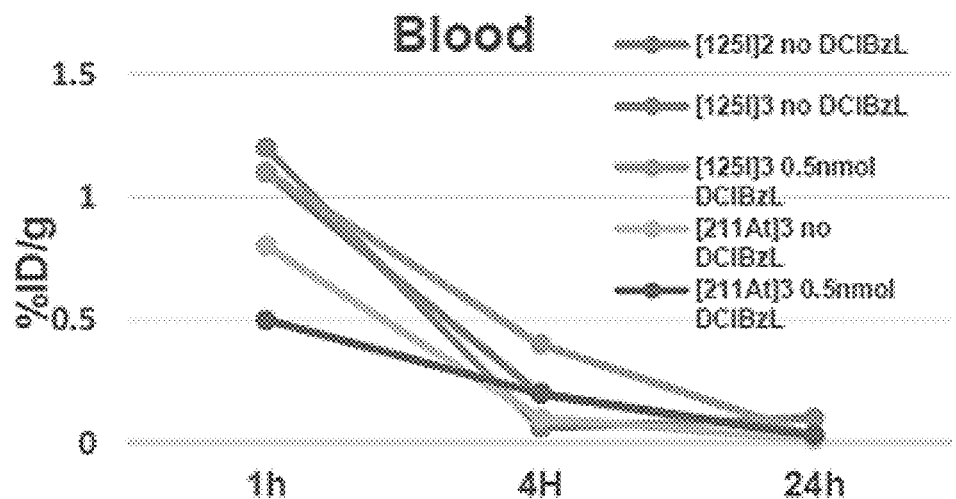
Figure 1B:
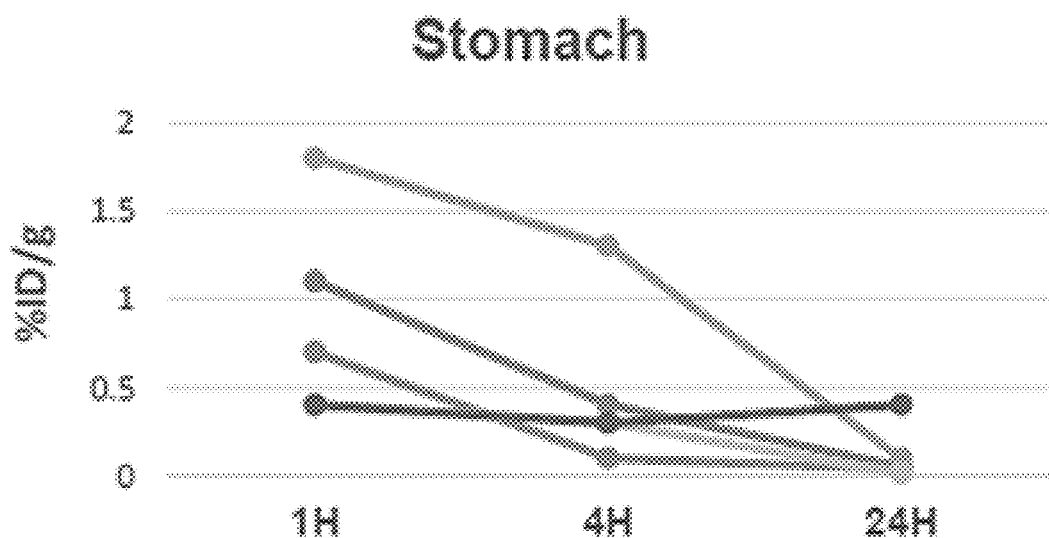
Figure 1C:
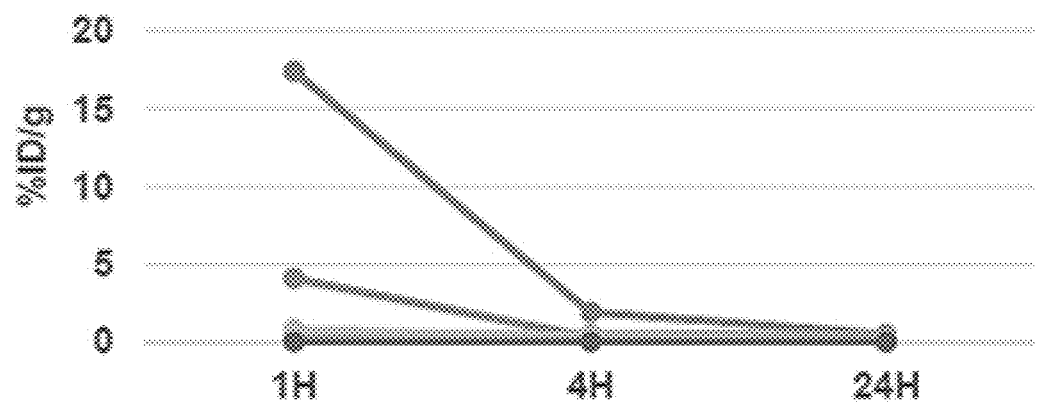
Figure 1D:
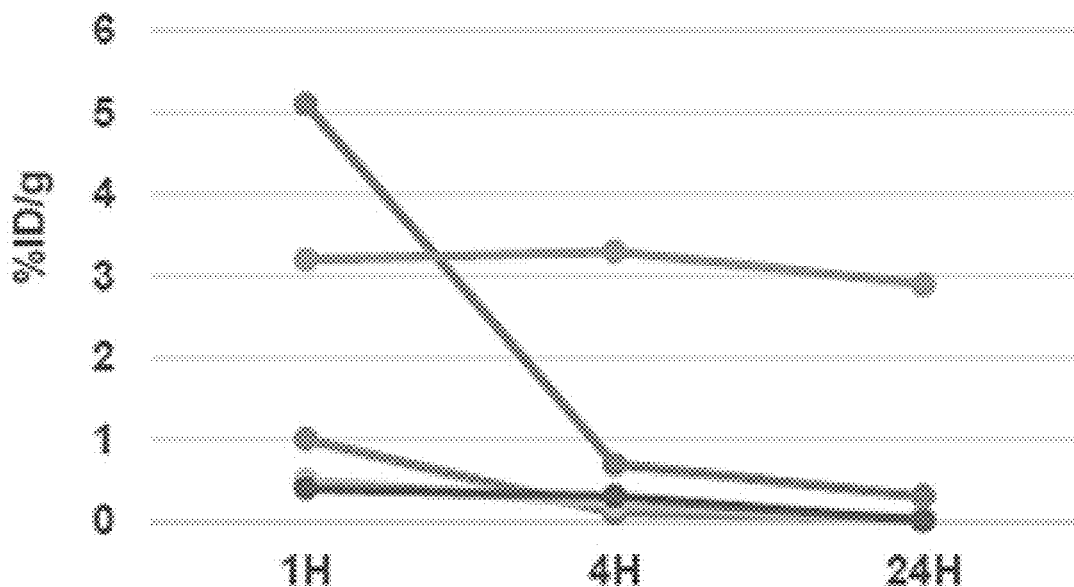
Figure 1E:
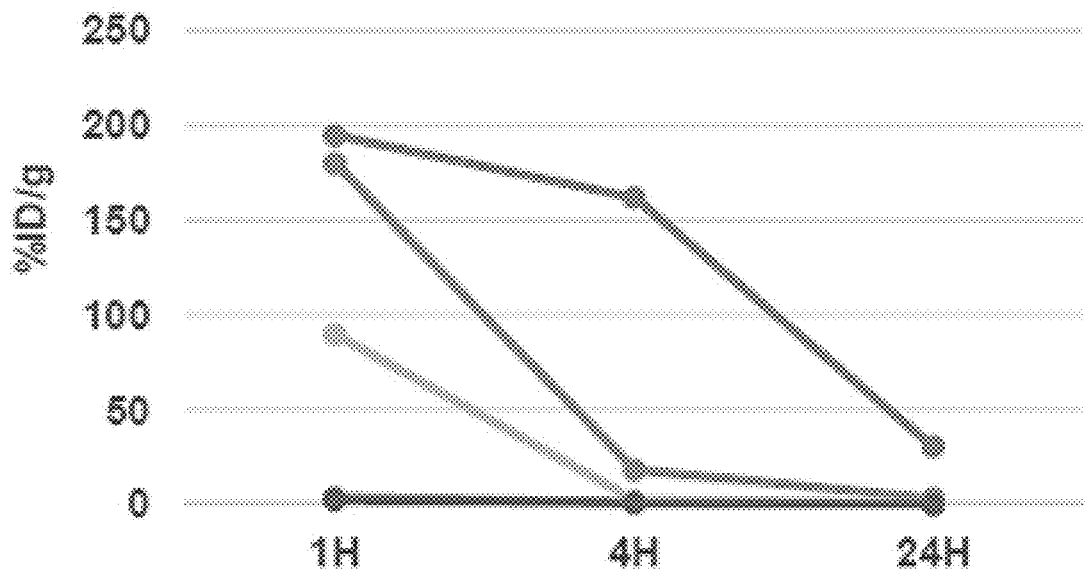
Figure 1F:
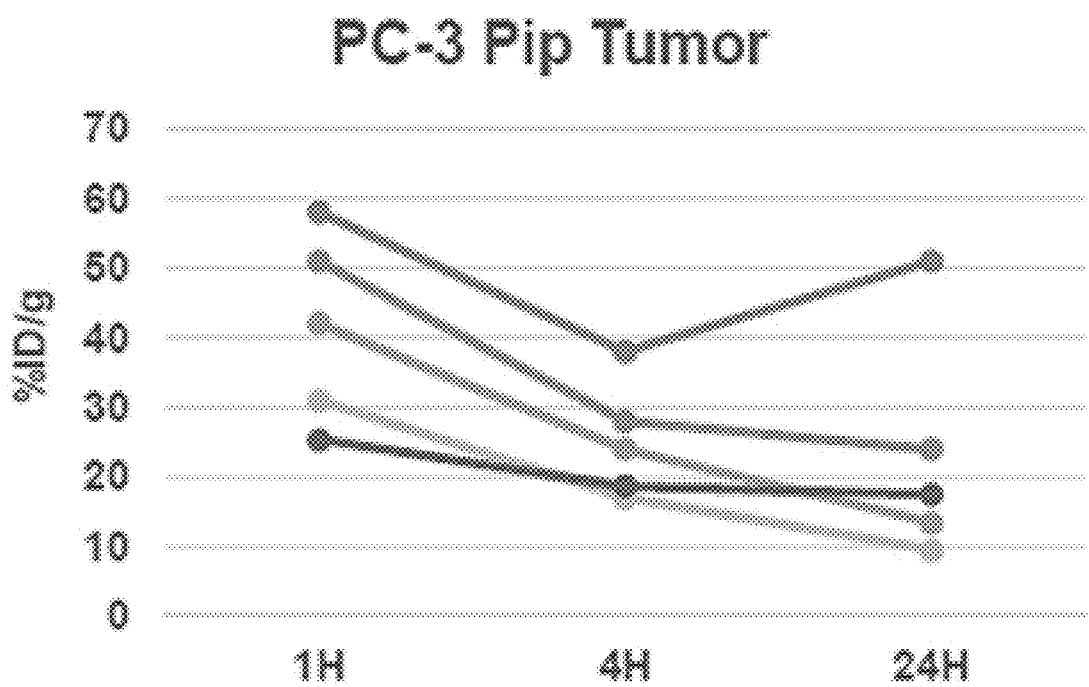
Figure 1G:
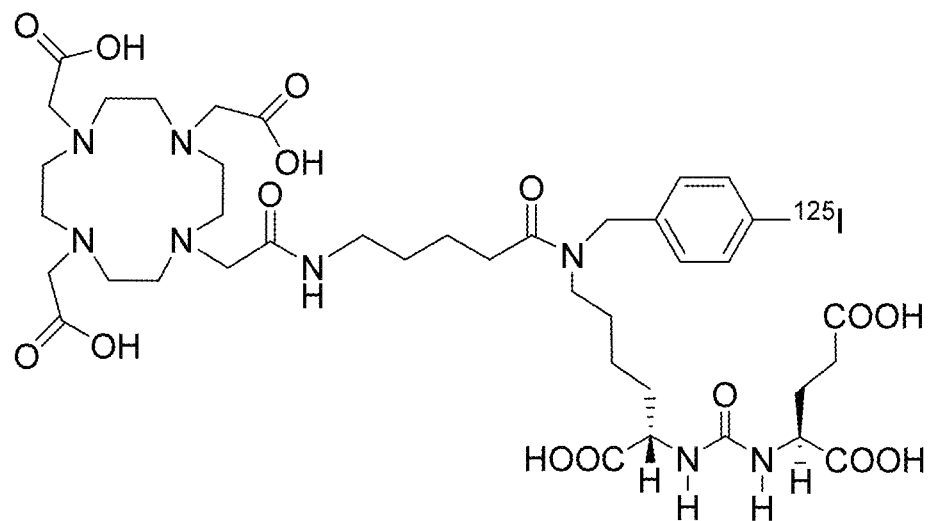
Figure 1H:
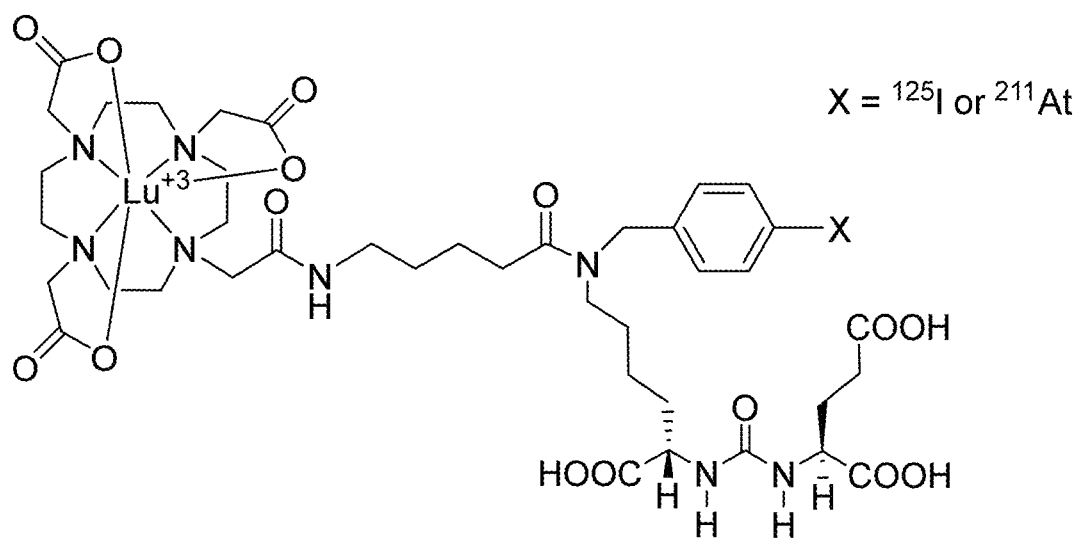
Figure 2:
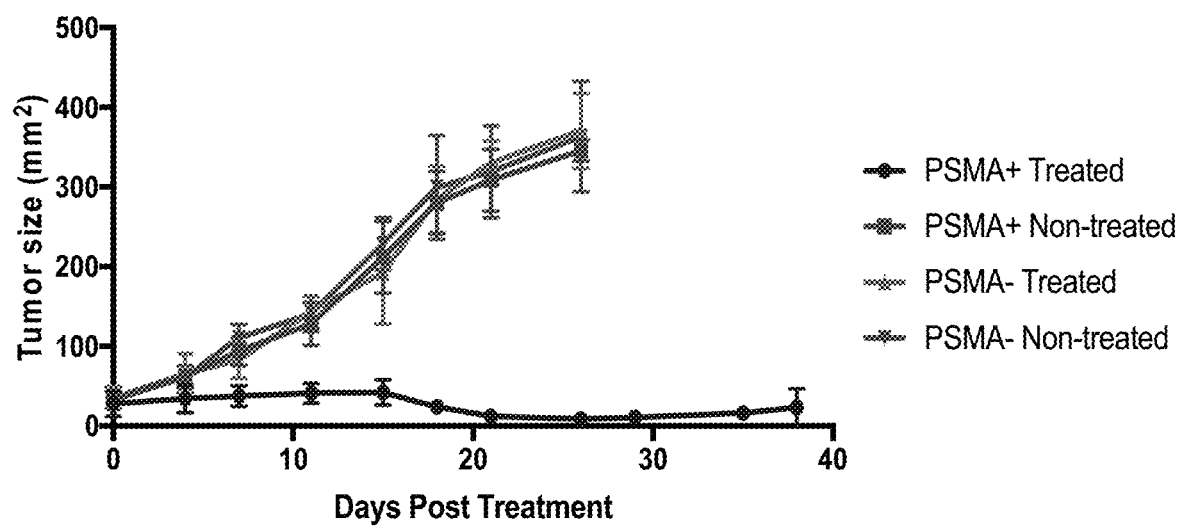
Figure 3A:
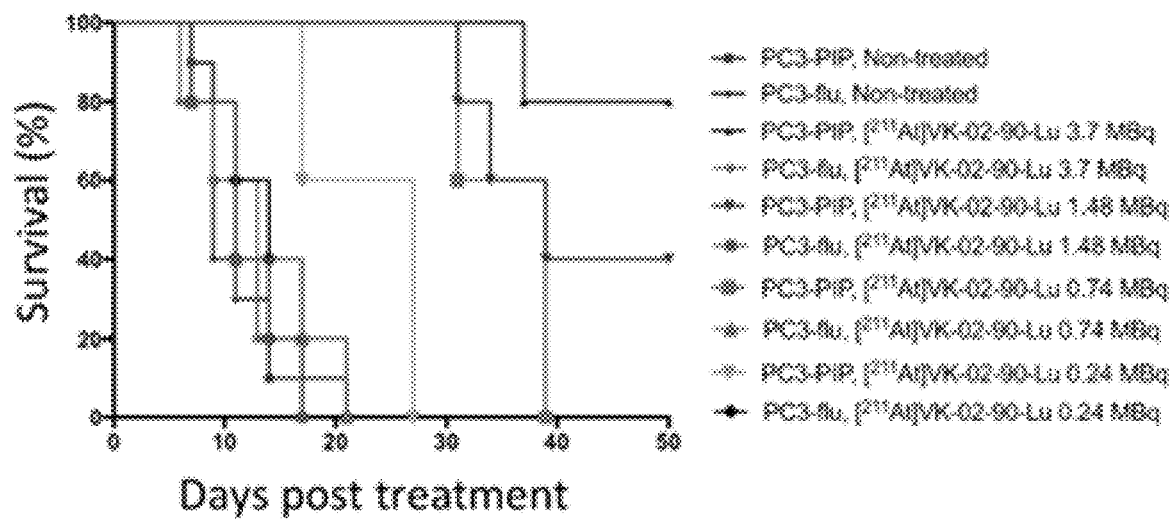
Figure 3B:
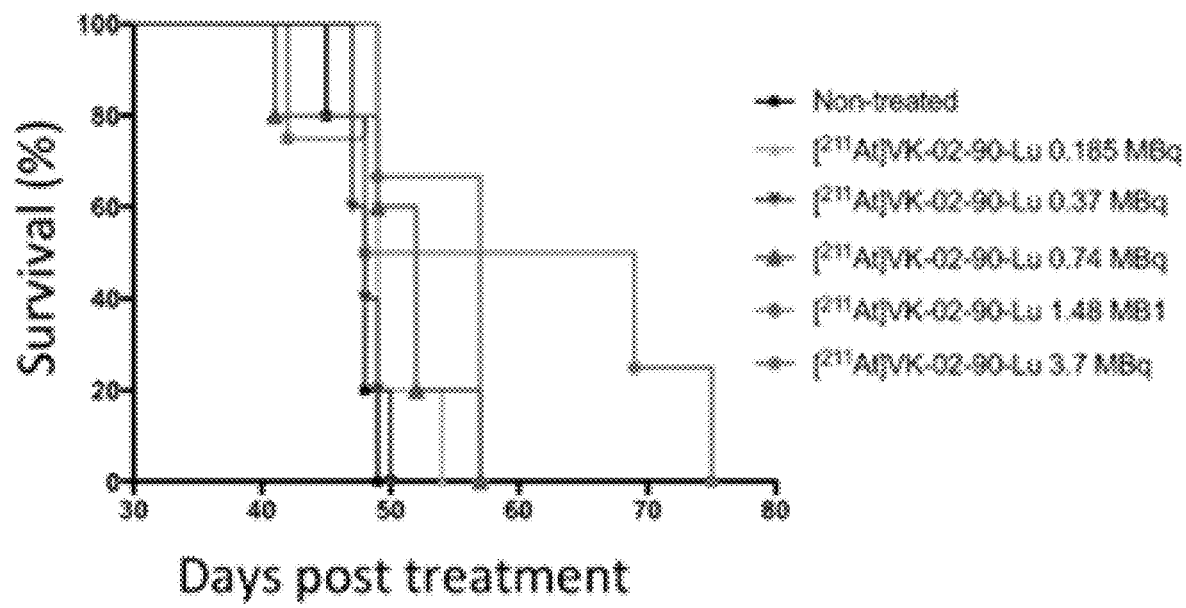

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, FIG. 1E, and FIG. 1F show the biodistribution (% ID/g) of [$^{125}$I]2 and [$^{125}$I/$^{211}$At]3 with and without blocker (DClBzL(YC-1-27));

FIG. 1G is a chemical structure of [$^{125}$I]2;

FIG. 1H is a chemical structure of [$^{125}$I/$^{211}$At]3;

FIG. 2 shows [$^{211}$At]VK0290-Lu Treatment (3.7 MBq, 100 uCi) in athymic mice bearing both PSMA+ (PiP) and PSMA− (flu) tumor xenografts. Five mice were treated; and FIG. 3A and FIG. 3B demonstrate that [$^{211}$At]VK-02-90-Lu exhibited dose-dependent efficacy. FIG. 3A is a SC model of PSMA+ PC3-PIP and PSMA− PC3-flu model. The tumor volume increase of more than 4-fold was scored as death of animals. FIG. 3B is a metastatic model of PSMA+ PC3ML/PSMA/fLuc.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

I. PSMA Targeted Radiohalogenated Ureas for Cancer Radiotherapy

A variety of high affinity radiohalogenated, urea-based PSMA inhibitors that selectively image prostate tumors in experimental models have been developed. Because of the favorable pharmacokinetic profile of this class of compounds, i.e., low nonspecific binding, lack of metabolism in vivo and reasonable tumor residence times, it was thought that the strategy adopted for molecular imaging could be extended to molecular radiotherapy. This approach is analogous to that of radioimmunotherapy (RIT), which has proved remarkably successful in the treatment of lymphoma with two commercial products routinely integrated into clinical practice. RIT, however, is fraught with similar difficulties to the use of radiolabeled antibodies for imaging, including prolonged circulation times, unpredictable biological effects, and the occasional need for pre-targeting strategies. Furthermore, antibodies may have less access to tumors than low molecular weight agents, which can be manipulated pharmacologically.

The development of low molecular weight radiotherapeutic agents, however, is much different than developing radiopharmaceuticals for imaging in that longer tumor residence times, as well as shorter non-target organ residence times, are desired for radiotherapeutic agents. Radiotherapeutic halogens include Auger electron emitting radionuclides $^{125}$I, $^{123}$I and $^{80m}$Br, beta-particle emitters $^{131}$I, and $^{77}$Br, and alpha-particle emitter $^{211}$At. I-124 is a positron emitter and I-124 labeled agents would permit PET imaging and individual dosimetry in patients prior to radiotherapy with the corresponding agent labeled with the radiotherapeutic nuclide. Astatine-211 has attractive properties for radiopharmaceutical therapy, including a 7.2-hr half-life and 100% α-particle emission per decay. Astatine-211 also lacks α-particle emitting daughters that can escape from the targeting molecule, which can lead to excessive radiation dose to normal organs. Initial experiments in mice using I-125/I-131/and At-211 labeled ureas demonstrated high specific PSMA positive tumor uptake, but suffered from slow renal clearance, which can lead to renal toxicity. International PCT Patent Application Publication No. WO2017070482 A2, to Pomper et al., published Apr. 27, 2017, which is incorporated herein by reference in its entirety. In addition, At-211 labeled ureas had significant accumulation in the stomach, which is symptomatic of free At-211.

Radiometal complexed DOTA-urea conjugates also demonstrate high specific PSMA positive tumor uptake, but exhibit rapid renal excretion. See International PCT Patent Application Publication No. WO2017165473 A1, to Pomper et al., published Sep. 28, 2017, which is incorporated herein by reference in its entirety. The presently disclosed subject matter provides the preparation and biodistribution in mice of radioiodinated and radioastatinated DOTA-urea conjugates with and without complexed non-radioactive metal ion.

Accordingly, in some embodiments, the presently disclosed subject matter provides radiolabeling of a DOTA-urea with radioiodine and/or At-211 using a novel tributyltin precursor followed by complexation of nonradioactive lutetium. The radiochemistry has been reduced to a multi-step one pot synthesis with only a single HPLC purification of the final product. The entire process is simple enough for automation for routine production. The chemical reactivity of At-211 decreases with time, presumably due to a change in chemical state from radiolysis. The radiolabeling with At-211, which has been allowed to stand 18 hours to simulate the transport of radionuclide from site of production to site of radiotracer synthesis also was successful, such that the presently disclosed chemistry is feasible using At-211 produced at a remote site.

A. Compounds of Formula (I)

In some embodiments, the presently disclosed subject matter provides a compound of formula (I):

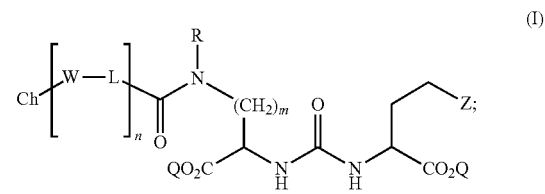

wherein: Z is tetrazole or $CO_2Q$; Q is H or a protecting group; m is an integer selected from the group consisting of 1, 2, 3, 4, and 5; R is independently H or $-CH_2-R^1$; wherein $R^1$ is:

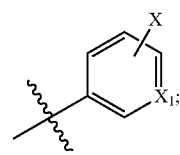

wherein $X_1$ is $-CR^3$, $-C=X$, or N, wherein $R^3$ is H or $C_1$-$C_4$ alkyl; wherein X is selected from the group consisting of a radioisotope of iodine, a radioisotope of bromine, and a radioisotope of astatine; or X is halogen when at least one L is a substituted arylene; L is a linker selected from the group consisting of $C_1$, $C_2$, $C_3$, $C_4$, $C_5$, and $C_6$ alkylene, $C_3$, $C_4$, $C_5$, and $C_6$ cycloalkylene, and arylene, each of which can be substituted to unsubstituted; W is selected from the group consisting of $-NR^2-(C=O)-$, $-NR^2-(C=S)-$, $-(C=O)-NR^2-$, and $-(C=S)-NR^2-$; wherein each occurrence of L and W can be the same or different; $R^2$ is H or $C_1$-$C_4$ alkyl; n is an integer selected from the group consisting of 1, 2, and 3; Ch is a chelating agent that can comprise a metal; and pharmaceutically acceptable salts thereof.

In particular embodiments, $R^1$ is selected from the group consisting of:

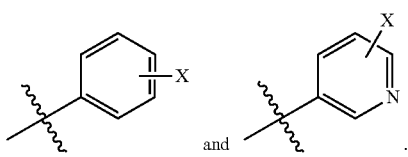

and.

In yet more particular embodiments, X is selected from the group consisting of $^{125}I$, $^{124}I$, $^{123}I$, $^{131}I$, $^{211}At$, $^{77}Br$, and $^{80m}Br$. In certain embodiments, at least one L is substituted arylene and X is halogen.

In even yet more particular embodiments, the chelating agent is selected from the group consisting of:

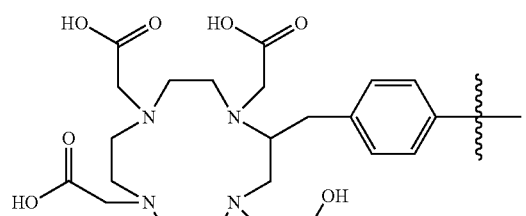

;

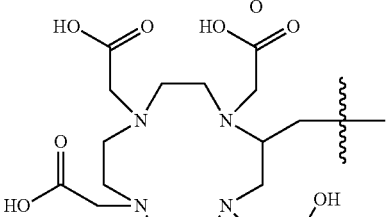

;

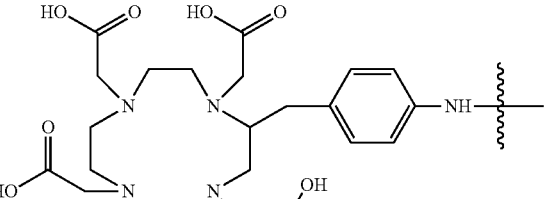

;

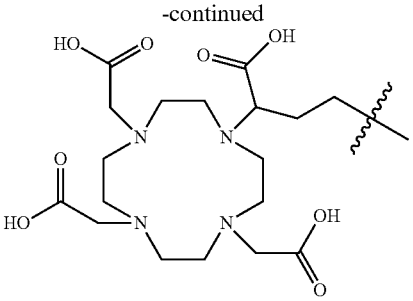

;

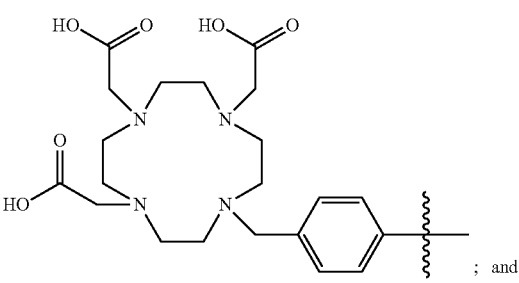

; and

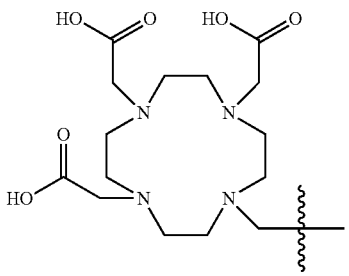

.

In certain embodiments, the metal chelating agent comprises a metal selected from the group consisting of Y, Lu, Tc, Zr, In, Sm, Re, Cu, Pb, Ac, Bi, Al, Ga, Re, Ho and Sc, and radioisotopes thereof. In more certain embodiments, the metal is $^{175}$Lu.

In particular embodiments, the compound of formula (I) is selected from the group consisting of:

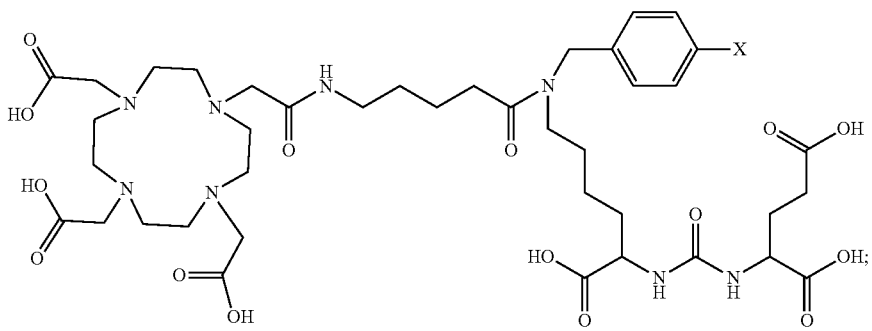

-continued
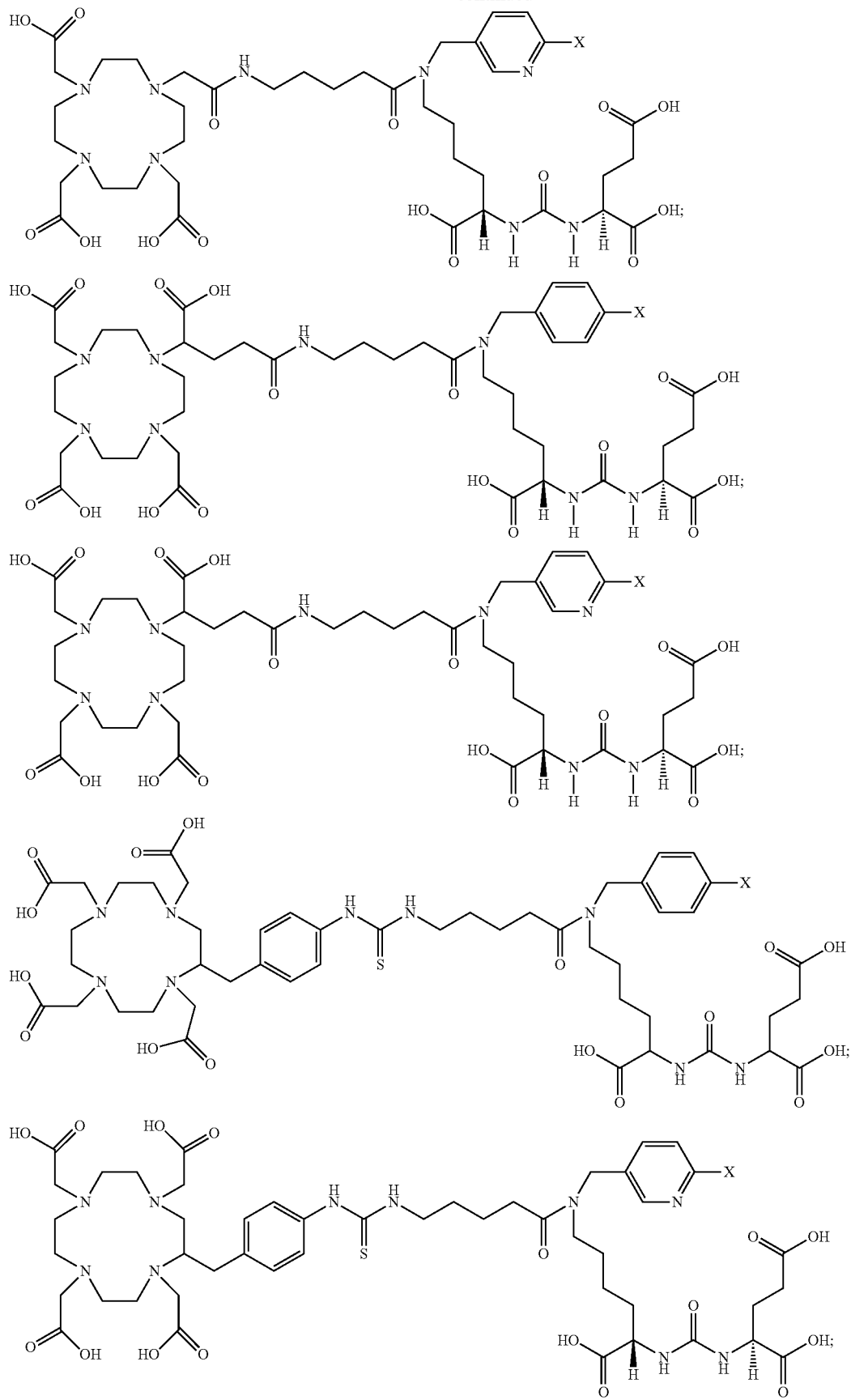

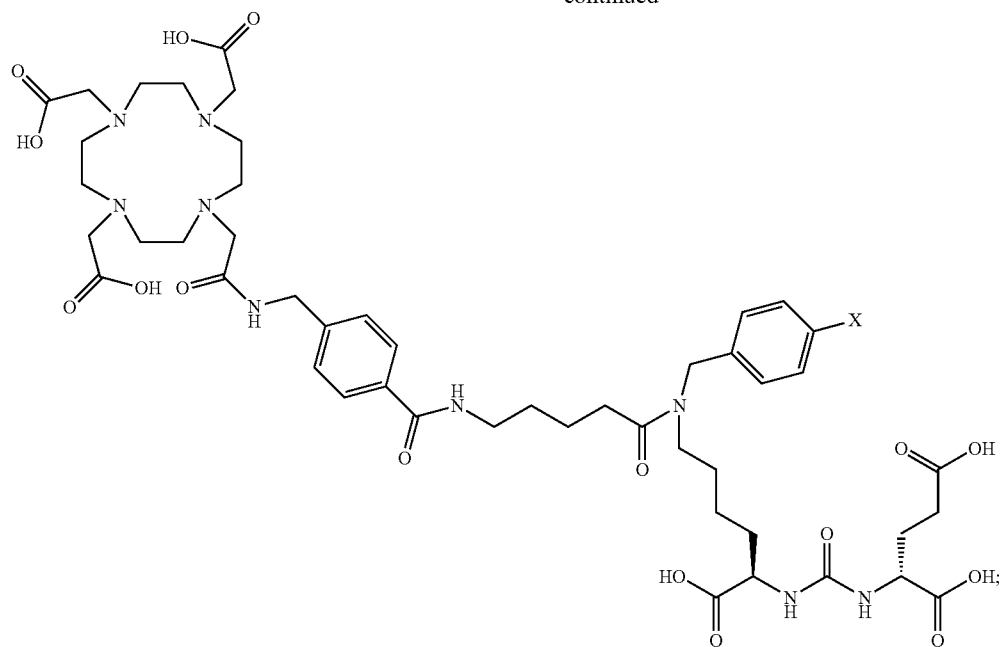
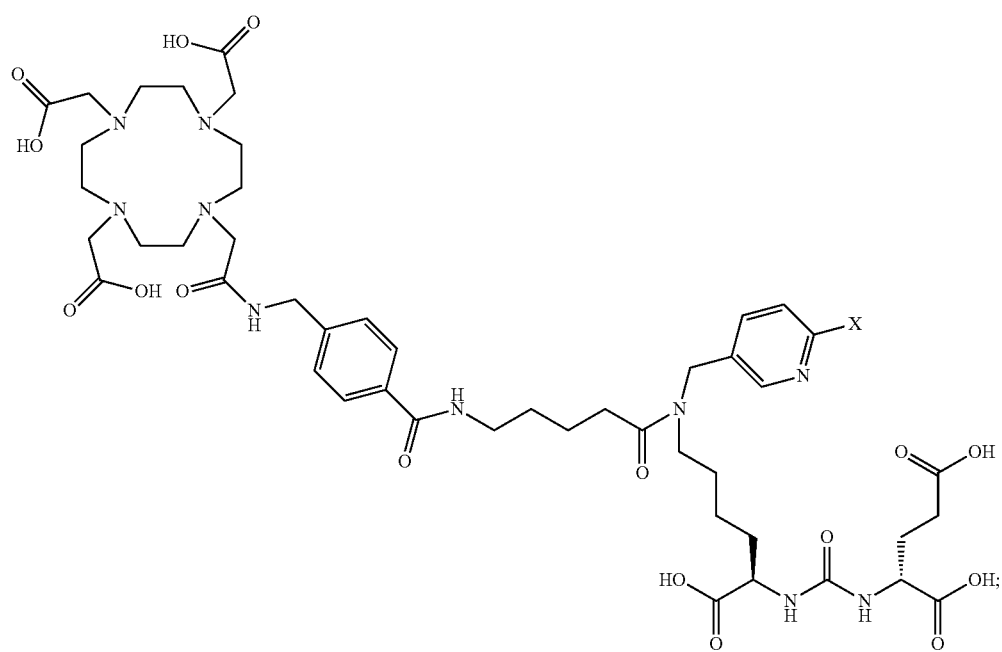

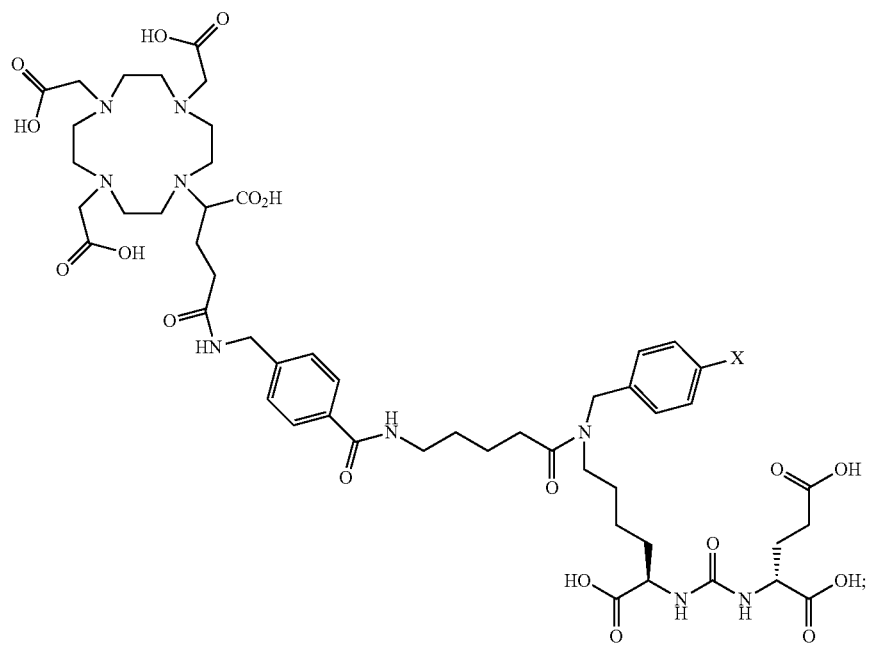
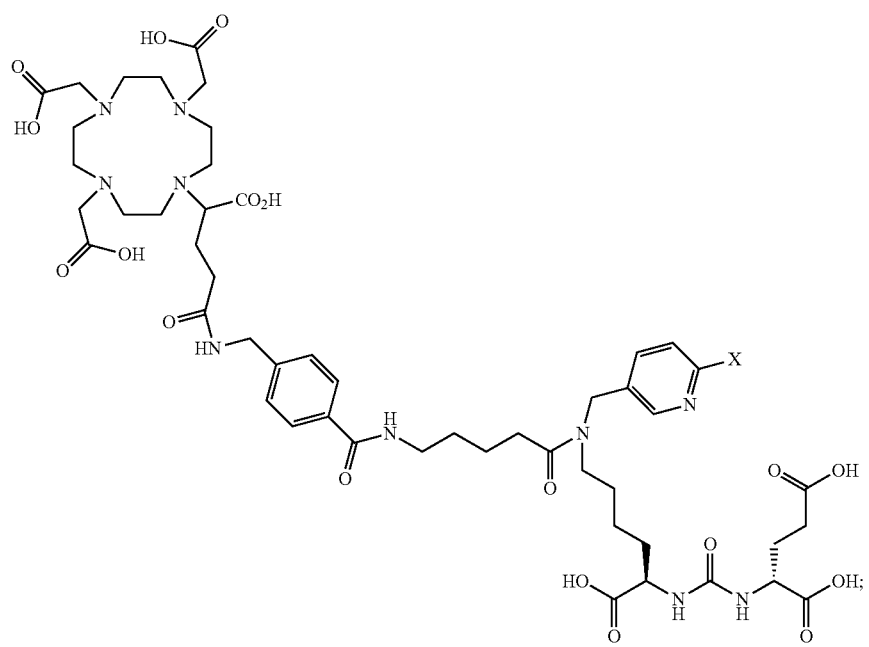

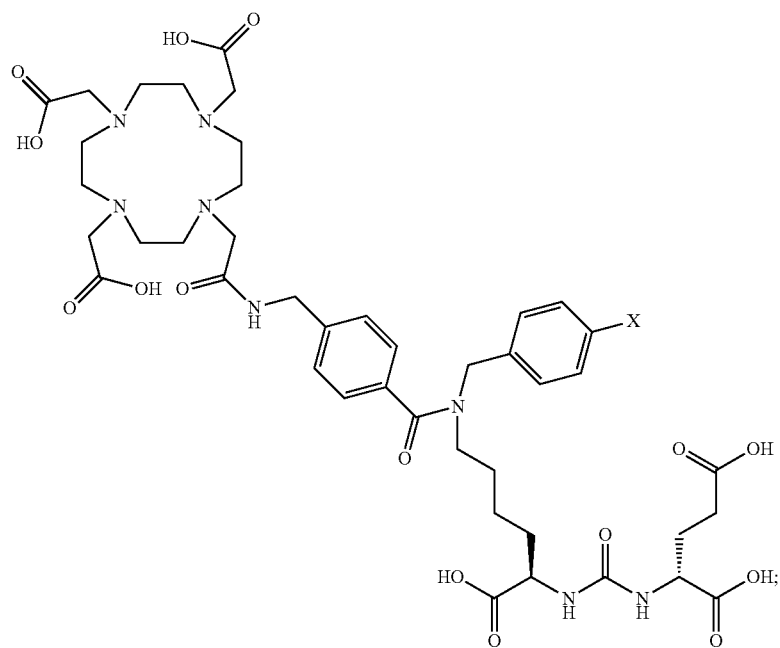
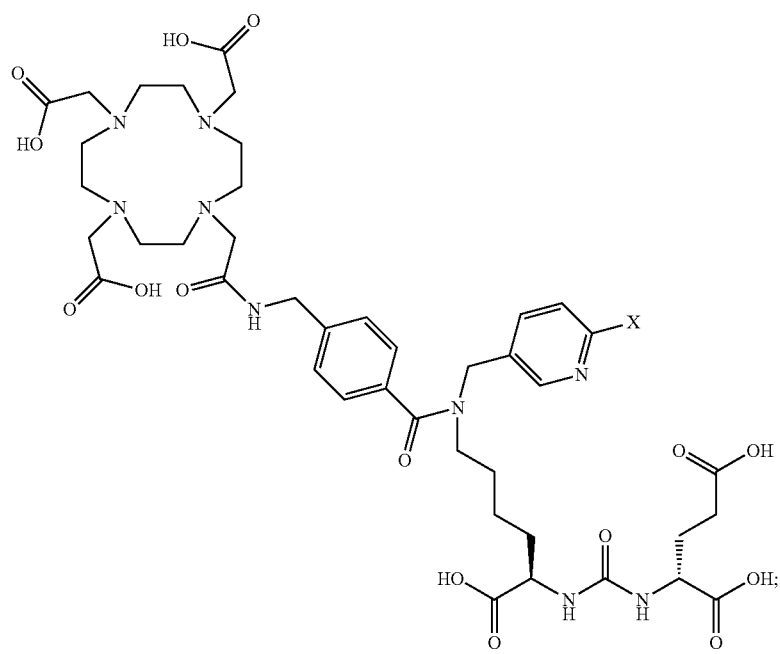

-continued
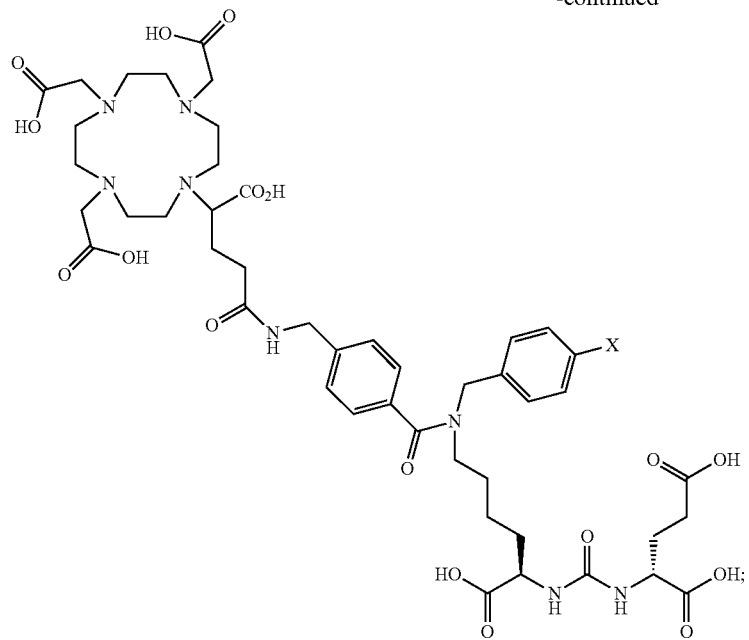
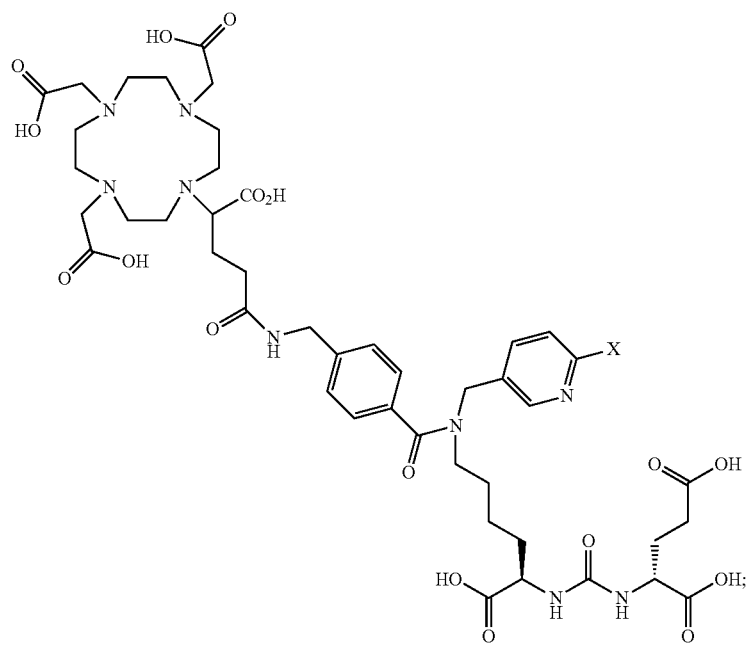

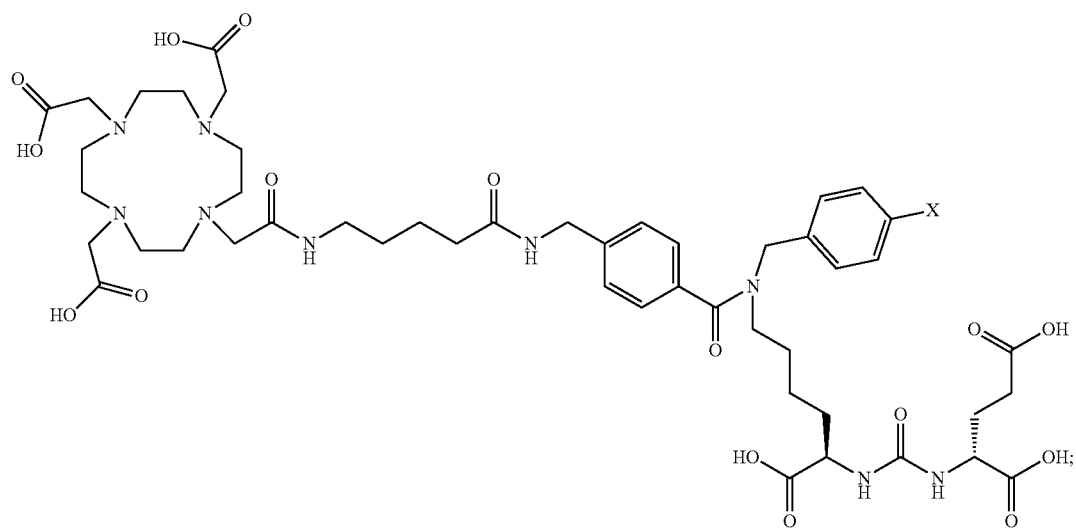
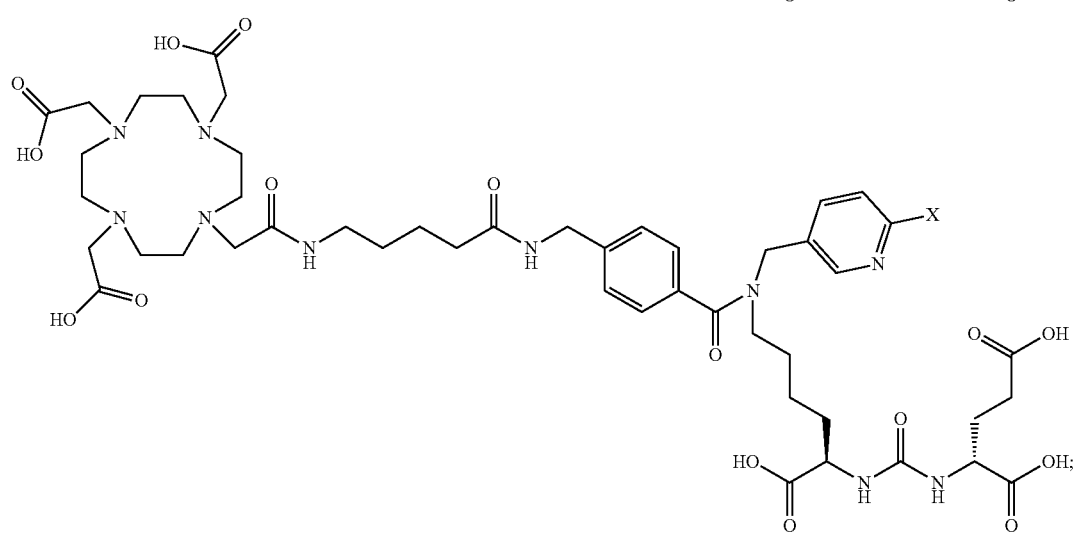
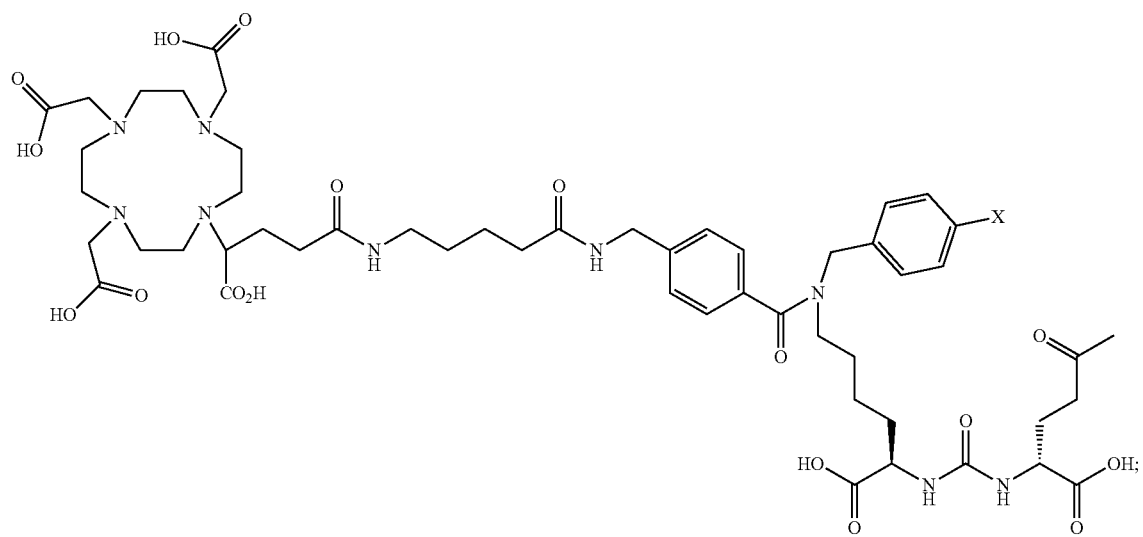

-continued
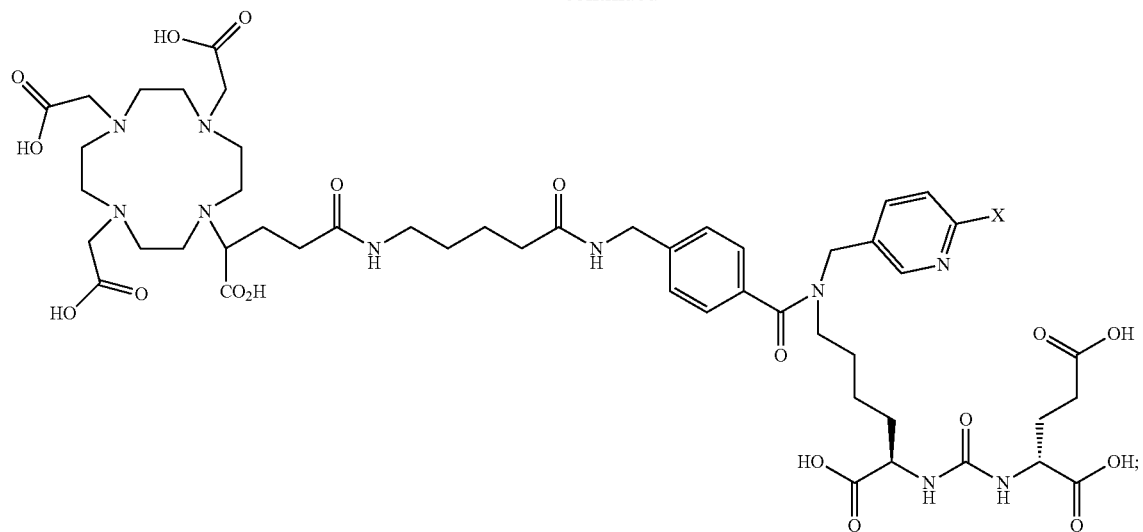
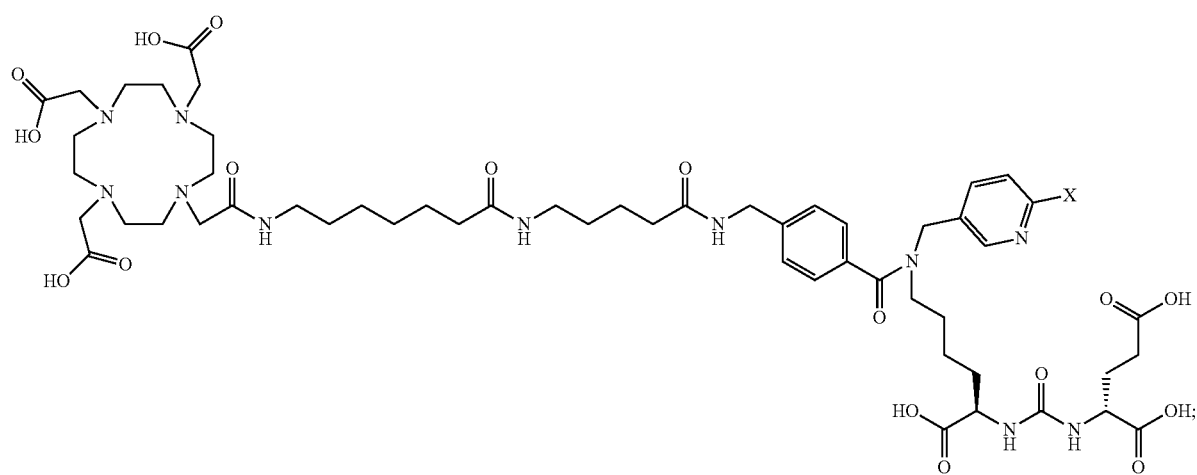
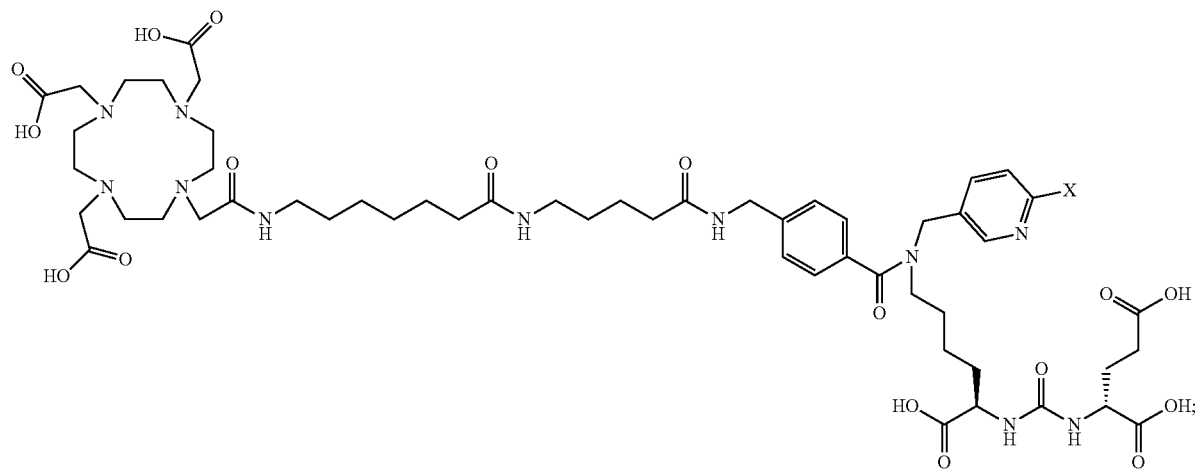

-continued
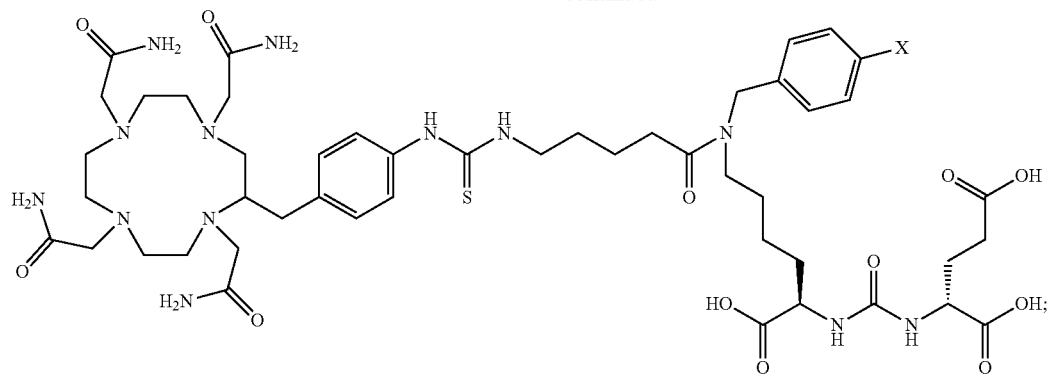
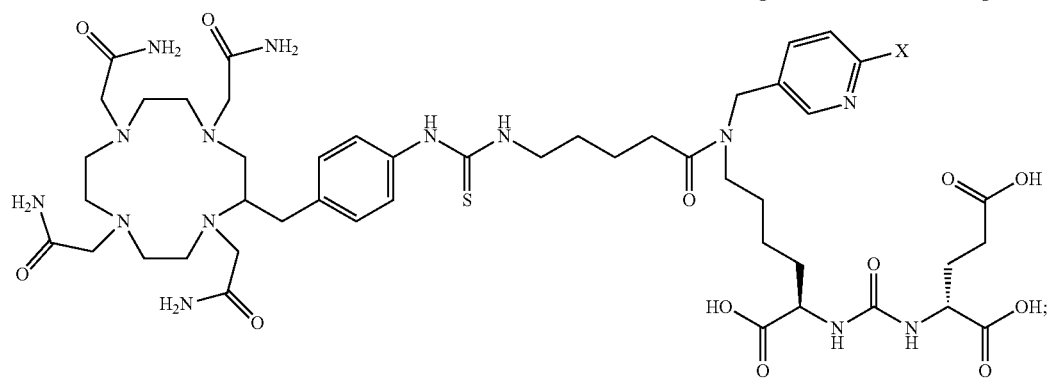
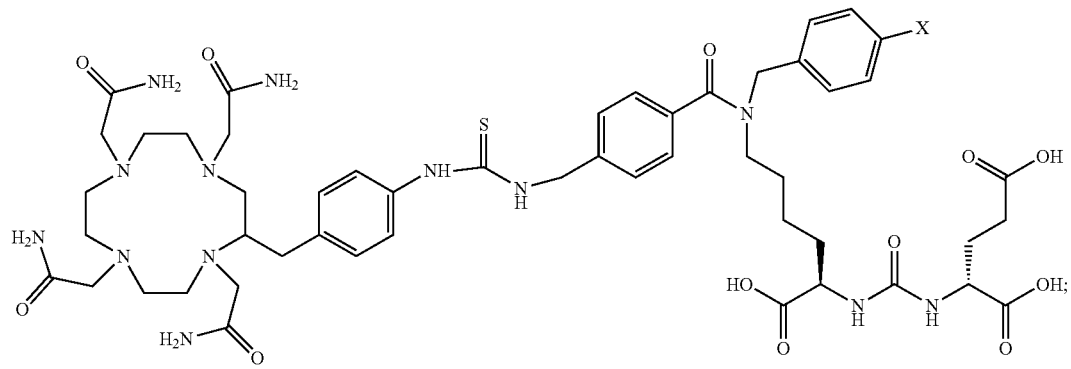
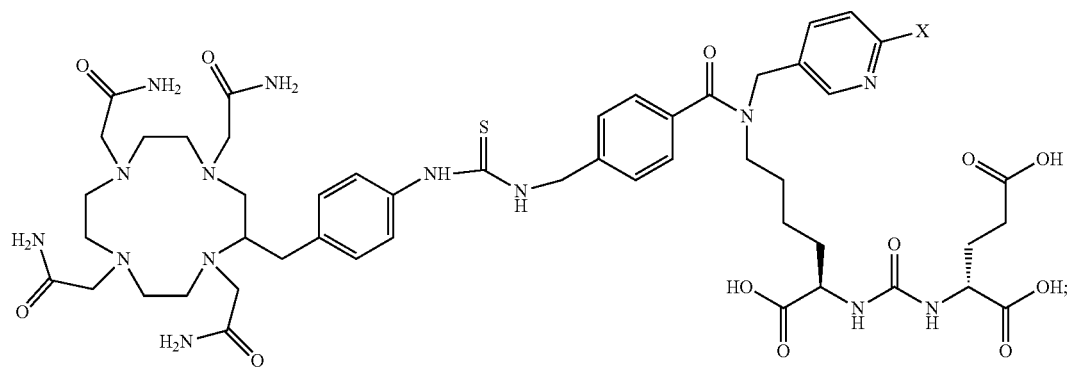

-continued
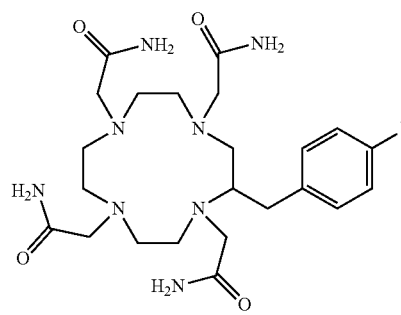 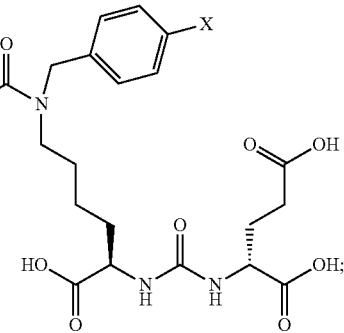
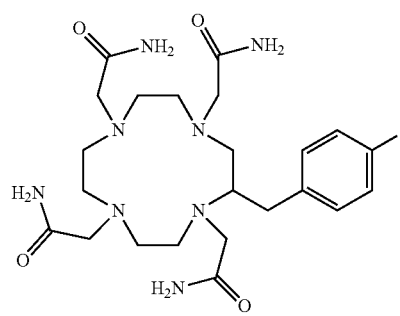 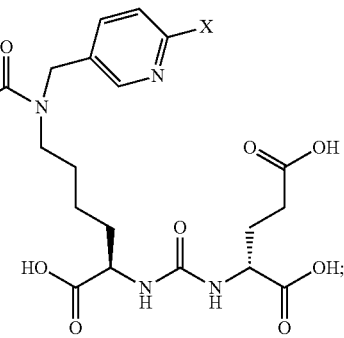
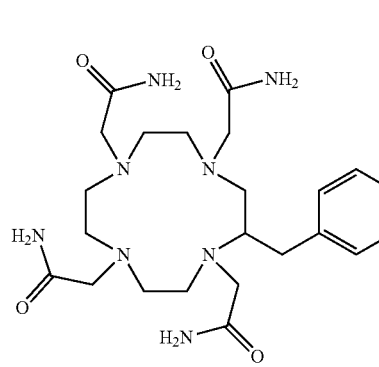 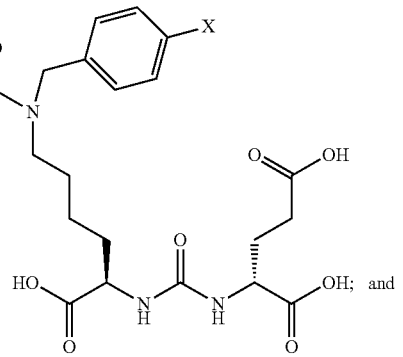
; and
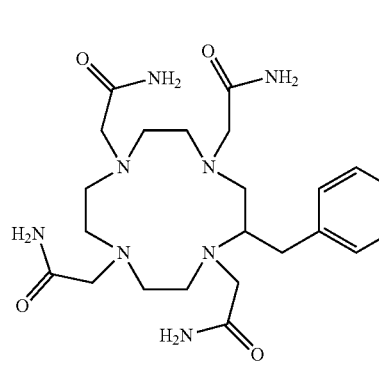 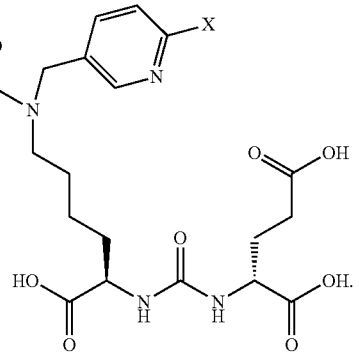
.

In more particular embodiments, X is $^{125}$I or $^{211}$At.

In some embodiments, the compound of formula (I) has the following formula:

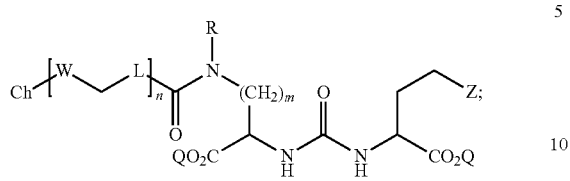

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ is selected from the group consisting of:

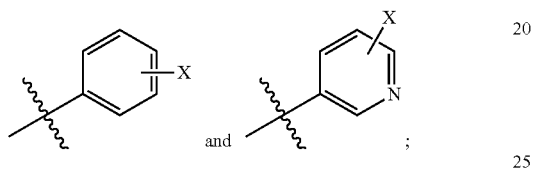

wherein X is selected from the group consisting of a radioisotope of iodine, a radioisotope of bromine, and a radioisotope of astatine; L is a linker selected from the group consisting of $C_1$-$C_6$ alkylene, including $C_1$, $C_2$, $C_3$, $C_4$, $C_5$, and $C_6$ alkylene, $C_3$-$C_6$ cycloalkylene, including $C_3$, $C_4$, $C_5$, and $C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl, including $C_1$, $C_2$, $C_3$, and $C_4$ alkyl; n is an integer selected from the group consisting of 1, 2, and 3; Ch is a chelating agent that can comprise a metal; and pharmaceutically acceptable salts thereof.

In particular embodiments, the compound of formula (I) has the following formula:

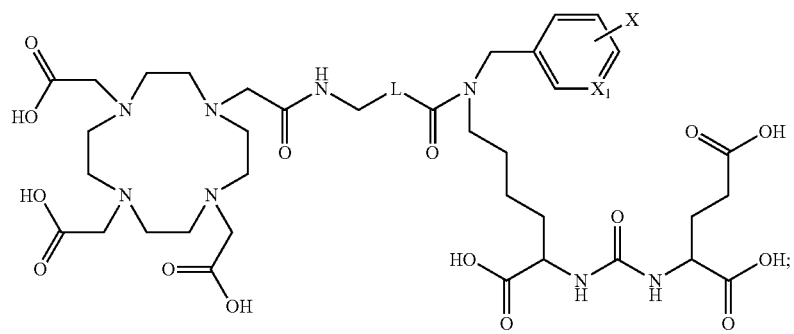

wherein L is selected from $C_1$, $C_2$, $C_3$, $C_4$, $C_5$, and $C_6$ alkylene; wherein $X_1$ is —$CR^3$, —C—X, or N, wherein $R^3$ is H or $C_1$-$C_4$ alkyl; and wherein X is selected from the group consisting of a radioisotope of iodine, a radioisotope of bromine, and a radioisotope of astatine.

In more particular embodiments, the compound of formula (I) is:

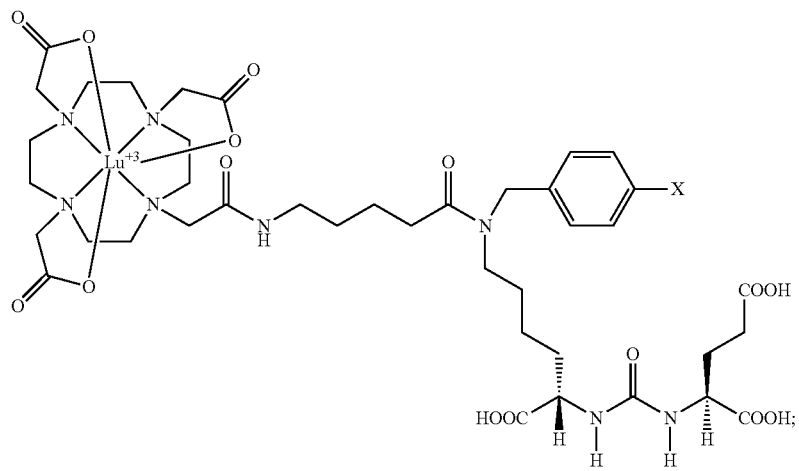

wherein X is $^{125}$I or [211]At.

In other embodiments, the compound of formula (I) has the following formula:

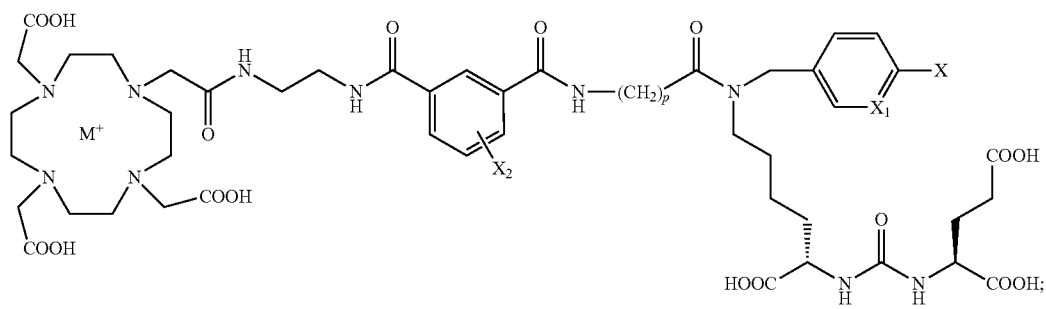

wherein: p is an integer selected from the group consisting of 1, 2, 3, 4, 5, and 6; and X is halogen; $X_1$ is —$CR^3$, —C—X, or N, wherein $R^3$ is H or $C_1$-$C_4$ alkyl; and $X_2$ is selected from the group consisting of a radioisotope of iodine, a radioisotope of bromine, and a radioisotope of astatine; and wherein $M^+$ is a metal, which can be present or absent. In particular embodiments, $M^+$ is a metal selected from the group consisting of: Y, Lu, Tc, Zr, In, Sm, Re, Cu, Pb, Ac, Bi, Al, Ga, Re, Ho and Sc, and radioisotopes thereof.

In certain embodiments, the compound of formula (I) is selected from the group consisting of:

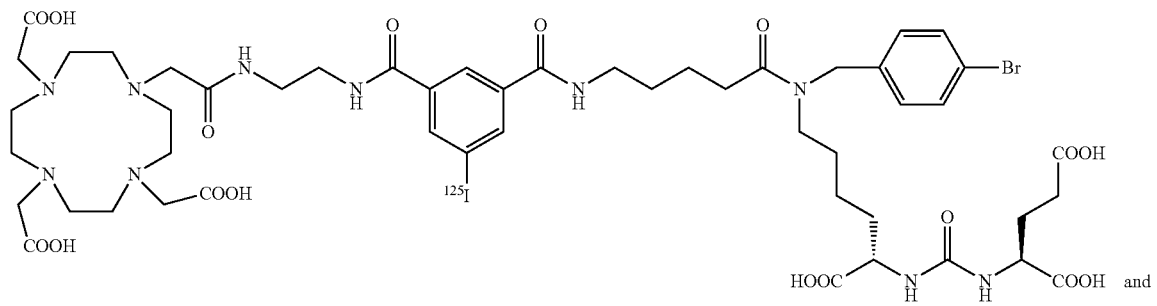

[$^{125}$I]VK-13-13

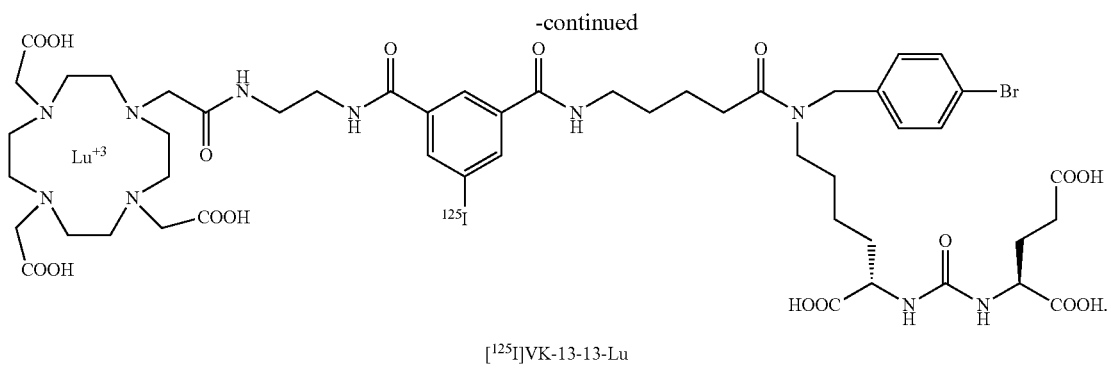

[$^{125}$I]VK-13-13-Lu

B. Methods of Treating PSMA Expressing Tumors or Cells

In some embodiments, the presently disclosed subject matter provides a method for treating one or more PSMA expressing tumors or cells, the method comprising contacting the one or more PSMA expressing tumors or cells with an effective amount of a compound of formula (I), the compound of formula (I) comprising:

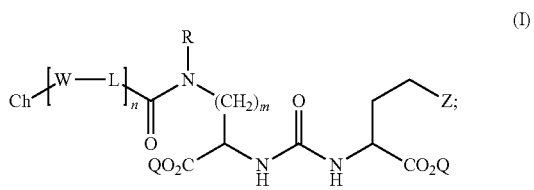

(I)

wherein: Z is tetrazole or $CO_2Q$; Q is H or a protecting group; m is an integer selected from the group consisting of 1, 2, 3, 4, and 5; R is independently H or —$CH_2$—$R^1$; wherein $R^1$ is:

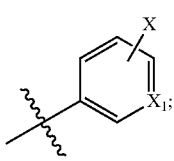

wherein $X_1$ is —$CR^3$, —C—X, or N, wherein $R^3$ is H or $C_1$-$C_4$ alkyl; wherein X is selected from the group consisting of a radioisotope of iodine, a radioisotope of bromine, and a radioisotope of astatine; or X is halogen when at least one L is a substituted arylene; L is a linker selected from the group consisting of $C_1$, $C_2$, $C_3$, $C_4$, $C_5$, and $C_6$ alkylene, $C_3$, $C_4$, $C_5$, and $C_6$ cycloalkylene, and arylene, each of which can be substituted to unsubstituted; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or $C_1$-$C_4$ alkyl; n is an integer selected from the group consisting of 1, 2, and 3; Ch is a chelating agent that can comprise a metal; and pharmaceutically acceptable salts thereof.

In particular embodiments, $R^1$ is selected from the group consisting of:

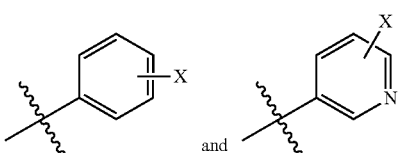

In yet more particular embodiments, X is selected from the group consisting of $^{125}$I, $^{124}$I, $^{123}$I, $^{131}$I, $^{211}$At, $^{77}$Br, and $^{80m}$Br. In certain embodiments, at least one L is substituted arylene and X is halogen.

In even yet more particular embodiments, the chelating agent is selected from the group consisting of:

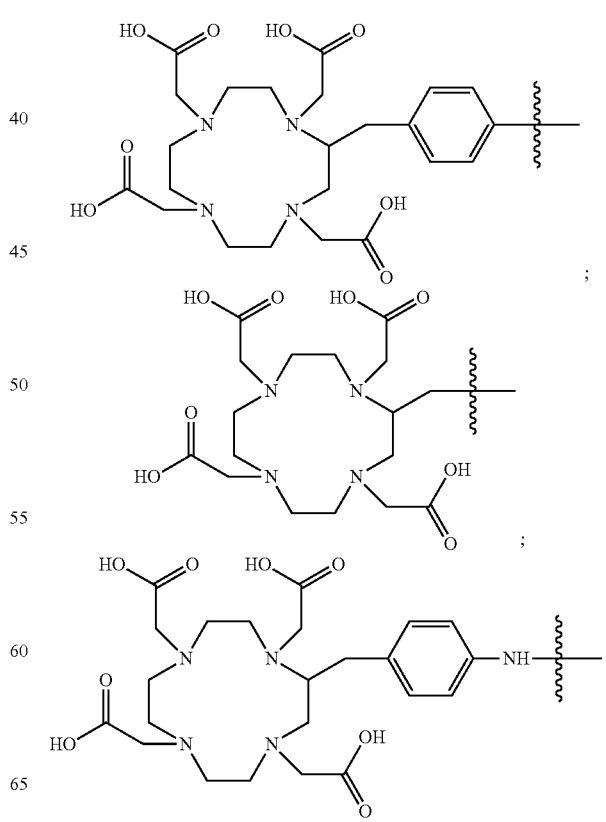

39
-continued
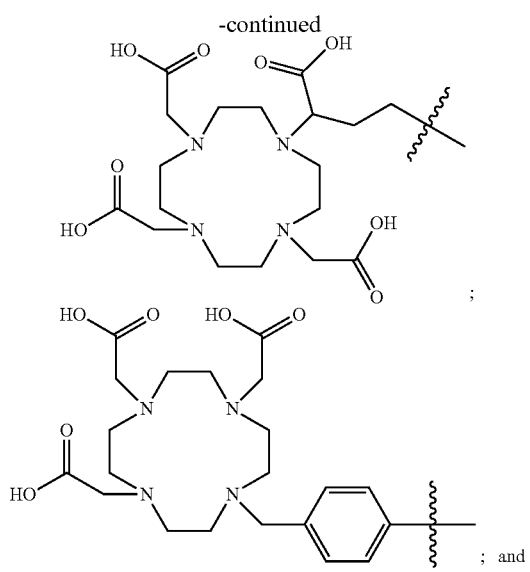
;and
40
-continued
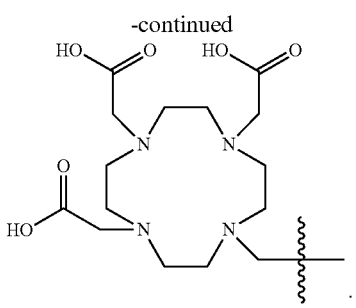
.
In certain embodiments, the metal chelating agent comprises a metal selected from the group consisting of: Y, Lu, Tc, Zr, In, Sm, Re, Cu, Pb, Ac, Bi, Al, Ga, Re, Ho and Sc, and radioisotopes thereof. In more certain embodiments, the metal is $^{175}$Lu.
In particular embodiments, the compound of formula (I) is selected from the group consisting of:
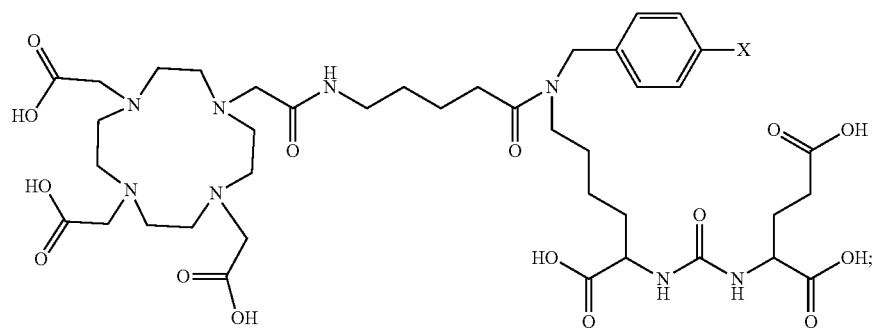
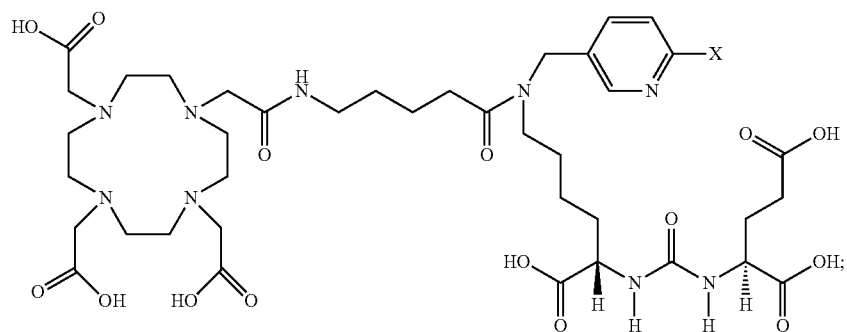
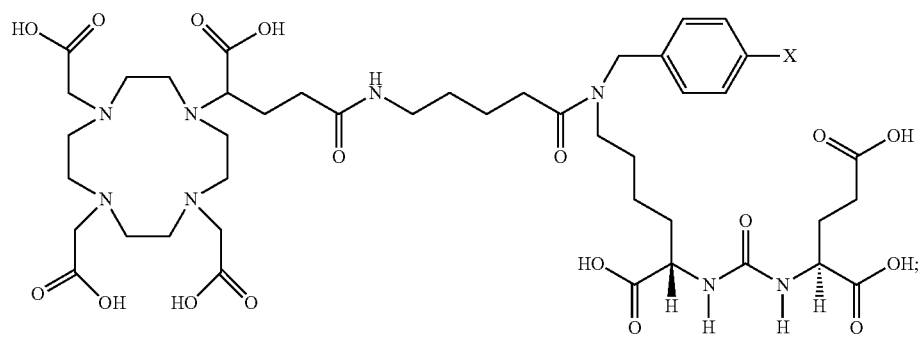

-continued
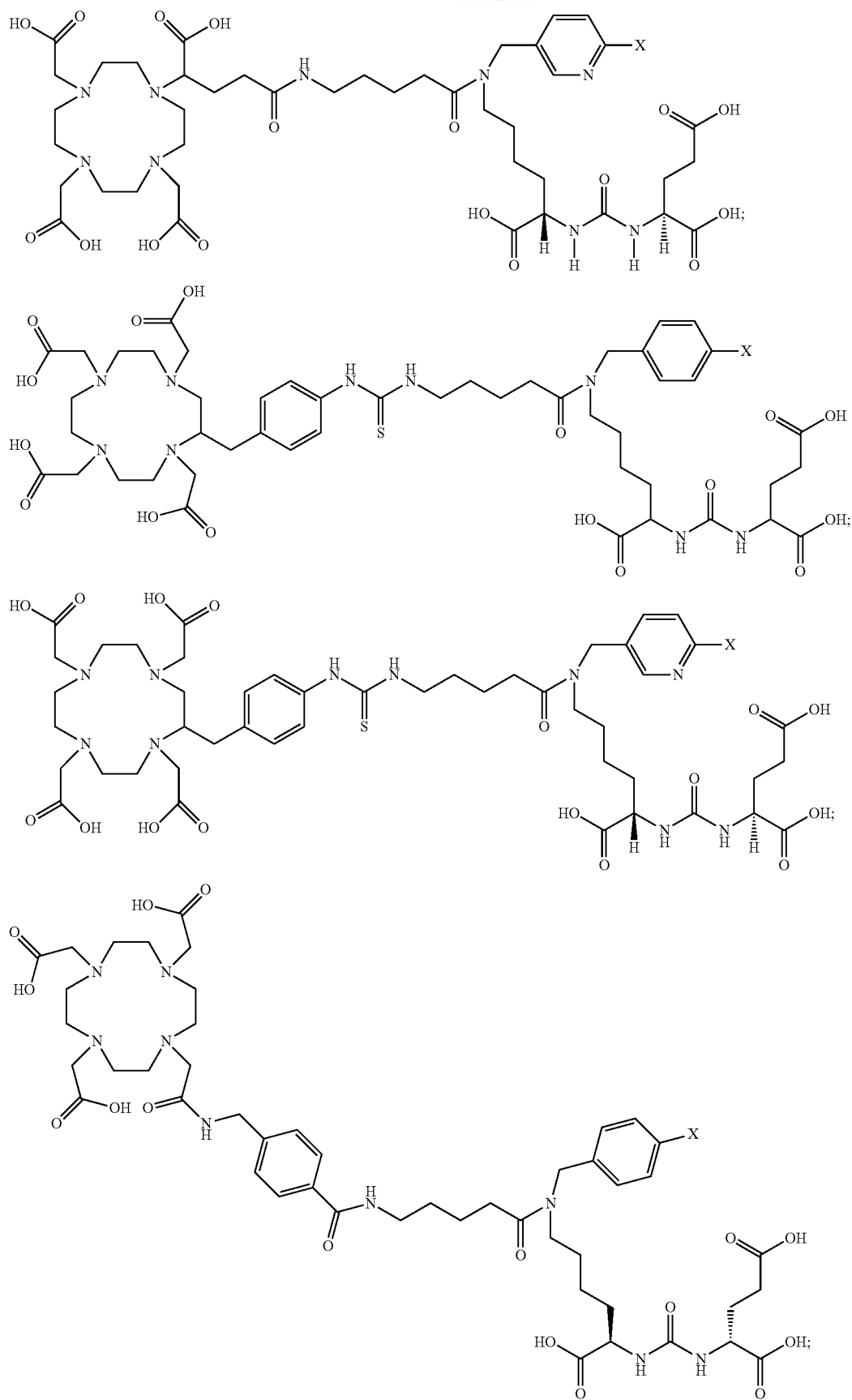

-continued
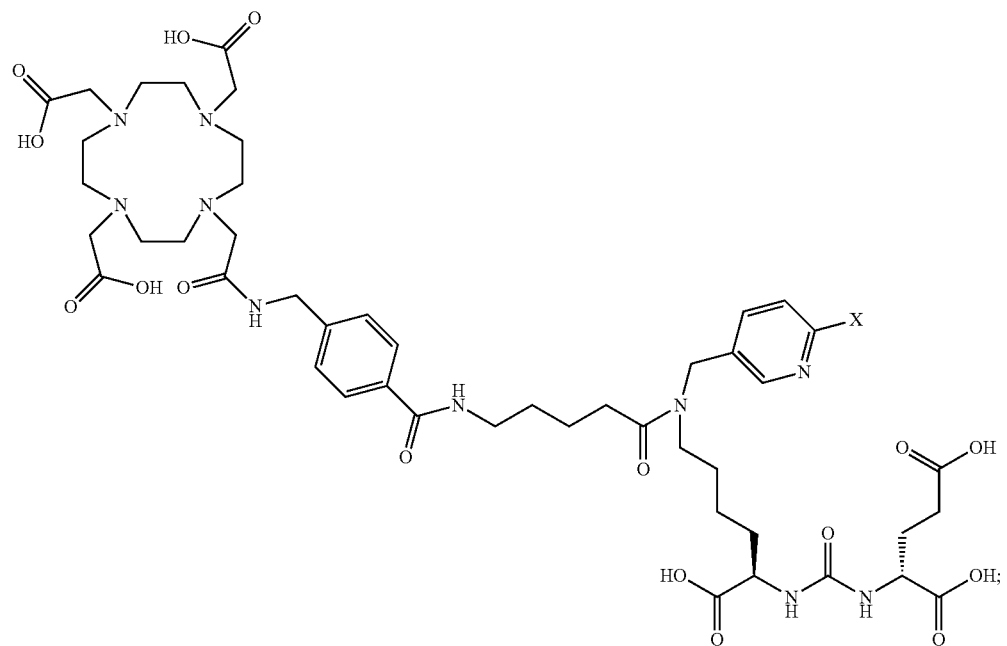
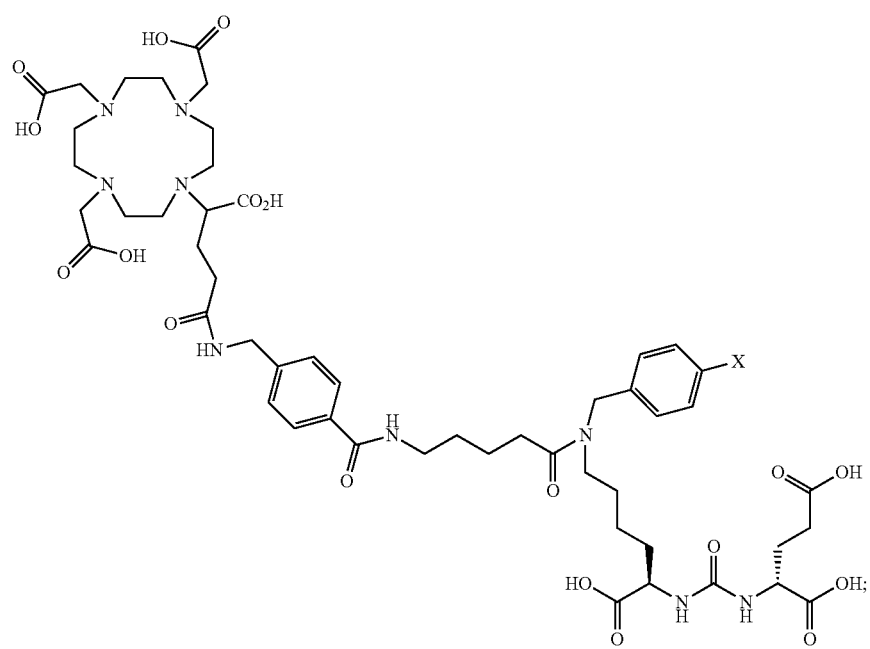

-continued
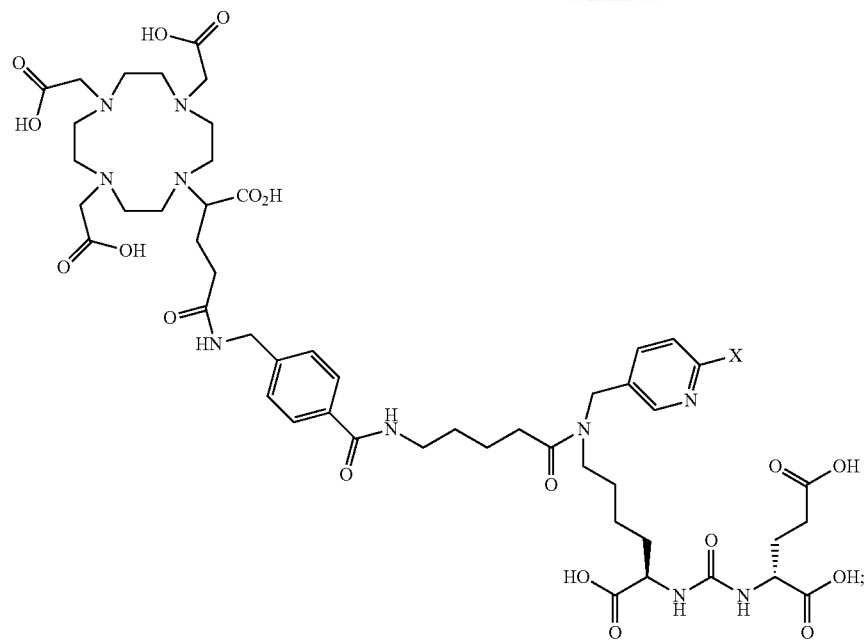
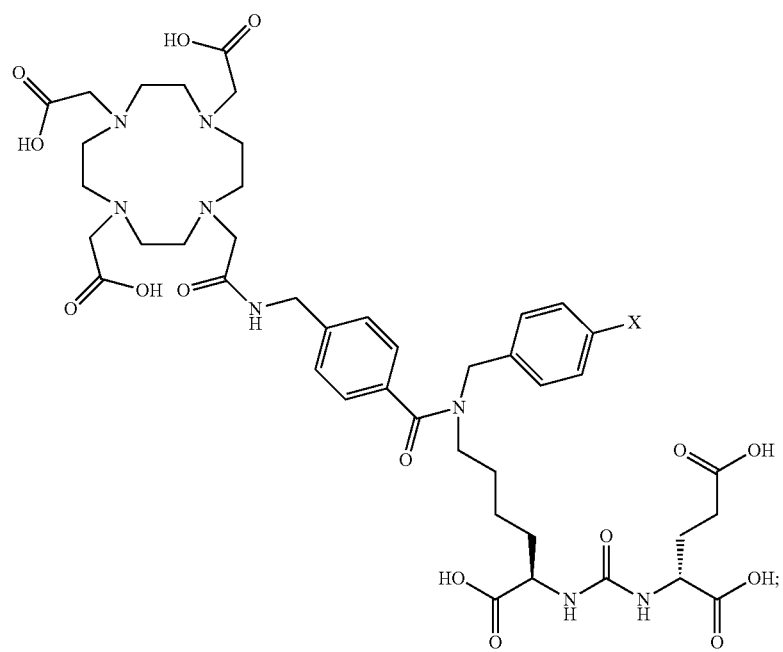

-continued
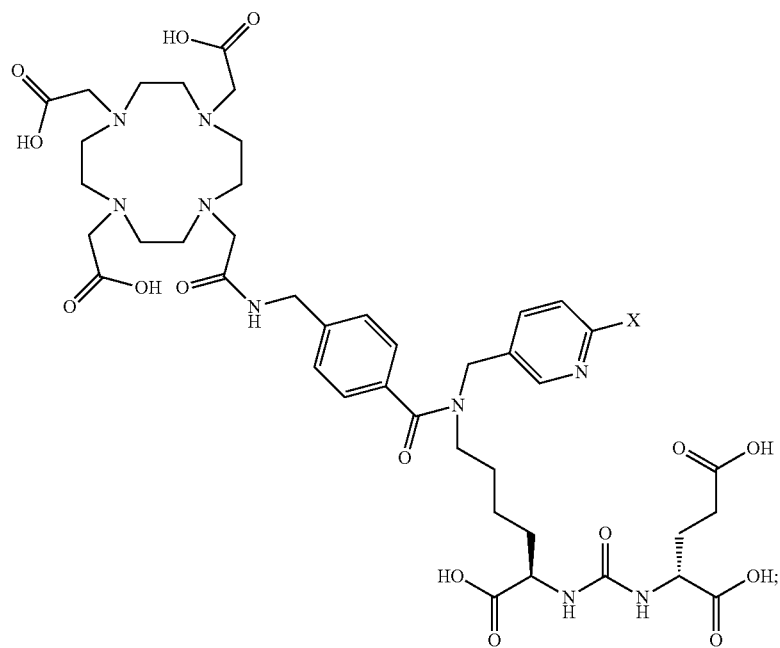
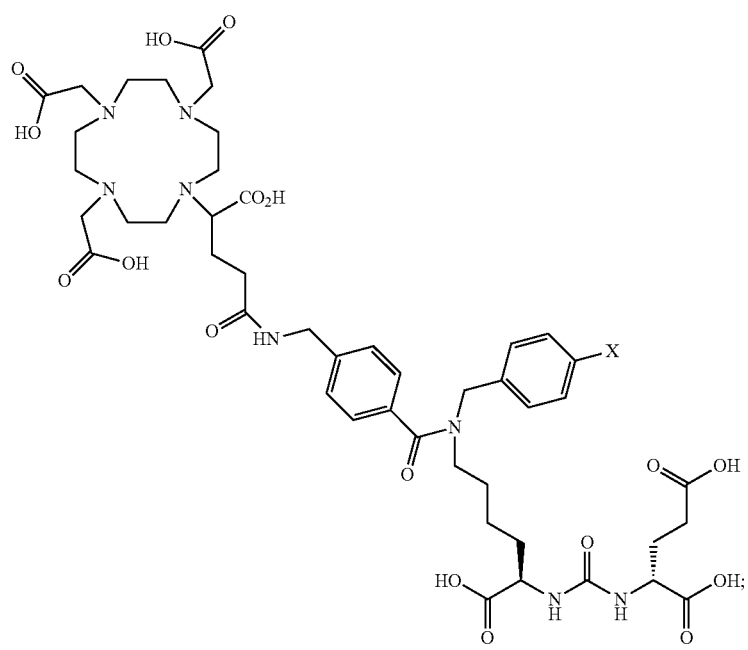

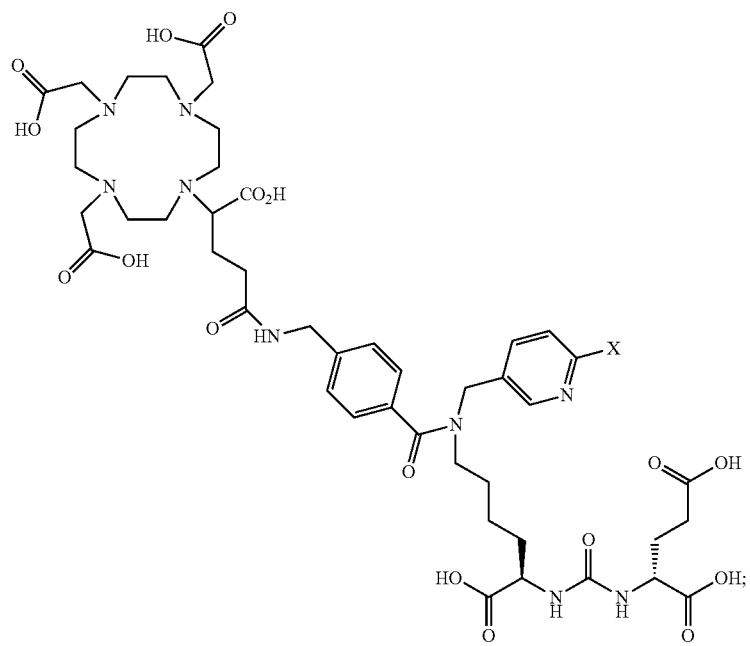
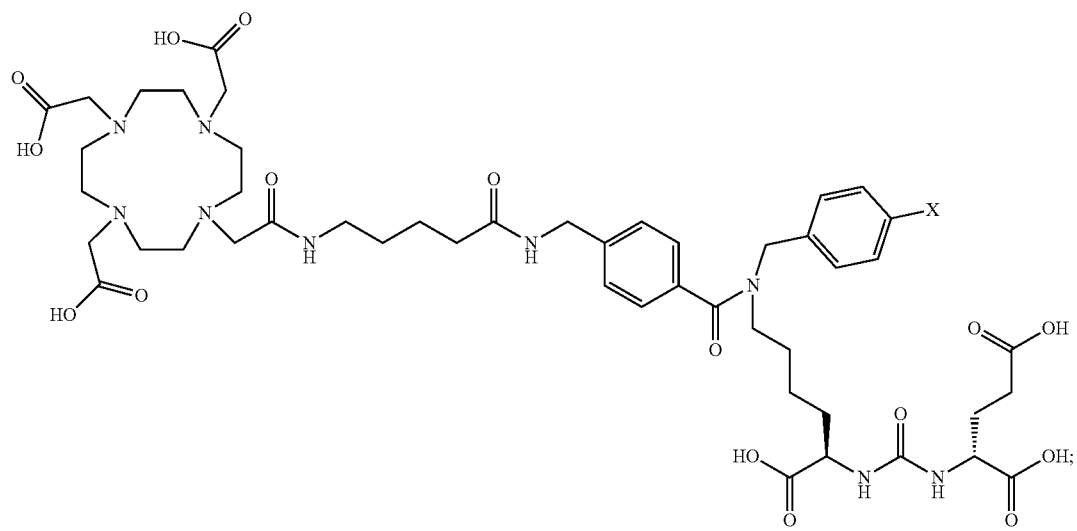
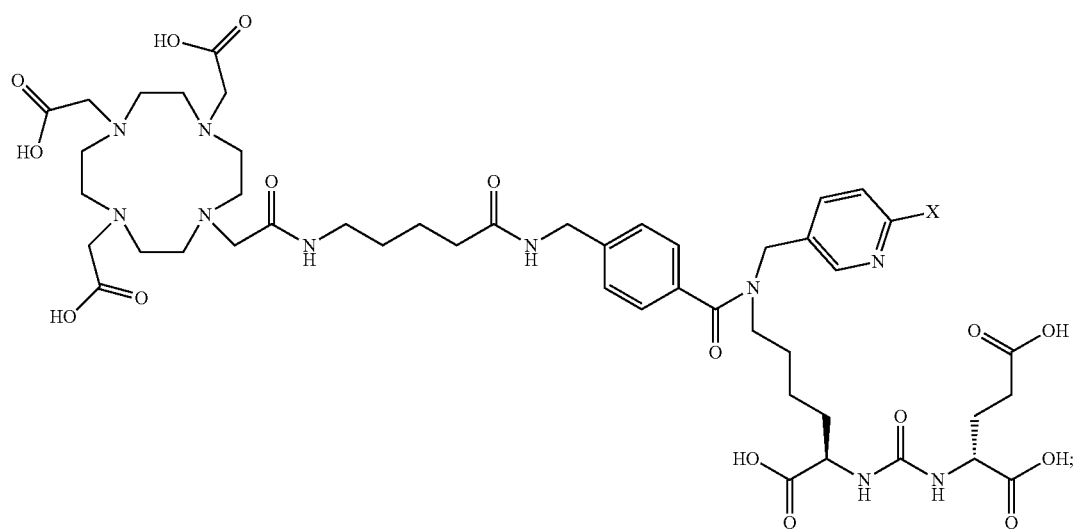

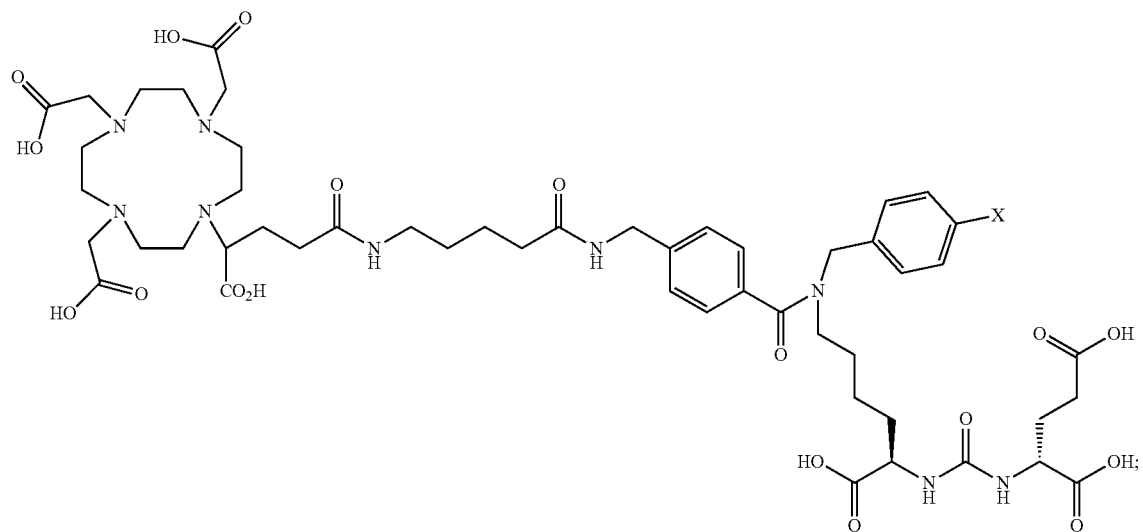
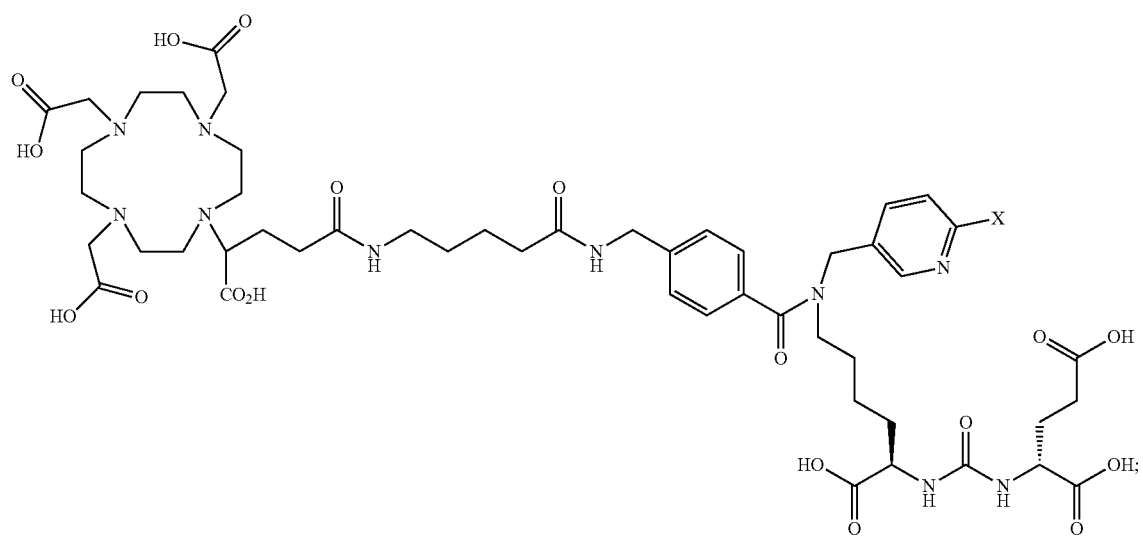
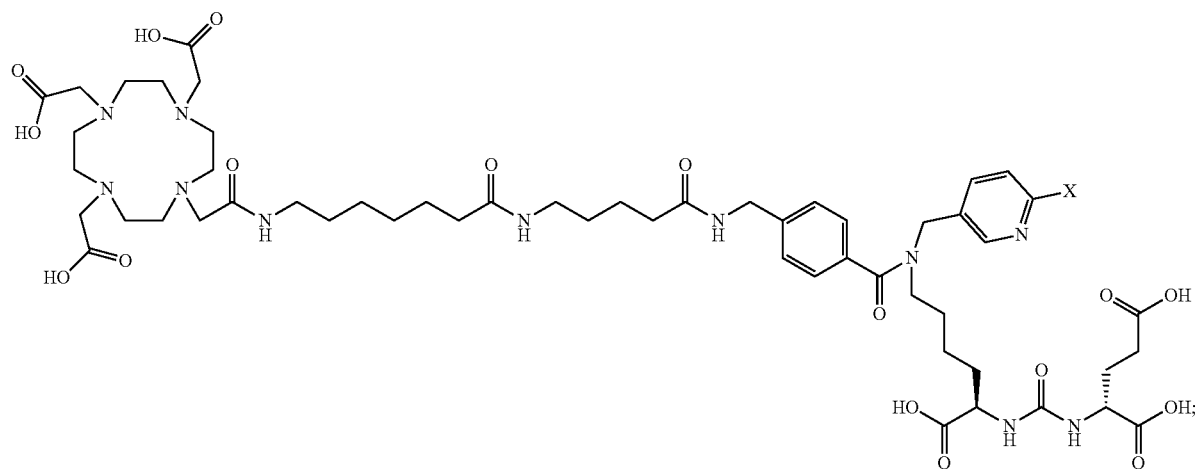

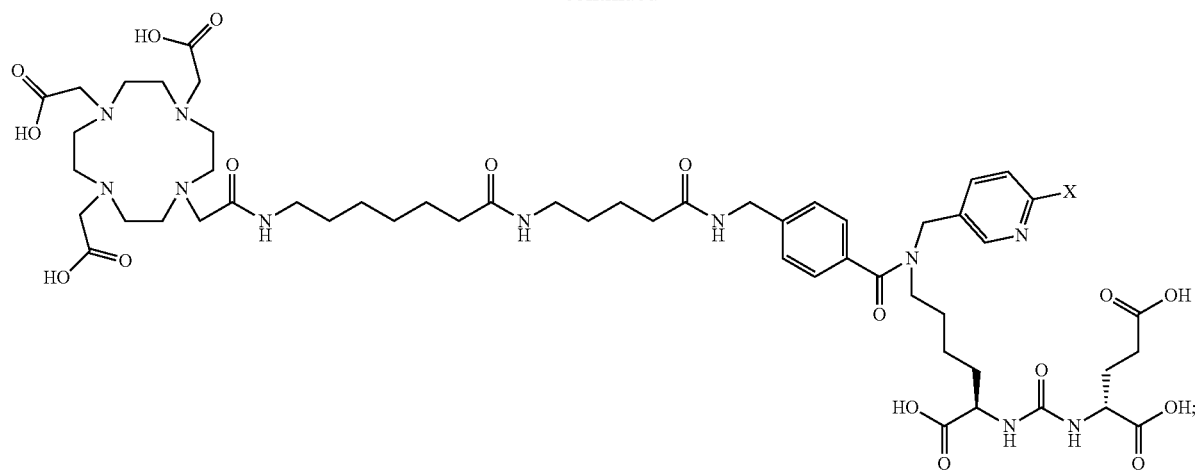
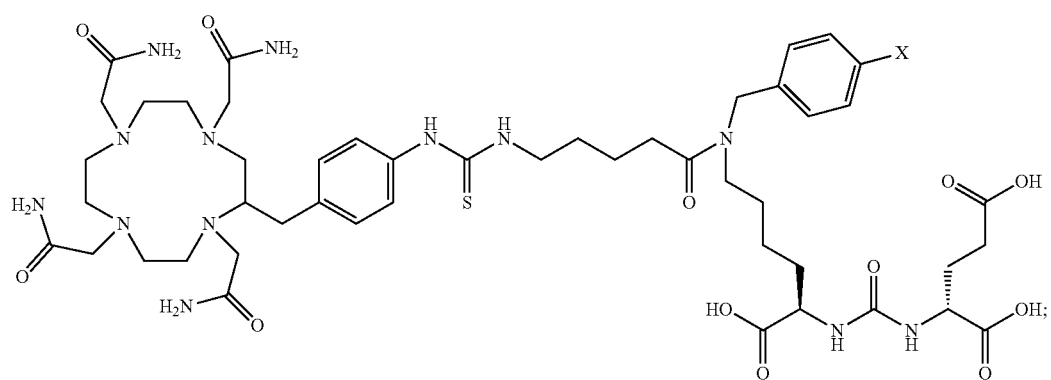
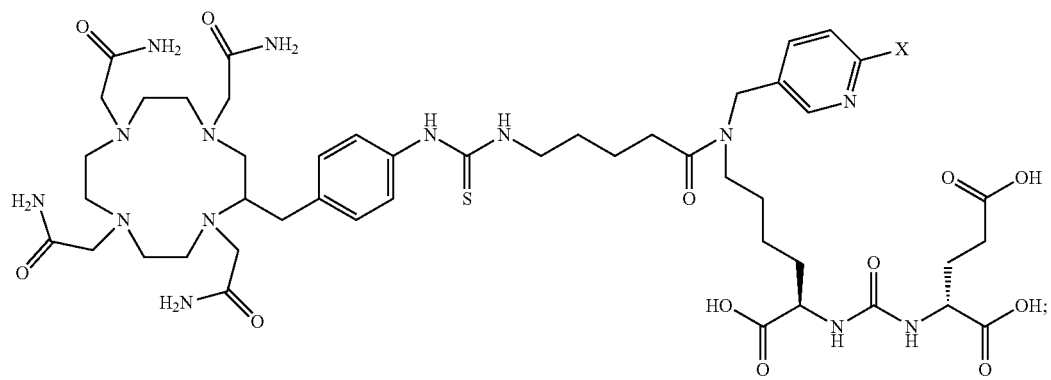
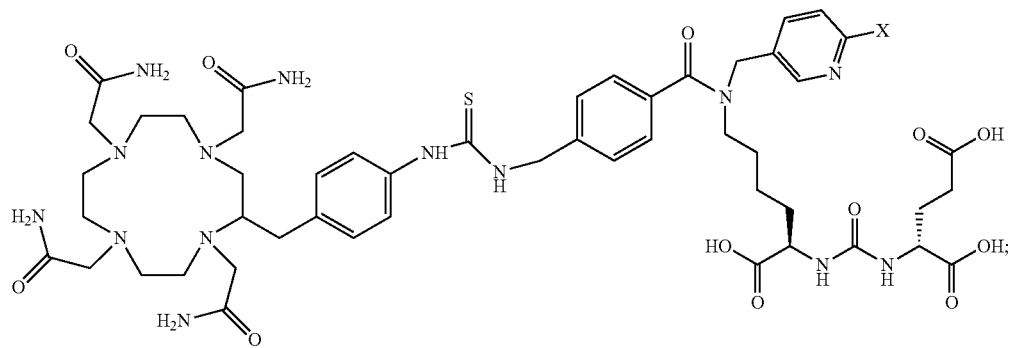

-continued
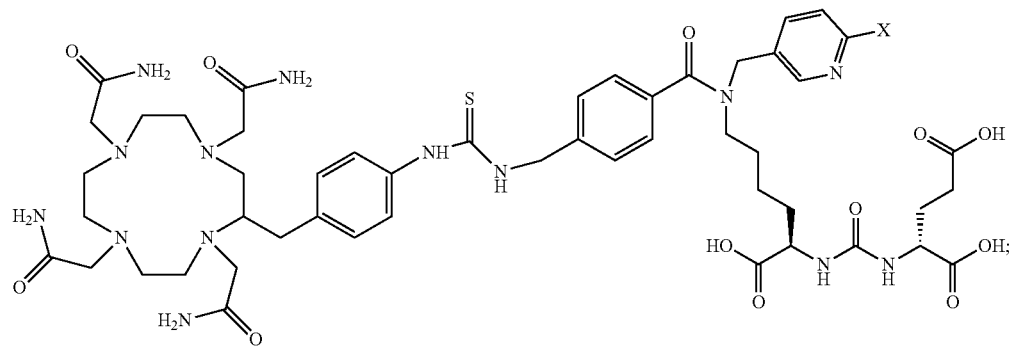
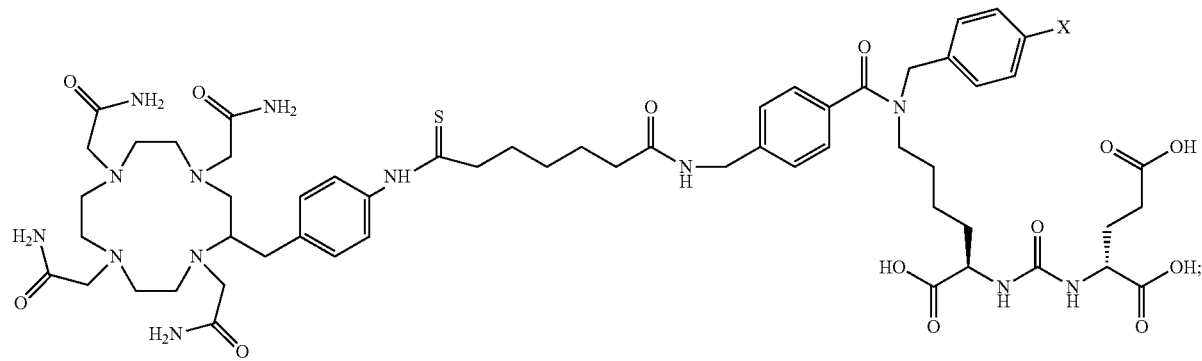
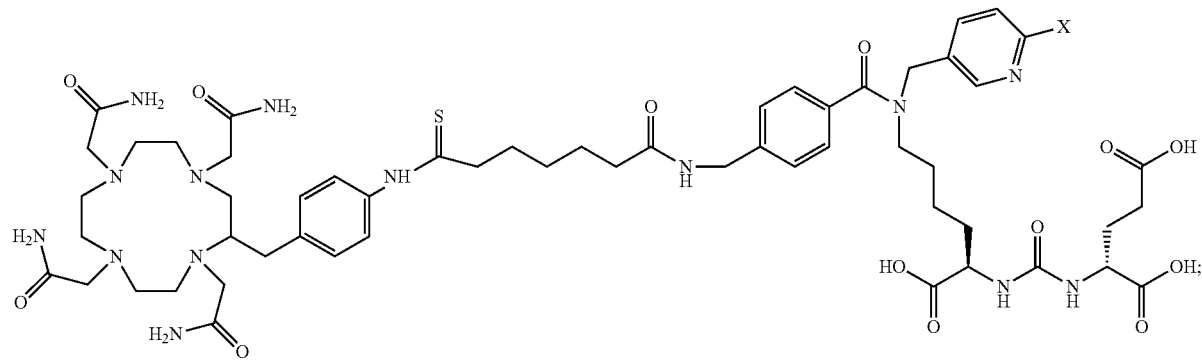
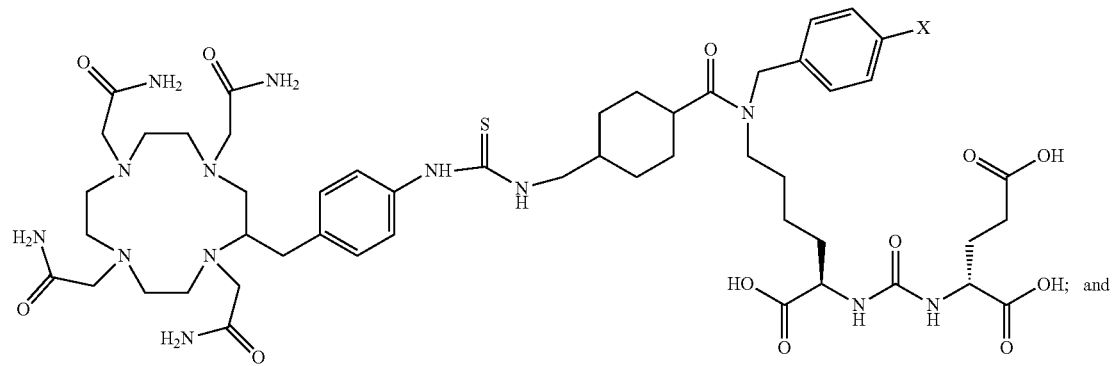

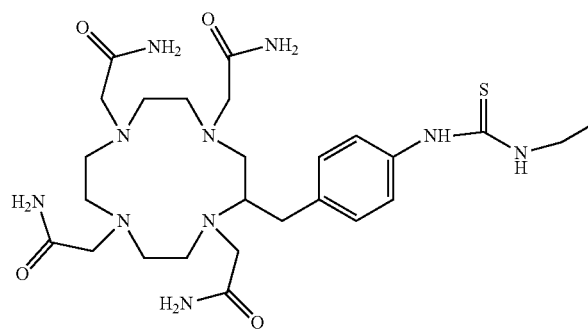

In more particular embodiments, X is $^{125}$I or $^{211}$At.

In some embodiments, the compound of formula (I) has the following formula:

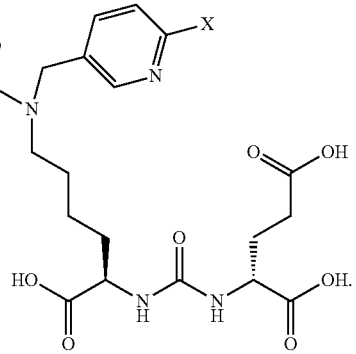

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ is selected from the group consisting of:

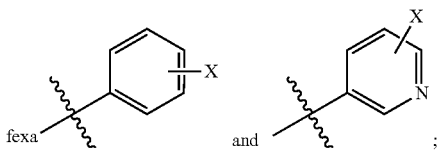

wherein X is selected from the group consisting of a radioisotope of iodine, a radioisotope of bromine, and a radioisotope of astatine; L is a linker selected from the group consisting of $C_1$-$C_6$ alkylene, including $C_1$, $C_2$, $C_3$, $C_4$, $C_5$, and $C_6$ alkylene, $C_3$-$C_6$ cycloalkylene, including $C_3$, $C_4$, $C_5$, and $C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl, including $C_1$, $C_2$, $C_3$, and $C_4$ alkyl; n is an integer selected from the group consisting of 1, 2, and 3; Ch is a chelating agent that can comprise a metal; and pharmaceutically acceptable salts thereof.

In particular embodiments, the compound of formula (I) has the following formula:

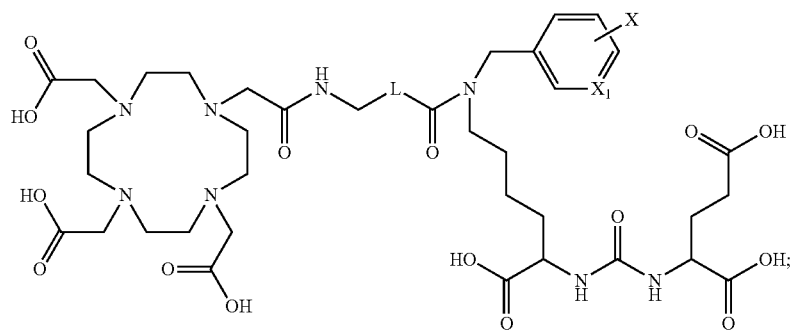

wherein L is selected from $C_1$, $C_2$, $C_3$, $C_4$, $C_5$, and $C_6$ alkylene; wherein $X_1$ is —$CR^3$, —C—X, or N, wherein $R^3$ is H or $C_1$-$C_4$ alkyl; and wherein X is selected from the group consisting of a radioisotope of iodine, a radioisotope of bromine, and a radioisotope of astatine.

In more particular embodiments, the compound of formula (I) is:

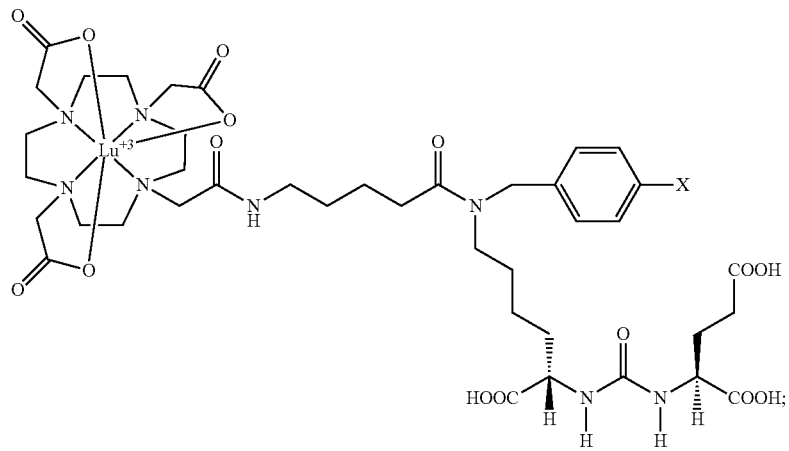

wherein X is $^{125}$I or $^{211}$At.

In other embodiments, the compound of formula (I) has the following formula:

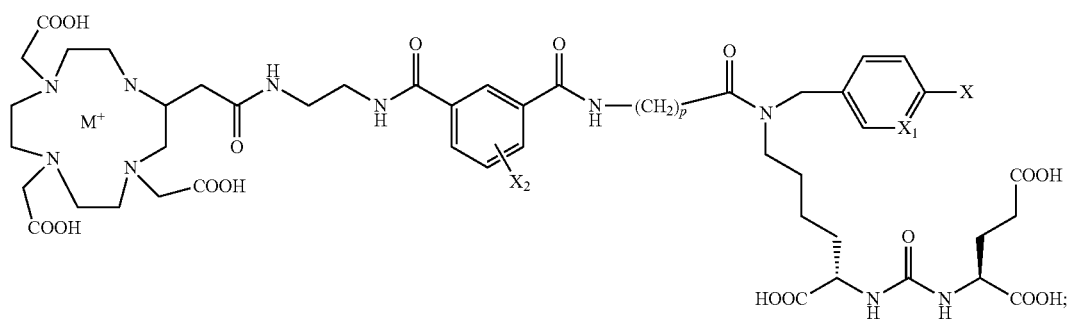

wherein: p is an integer selected from the group consisting of 1, 2, 3, 4, 5, and 6; and X is halogen; $X_1$ is —$CR^3$, —C—X, or N, wherein $R^3$ is H or $C_1$-$C_4$ alkyl; and $X_2$ is selected from the group consisting of a radioisotope of iodine, a radioisotope of bromine, and a radioisotope of astatine; and wherein $M^+$ is a metal, which can be present or absent. In particular embodiments, $M^+$ is a metal selected from the group consisting of: Y, Lu, Tc, Zr, In, Sm, Re, Cu, Pb, Ac, Bi, Al, Ga, Re, Ho and Sc, and radioisotopes thereof.

In certain embodiments, the compound of formula (I) is selected from the group consisting of:

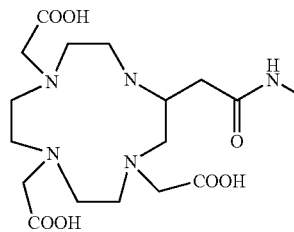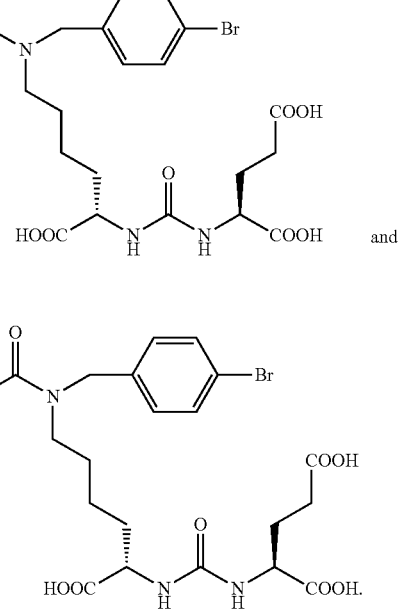

[$^{125}$]VK-03-03

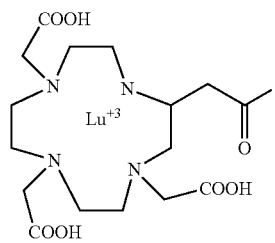

[$^{125}$]VK-03-03-Lu

In some embodiments, the one or more PSMA-expressing tumor or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cells, a stomach tumor or cell, and combinations thereof.

In certain embodiments, the one or more PSMA-expressing tumor or cells is a prostate tumor or cell. In some embodiments, the one or more PSMA-expressing tumor or cell is in vitro, in vivo, or ex vivo. In particular embodiments, the one or more PSMA-expressing tumor or cells is present in a subject. In yet more particular embodiments, the subject is human.

In some embodiments, the method of treatment results in inhibition of tumor growth.

In certain embodiments, the method further comprises administering a blocking agent in combination with the compound of formula (I), wherein the blocking agent is a competitive PSMA ligand that reduces accumulation of the compound of formula (I) in one or more PSMA expressing cells in an off-target organ. In particular embodiments, the off-target organ is selected from the group consisting of blood, stomach, spleen, thyroid gland, salivary gland, lacrimal gland, and kidney. In yet more particular embodiments, the off-target organ is the kidney or salivary gland.

In certain embodiments, the blocking agent comprises a PSMA-based blocking agent, e.g., a competitive PSMA ligand. In more certain embodiments, the PSMA-based blocking agent is a compound of formula (I) that is not radiohalogenated, wherein the compound of formula (I) used as a blocking agent and the compound of formula (I) used as a therapeutic agent can be the same or different.

In particular embodiments, the PSMA-based blocking agent is:

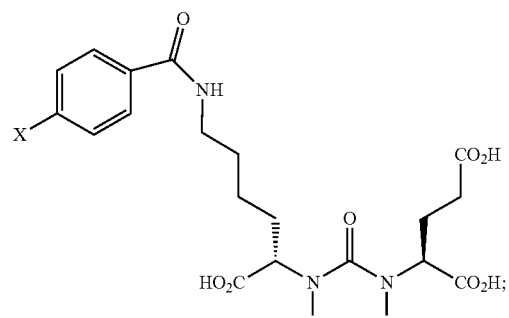

YC-I-27 and related compounds disclosed in International PCT Patent Application Publication No. WO/2017/070482, to Pomper et al., published Apr. 27, 2017, which is incorporated herein by reference in its entirety, wherein X is a halogen, including iodine.

The term "combination" is used in its broadest sense and means that a subject is administered at least two agents, more particularly a compound of formula (I), and optionally, one or more other agents, e.g., a blocking agent. More particularly, the term "in combination" refers to the concomitant administration of two (or more) agents for the treatment of a, e.g., single disease state. As used herein, the agents may be combined and administered in a single dosage form, may be administered as separate dosage forms at the same time, or may be administered as separate dosage forms that are administered sequentially. In such embodiments, the blocking agent can be administered at the same time as the radiotherapeutic compound of formula (I) or prior to administering the radiotherapeutic compound of formula (I). Accordingly, in some embodiments, the blocking agent is administered concurrently with the radiotherapeutic compound of formula (I), in some embodiments, 30 minutes before administering the compound of formula (I), and in some embodiments, 29, 28, 27, 26, 25, 24, 23, 22, 21, 20, 19, 18, 17, 16, 15, 14, 13, 12, 11, 10, 9, 8, 7, 6, 5, 4, 3, 2, or 1 minute before administering the compound of formula (I).

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

"Contacting" means any action which results in at least one compound comprising the treating agent of the presently disclosed subject matter physically contacting at least one or more PSMA-expressing tumors or cells. Contacting can include exposing the PSMA-expressing tumors or cells to the compound in an amount sufficient to result in contact of at least one compound with at least one PSMA– expressing tumor or cell.

By "agent" is meant a compound of formula (I) or another agent, e.g., a peptide, nucleic acid molecule, or other small molecule compound administered in combination with a compound of formula (I).

More particularly, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be an antibiotic or a nutrient. A therapeutic agent may decrease, suppress, attenuate, diminish, arrest, or stabilize the development or progression of disease, disorder, or condition in a host organism.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In other embodiments, the one or more PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In more specific embodiments, the one or more PSMA-expressing tumor or cell is a prostate tumor or cell. In some embodiments, the one or more PSMA-expressing tumors or cells are in vitro, in vivo, or ex vivo. In particular embodiments, the one or more PSMA– expressing tumors or cells are present in a subject.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In some embodiments, the compound of formula (I) is cleared from the subject's kidneys in about 24 hours.

In some embodiments, the presently disclosed methods use compounds that are stable in vivo such that substantially all, e.g., more than about 50%, 60%, 70%, 80%, or more preferably 90% of the injected compound is not metabolized by the body prior to excretion. In other embodiments, the compound comprising the imaging agent is stable in vivo.

In specific embodiments, the method results in inhibition of the tumor growth. As used herein, the term "inhibition" or "reduction" and grammatical derivations thereof, refers to the ability of an agent to block, partially block, interfere, decrease, reduce or deactivate a biological molecule, pathway or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%.

In other specific embodiments, the compound of formula (I) completely occupies the binding cavity of the PSMA expressing tumors or cells.

C. Methods of Imagining PSMA Expressing Tumors or Cells

In some aspects, the presently disclosed subject matter provides a method for imaging one or more prostate-specific membrane antigen (PSMA) tumors or cells, the method comprising contacting the one or more tumors or cells with an effective amount of a compound of formula (I) and making an image, wherein X of the compound of formula (I) is $^{124}$I and the imaging comprises positron emission tomography (PET).

D. One-Pot, Multi-Step Synthesis Method

In some embodiments, the presently disclosed subject matter provides a one-pot, multi-step synthesis method for preparing a radiotherapeutic compound of formula (Ia):

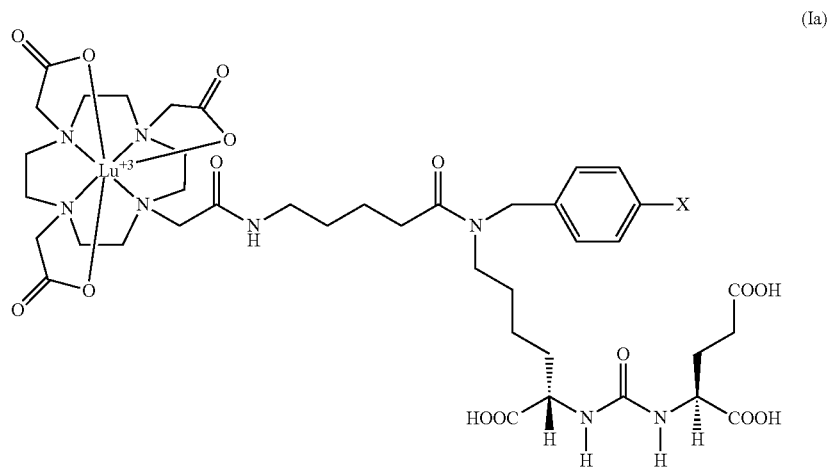

(Ia)

wherein X is a radiohalide, the method comprising:

(a) providing a precursor compound of formula (Ia'):

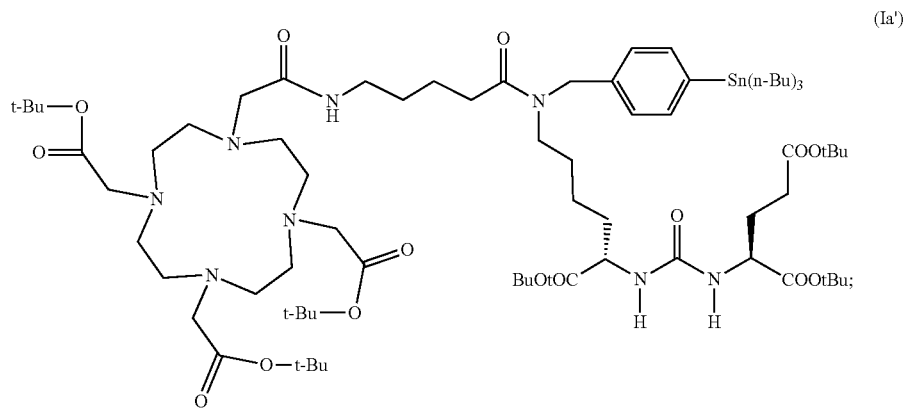

(Ia')

(b) contacting the precursor compound of formula (Ia') with solution comprising a radiohalide and N-chlorosuccinimide, followed by the addition of glacial acetic acid to form a radiohalogenated precursor compound of formula (Ia"):

(Ia'')

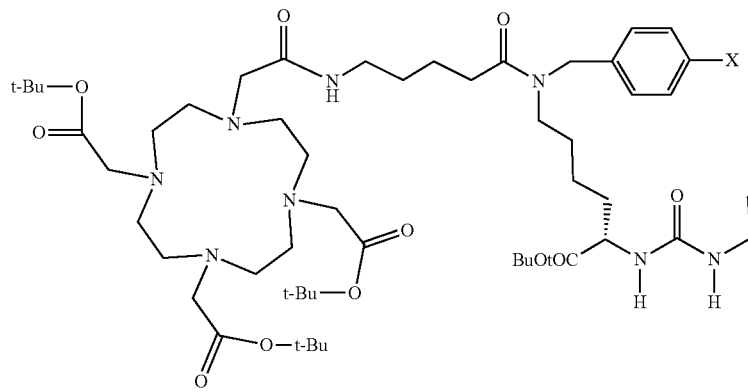

(c) contacting the radiohalogenated precursor compound of formula (Ia'') with trifluoroacetic acid to form a radiohalogenated compound of formula (Ia'''):

(Ia''')

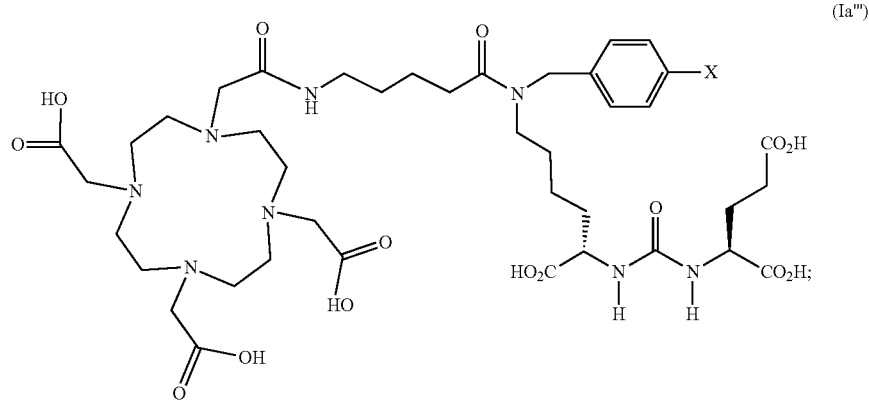

(d) contacting the radiohalogenated compound of formula (Ia''') with NaOAc and Lu(NO$_3$)$_3$ to form a radiotherapeutic compound of formula (Ia).

In some embodiments, the one-pot, multi-step synthesis method further comprises quenching step (d) with ethylenediaminetetraacetic acid (EDTA). In other embodiments, the one-pot, multi-step synthesis method further comprises purifying the radiotherapeutic compound of formula (Ia) by radio-high-performance liquid chromatography (HPLC).

In certain embodiments of the one-pot, multi-step synthesis method, the radiohalide is selected from the group consisting of $^{125}$I, $^{123}$I, $^{131}$I, $^{124}$I, $^{211}$At, $^{77}$Br, and $^{80m}$Br. In yet more certain embodiments of the one-pot, multi-step synthesis method, the radiohalide is iodine-125 ($^{125}$I) or astatine-211 ($^{211}$At).

E. Pharmaceutical Composition Comprising Compounds of Formula (I)

In another aspect, the present disclosure provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein.

When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include parenteral delivery, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries, which facilitate processing of the active compounds into preparations which can be used pharmaceutically.

In certain embodiments, the presently disclosed subject matter provides a kit for treating one or more PSMA expressing tumors or cells, the kit comprising a compound of formula (I). In yet more certain embodiments, the kit further comprises a blocking agent.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position.

The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)— $CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively. Accordingly, "cycloalkylene" can include $C_3$-$C_6$ cycloalkylene, including $C_3$, $C_4$, $C_5$, and $C_6$ cycloalkylene, such as cyclopropylene, cyclobutylene, cyclopentylene, and cyclohexylene, each of which can be substituted or unsubstituted.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups that are limited to hydrocarbon groups are termed "homoalkyl."

More particularly, the term "alkenyl" as used herein refers to a monovalent group derived from a $C_{1-20}$, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$, inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

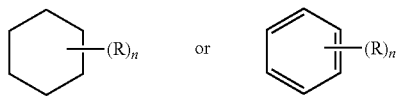

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

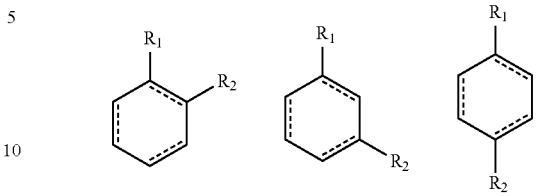

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R', —OC(O)R', —C(O)R', —CO$_2$R', —C(O)NR'R", —OC(O)NR'R", —NR"C(O)R', —NR'—C(O)NR"R', —NR"C(O)OR', —NR—C(NR'R")=NR', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR"R", —SR', —SiR"R'R', —OC(O)R', —C(O)R', —CO$_2$R', —C(O)NR'R", —OC(O)NR'R", —NR"C(O)R', —NR'—C(O)NR"R', —NR"C(O)OR', —NR—C(NR'R"R')=NR" ", —NR—C(NR'R")=NR'—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)$R.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example iodine-125 ($^{125}$I) or astatine-211 ($^{211}$At). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

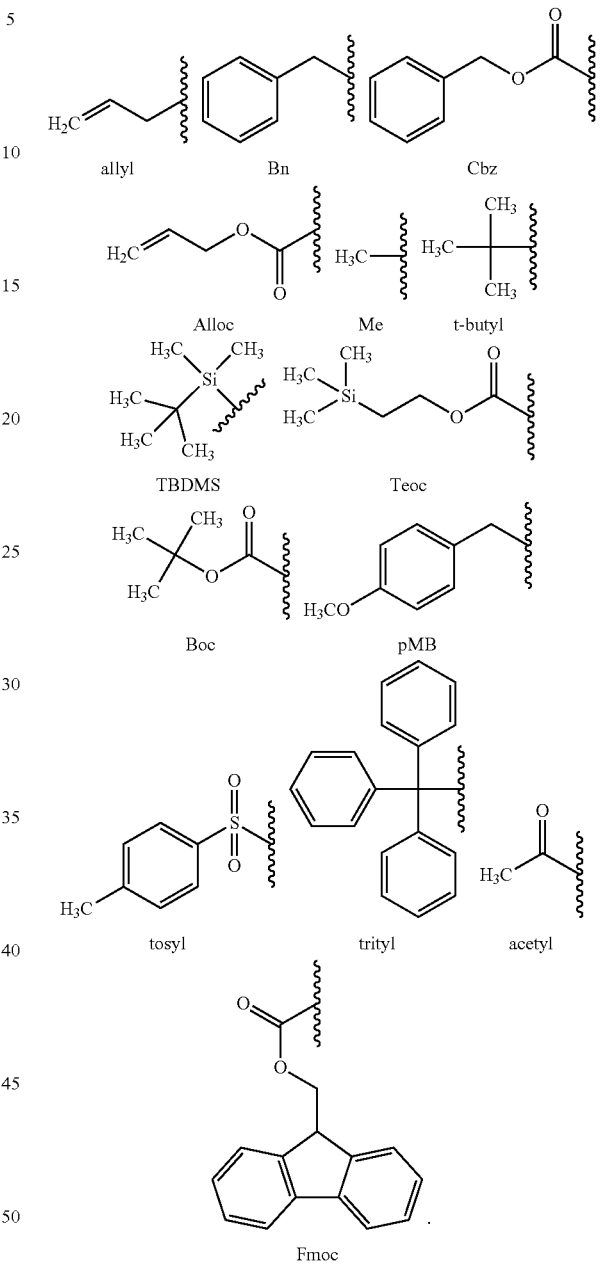

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

In the examples below the following terms are intended to have the following meaning: ACN: acetonitrile, DCM: Dichloromethane, DIPEA: N,N-Diisopropylethylamine, DMF: Dimethylformamide, HPLC: High Performance Liquid Chromatography, HRMS: High Resolution Mass Spectrometry, LRMS: Low Resolution Mass Spectrometry, NCS: N-Chlorosuccinimide, NHS: N-Hydroxysuccinimide, NMR: nuclear magnetic resonance, PMB: p-methoxybenzyl, RT: room temperature, TEA: Triethylamine, TFA: Trifluoroacetic acid, and TSTU: O—(N-Succinimidyl)-N,N,N', N'-tetramethyluronium tetrafluoroborate.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Overview

In a representative example, I-125 and At-211 labeled DOTA urea compound VK-02-90 demonstrated high specific PSMA positive tumor uptake in mice. Renal uptake at 1 hour is high, but clears much more rapidly than the radiohalogenated ureas. In addition, radioactivity in the stomach is very low, indicating that [$^{211}$At]VK-02-90 is stable in-vivo unlike the previous At-211 labeled ureas and almost all At-211 labeled small molecules. The lutetium complex of [$^{125}$I/$^{211}$At]VK-02-90 exhibits much lower initial uptake (1 h) in the kidneys and lacrimal glands compared to its non-lutetium complex version.

In contrast, [$^{125}$I]VK03-03, which has the [$^{125}$I]iodophenyl moiety within the linking moiety, also has high and prolonged tumor uptake, but, unlike [$^{125}$I/$^{211}$At]VK-02-90, radioactivity in the kidneys does not clear over time. [$^{125}$I] VK03-03 also has slower clearance from the lacrimal gland than [$^{125}$I/$^{211}$At]VK-02-90. The lutetium complex of [$^{125}$I] VK03-03 exhibits high and prolonged tumor uptake and does provide a modest clearance from the kidneys and lacrimal gland, but not to the extent seen with the lutetium complex of [$^{125}$I/$^{211}$At]VK-02-90.

This comparison of VK-02-90 and VK03-03 illustrates how changing the structure of the non-pharmacophore portion of the agent, in this case the linker between the DOTA and lysine-glutamate urea, can affect the uptake and retention of the PSMA targeted tracer in normal tissues.

Co-injection of a small amount (0.25-0.5 nmole) of non-radioactive-urea or -DOTA urea with [$^{125}$I/$^{211}$At]VK-02-90-Lu further reduces the uptake of radioactivity in the kidneys and lacrimal glands, which are problematic normal organs for radiopharmaceutical therapy. Taken together, I-125 and At-211 labeled DOTA urea compound VK-02-90-Lu administered with a small amount of non-radioactive PSMA inhibitor produces a biodistribution in mice that is very favorable for PSMA targeted radiopharmaceutical therapy (RPT) and represents a major step forward in developing an RPT agent for prostate cancer. When translated to patients it may provide an effective alpha radiotherapy for prostate cancer that eliminates or greatly reduces the side effects of RPT with alpha emitters, namely renal toxicity and dry mouth.

Example 2

Synthesis of Non-Radioactive VK-02-90 and VK-02-90-Lu and Radiohalogenation Precursor VK-02-85

Provided immediately herein below is a synthesis scheme for representative compounds VK-02-90, VK-02-90-Lu, and VK-02-85.

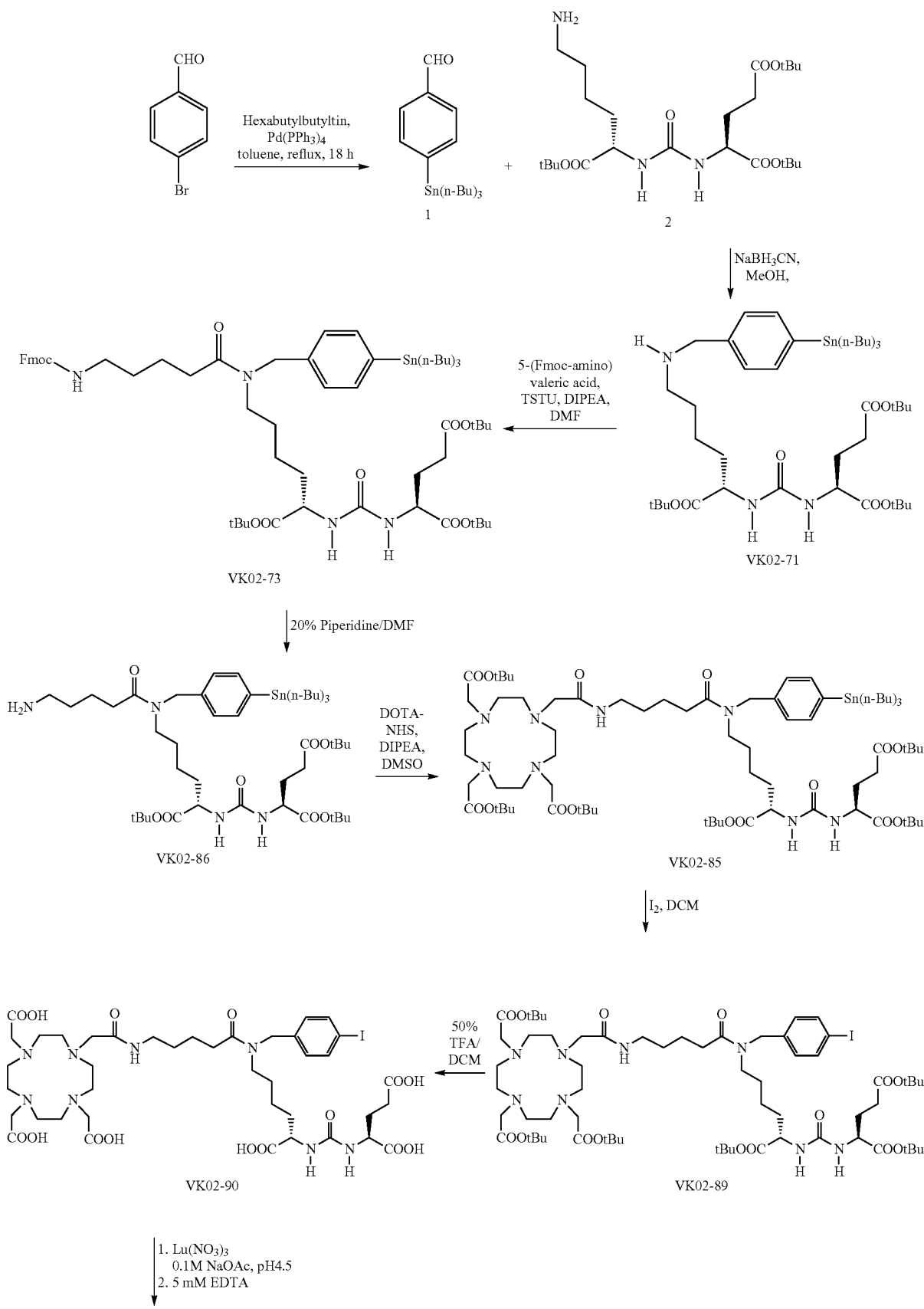

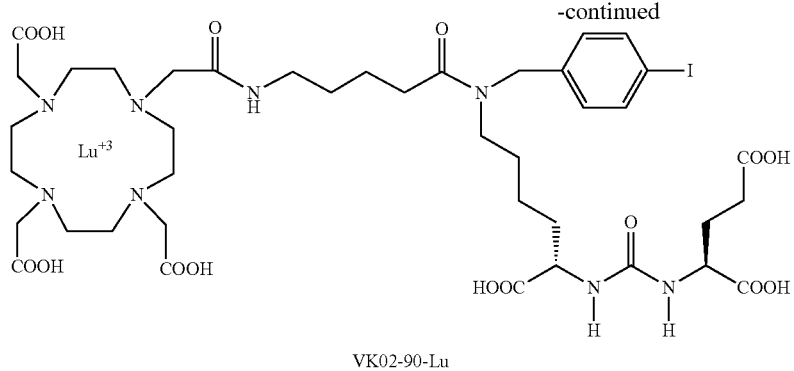

VK02-90-Lu 4-(Tributylstannyl)benzaldehyde (1) prepared as reported in Sessler, J. L., Wang, B., Harriman, A., Photoinduced energy transfer in associated, but noncovalently-linked photosynthetic model systems, JACS, 117, 704-714 (1995).

Di-tert-butyl (((S)-1-(tert-butoxy)-1-oxo-6-((4-(tributylstannyl)benzyl)amino)hexan-2-yl)carbamoyl)-L-glutamate (VK02-71): 4-(Tributylstannyl)benzaldehyde solution (0.500 g, 1.26 mmol, in 5 mL MeOH) was added dropwise to a stirred solution of urea (2) (0.614 g, 1.26 mmol) in MeOH (5 mL) at 0-5° C. under an inert atmosphere. The reaction mixture was stirred at RT for 1 h and then treated with sodium cyanoborohydride (0.318 g, 5.05 mmol). The mixture was stirred overnight at RT and concentrated in vacuum. Purification by flash column chromatography eluting with 40-50% EtOAc/Hexanes provided 0.537 g (49%) of oily material. $^1$H NMR (500 MHz, CDCl$_3$) δ ppm 7.48 (d, J=10.0 Hz, 2H), 7.36 (d, J=5.0 Hz, 2H), 5.92 (m, 1H), 5.73 (m, 1H), 4.26-4.23 (m, 1H), 4.07-4.00 (m, 2H), 2.87-2.84 (m, 2H), 2.29 (t, J=5.0 Hz, 2H), 1.91-1.87 (m, 1H), 1.80-1.78 (m, 1H), 1.72-1.70 (m, 2H), 1.59-1.55 (m, 1H), 1.53-1.49 (m, 5H), 1.45-1.41 (m, 27H), 1.34-1.26 (m, 7H), 1.25-1.22 (m, 3H), 1.05-1.02 (m, 6H), 0.86 (t, J=5.0 Hz, 9H); $^{13}$C NMR (125 MHz, CDCl$_3$) δ ppm 173.4, 172.5, 172.4, 172.2, 157.8, 143.9, 137.2, 137.0, 129.2, 82.6, 81.8, 80.6, 53.8, 53.5, 53.1, 51.9, 46.9, 31.7, 31.6, 29.7, 29.0, 28.1, 28.0, 27.3, 26.9, 26.1, 22.9, 13.7, 9.6. ESMS m/z: 868.4 (M+H)$^+$.

Tri-tert-butyl (15S,19S)-1-(9H-fluoren-9-yl)-3,9,17-trioxo-10-(4-(tributylstannyl)benzyl)-2-oxa-4,10,16,18-tetraazahenicosane-15,19,21-tricarboxylate (VK02-73): A mixture of 5-(Fmoc-amino)valeric acid (0.019 g, 0.06 mmol), TSTU (0.017 g, 0.06 mmol) and DIPEA (0.015 g, 0.11 mmol) were stirred in DMF (1 mL) at RT for 1 h. Amine (VK02-71, 0.05 g, 0.06 mmol) was added dropwise after dilution with DMF (1 mL). The reaction mixture was stirred for 4 h, concentrated and purified by flash column chromatography eluting with 40-50% EtOAc/Hexanes provided 0.537 g (47%) of oily material. $^1$H NMR (500 MHz, CDCl$_3$) δ ppm 7.76 (d, J=10.0 Hz, 3H), 7.60 (d, J=5.0 Hz, 3H), 7.40 (m, 4H), 7.31 (m, 4H), 4.99 (bs, 1H), 4.40 (m, 3H), 4.21 (m, 1H), 3.23 (q, J=5.0 Hz, 3H), 2.83 (m, 5H), 2.66-2.63 (m, 2H), 2.36-2.29 (m, 1H), 1.89-1.81 (m, 1H), 1.80-1.75 (m, 4H), 1.65-1.62 (m, 4H), 1.55-1.52 (m, 4H), 1.45-1.42 (m, 14H), 1.36-1.23 (m, 20H), 1.11-1.01 (m, 4H), 0.97 (d, J=5.0 Hz, 1H), 0.90-0.86 (m, 11H); $^{13}$C NMR (125 MHz, CDCl$_3$) δ ppm 169.2, 168.4, 156.5, 144.0, 141.3, 136.9, 127.7, 127.0, 125.1, 119.9, 66.5, 47.3, 40.3, 34.7, 31.6, 30.9, 29.7, 29.1, 28.1, 28.0, 27.4, 27.3, 25.6, 25.3, 22.7, 21.8, 18.8, 14.2, 13.7, 11.5, 9.6. ESMS m/z: 1208 (M−H+Na)$^+$.

Di-tert-butyl (((S)-6-(5-amino-N-(4-(tributylstannyl)benzyl)pentanamido)-1-(tert-butoxy)-1-oxohexan-2-yl)carbamoyl)-L-glutamate (VK02-86): A solution of 20% piperidine/DMF (2.5 mL) was added to VK02-73 (0.317 g, 0.27 mmol) and stirred at RT for 2.5 h. The reaction mixture was concentrated and purified by flash chromatography eluting with 10% MeOH/CH$_2$Cl$_2$/NH$_4$OH, lyophilized to provide 0.190 g (74%) of oily product. $^1$H NMR (500 MHz, CDCl$_3$) δ ppm 7.44 (d, J=5.0 Hz, 1H), 7.38 (d, J=5.0 Hz, 1H), 7.14 (d, J=5.0 Hz, 1H), 7.08 (d, J=5.0 Hz, 1H), 6.25 (m, 1H), 6.14-6.11 (m, 1H), 4.61-4.49 (m, 1H), 4.48-4.44 (m, 1H), 4.32-4.27 (m, 2H), 3.54-3.50 (m, 1H), 3.41 (m, 1H), 3.29-3.18 (m, 2H), 3.06-3.03 (m, 2H), 2.68 (m, 1H), 2.49-2.36 (m, 2H), 2.35-2.30 (m, 3H), 2.06-2.04 (m, 1H), 1.87-1.73 (m, 8H), 1.60-1.49 (m, 7H), 1.43-1.42 (m, 27H), 1.35-1.27 (m, 8H), 1.05-1.00 (m, 6H), 0.87 (t, J=10.0 Hz, 9H); $^{13}$C NMR (125 MHz, CDCl$_3$) δ ppm 173.9, 173.0, 172.8, 172.7, 157.5, 157.3, 141.3, 140.7, 137.0, 136.7, 136.2, 127.5, 125.8, 81.9, 81.8, 81.4, 80.6, 53.6, 52.9, 50.6, 47.8, 46.6, 45.1, 40.5, 32.7, 31.8, 29.7, 29.2, 29.1, 28.1, 27.4, 27.2, 26.9, 22.5, 21.9, 13.7, 9.6. ESMS m/z: 967.3 (M+H)$^+$.

Tri-tert-butyl (14S,18S)-2,8,16-trioxo-9-(4-(tributylstannyl)benzyl)-1-(4,7,10-tris(2-(tert-butoxy)-2-oxoethyl)-1,4,7,10-tetraazacyclododecan-1-yl)-3,9,15,17-tetraazaicosane-14,18,20-tricarboxylate (VK02-85): A reaction mixture of DOTA-NHS-ester (0.028 g, 0.03 mmol), VK02-86 (0.030 g, 0.03 mmol) and DIPEA (0.040 g, 0.31 mmol) were stirred in DMSO (1 mL) at RT for 3 h. The reaction mixture was concentrated and purified by flash chromatography eluting with 1.5% MeOH/CH$_2$Cl$_2$ to provide 0.024 g (51%) of oily product. $^1$H NMR (500 MHz, CDCl$_3$) δ ppm 7.40 (d, J=5.0 Hz, 1H), 7.35 (d, J=10.0 Hz, 1H), 7.11 (d, J=10.0 Hz, 1H), 7.07 (d, J=10.0 Hz, 1H), 6.56-6.52 (m, 1H), 6.15 (bs, 1H), 5.59 (d, J=10.0 Hz, 1H), 5.42 (d, J=5.0 Hz, 1H), 4.50 (d, J=10.0 Hz, 2H), 4.30-4.21 (m, 2H), 3.72-3.64 (m, 1H), 3.35-3.30 (m, 3H), 3.22-3.12 (m, 5H), 2.84 (m, 6H), 2.39 (m, 2H), 2.33-2.25 (m, 6H), 2.04-2.01 (m, 3H), 1.85 (m, 1H), 1.69-1.58 (m, 4H), 1.57-1.47 (m, 10H), 1.44-1.38 (m, 59H), 1.34-1.26 (m, 9H), 1.03-0.98 (m, 6H), 0.85 (t, J=10.0 Hz, 9H); $^{13}$C NMR (125 MHz, CDCl$_3$) δ ppm 173.5, 173.1, 172.9, 172.5, 172.4, 172.1, 171.4, 171.3, 169.7, 157.1, 157.0, 141.1, 140.5, 137.5, 136.9, 136.6, 136.5, 127.4, 125.8, 82.2, 81.9, 81.8, 81.7, 81.6, 56.0, 55.7, 53.2, 53.1, 52.9, 50.9, 48.1, 46.9, 45.5, 39.2, 39.1, 32.8, 32.6, 31.8, 31.7, 30.9, 29.1, 28.1, 28.0, 27.9, 27.8, 27.4, 26.6, 25.6, 22.6, 22.5, 22.4, 13.7, 9.6. ESMS m/z: 1518.8 (M−H)$^+$.

Tri-tert-butyl (14S,18S)-9-(4-iodobenzyl)-2,8,16-trioxo-1-(4,7,10-tris(2-(tert-butoxy)-2-oxoethyl)-1,4,7,10-tetraazacyclododecan-1-yl)-3,9,15,17-tetraazaicosane-14,18,20-tricarboxylate (VK02-89): Iodine (0.012 g) was added to a solution of VK02-85 (0.049 g, 0.032 mmol) in CH$_2$Cl$_2$ (2 mL) and stirred for 2 h at RT. The reaction mixture was washed with 10% aqueous Na$_2$S$_2$O$_5$ solution, dried, concentrated and purified by flash chromatography eluting with 1.5% MeOH/CH$_2$Cl$_2$ to provide 0.029 g (66%) of yellowish oily product. $^1$H NMR (500 MHz, DMSO-d6) δ ppm 7.65 (d, J=10.0 Hz, 1H), 7.60 (d, J=10.0 Hz, 1H), 6.97 (d, J=10.0 Hz, 1H), 6.92 (d, J=5.0 Hz, 1H), 6.54 (m, 1H), 5.22 (d, J=5.0 Hz, 1H), 4.50 (m, 2H), 4.32-4.25 (m, 2H), 3.47 (m, 1H), 3.33-3.30 (m, 3H), 3.22-3.15 (m, 4H), 2.86 (m, 6H), 2.65-2.52 (m, 3H), 2.42-2.40 (m, 2H), 2.33-2.24 (m, 5H), 2.07-2.04 (m, 3H), 1.86 (m, 3H), 1.70-1.56 (m, 10H), 1.46-1.42 (m, 48H), 1.37-1.20 (m, 8H), 0.92 (t, J=5.0 Hz, 3H); $^{13}$C NMR (125 MHz, DMSO-d6) δ ppm 173.6, 173.1, 172.6, 172.5, 172.4, 172.3, 171.9, 171.4, 157.1, 137.9, 137.6, 131.0, 130.0, 128.3, 92.5, 81.9, 81.8, 81.7, 81.6, 56.0, 55.7, 53.5, 53.1, 52.9, 50.6, 47.9, 47.3, 45.8, 39.1, 32.8, 32.5, 32.3, 31.6, 30.9, 28.8, 28.6, 28.2, 28.11, 28.0, 27.9, 26.8, 22.5, 22.4, 13.6. ESMS m/z: 702.4 (M/2+Na)$^+$.

(14S,18S)-9-(4-Iodobenzyl)-2,8,16-trioxo-1-(4,7,10-tris(carboxymethyl)-1,4,7,10-tetraazacyclododecan-1-yl)-3,9,15,17-tetraazaicosane-14,18,20-tricarboxylic acid (VK02-90): A cold solution of 50% TFA/CH$_2$Cl$_2$ (2 mL) was added to VK02-89 (0.064 g, 0.05 mmol) and stirred at RT for 2 h. The reaction mixture was concentrated and purified by C-18 column chromatography eluting with 40-50% acetonitrile/water, lyophilized to provide 0.030 g (62%) of white solid product. $^1$H NMR (500 MHz, DMSO-d6) δ ppm 12.65 (bs, 1H), 8.46 (s, 1H), 7.69 (d, J=3.0 Hz, 2H), 7.01 (s, 2H), 6.33 (s, 2H), 4.47 (d, J=4.0 Hz, 2H), 4.08 (s, 5H), 3.88 (s, 3H), 3.09 (m, 15H), 2.37 (s, 2H), 2.24 (s, 3H), 1.91 (s, 1H), 1.71-1.62 (m, 2H), 1.44 (m, 9H), 1.23 (s, 2H); $^{13}$C NMR (125 MHz, DMSO-d6) δ ppm 174.5, 174.4, 174.1, 173.7, 171.9, 158.0, 157.3, 138.4, 137.4, 137.1, 129.9, 128.8, 118.2, 115.8, 92.9, 92.7, 54.7, 54.0, 52.7, 52.2, 52.1, 51.7, 50.6, 49.6, 48.2, 47.1, 46.7, 31.8, 31.4, 29.9, 28.4, 27.8, 27.5, 26.7, 22.5, 22.3, 22.2. ESMS m/z: 1021.2 (M+H)$^+$.

$^{175}$Lutetium (III) (14S,18S)-9-(4-Iodobenzyl)-2,8,16-trioxo-1-(4,7,10-tris(carboxymethyl)-1,4,7,10-tetraazacyclododecan-1-yl)-3,9,15,17-tetraazaicosane-14,18,20-tricarboxylic acid ([I$^{75}$Lu]VK02-90): 7.92 mg (0.008 µmol) VK02-90 was dissolved in 25 µL of DMSO and diluted with 0.2 M NH$_4$OAc (1 mL). A solution of 2.7 mg (0.008 µmol) of Lu(NO$_3$)$_3$·xH$_2$O (dissolved in 540 µL of 0.1 M HCl) was added and heated at 70-80° C. for 1 h on water bath. The product was purified by HPLC using Phenomenex, Luna 10×250 mm, 10µ gradient 20/80/0.1 to 90/10/0.1 MeCN/H$_2$O/TFA, 0-40 min, flow 15 mL/min. Product eluted at 4.8 min. HRESI-MS: calcd. for C$_{40}$H$_{58}$ILuN$_8$O$_{15}$ 1193.2547 [M+H]$^+$, found: 1193.2535.

Example 3

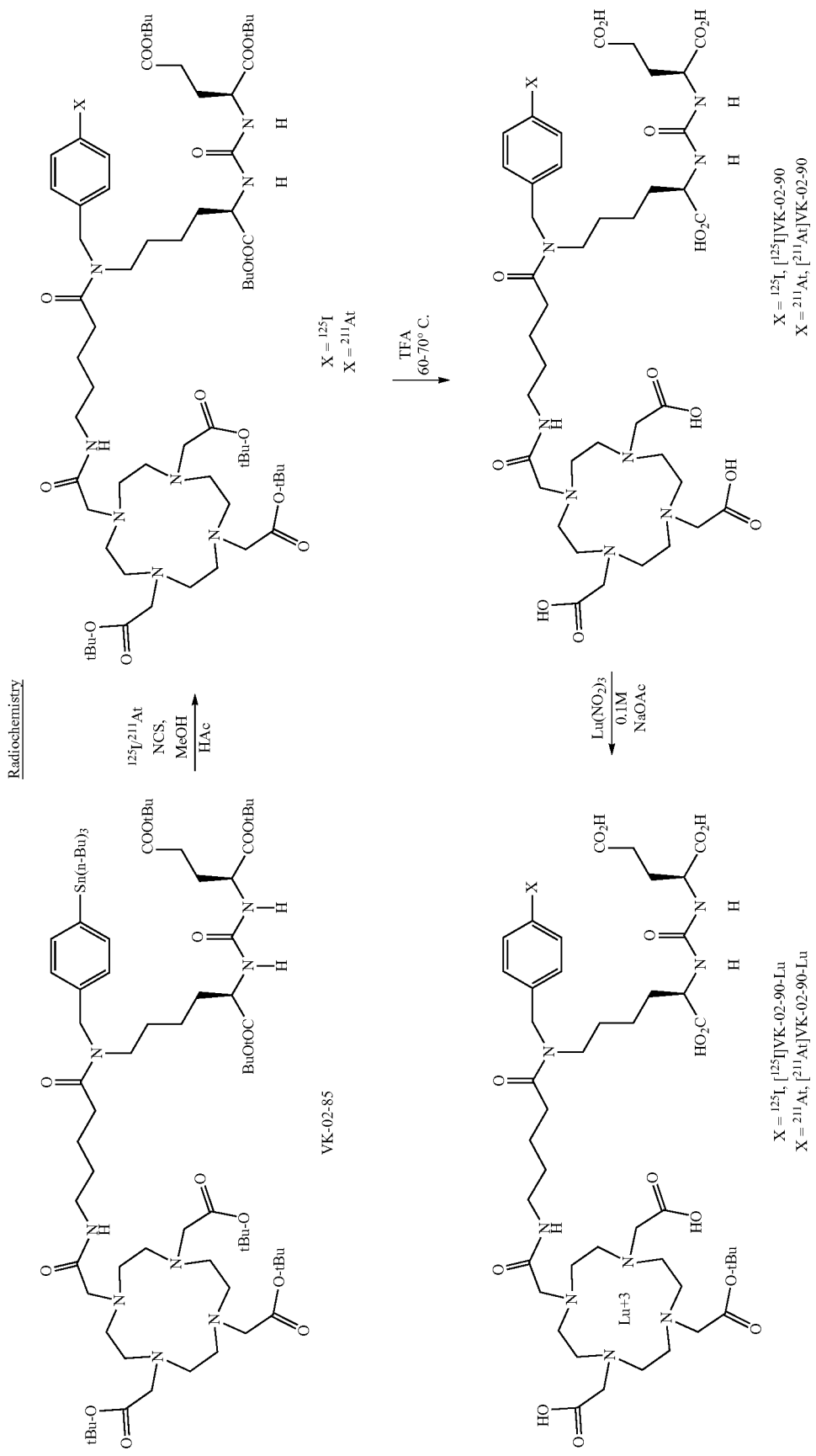

3.1 Multi-Step Synthesis with Isolation and Purification at Each Step.

3.1.1 Synthesis of [$^{125}$I]VK-02-90.

200 μg of VK-02-85 was dissolved in 100 μL methanol in a borosilicate screw capped vial. To this is added 2 μL glacial acetic acid and 7.2 mCi of a solution of Na$^{125}$I (Perkin Elmer), followed by 25 μL of a solution consisting of 1 mg N-chlorosuccinimide dissolved in 1 mL methanol. Vial was capped, shaken, and allowed to stand 20 min at room temperature. The reaction was concentrated to almost dryness under a stream of nitrogen with gentle heating. To this is added 200 μL trifluoroacetic acid and the vial was heated at 70° C. for 45 min, then concentrated under nitrogen, redissolved in 2 mL 20% acetonitrile in water, and purified by radio-HPLC (250×10 mm, 10 micron, Phenomenex Luna C18 column. Water/acetonitrile (both containing 0.1% TFA) Gradient elution. 15% acetonitrile to 50% acetonitrile over 30 min, flow 4 mL/m. [$^{125}$I]VK-02-90 (3.6 mCi) eluted@17 min. [$^{125}$I]VK-02-90 in the HPLC mobile phase was diluted to 20 mL with water and loaded onto a Waters Oasis HLB Sep-Pak, washed with 5 mL water, blown dry was a stream of nitrogen and eluted with 2 mL ethanol. This was concentrated under a stream of nitrogen.

3.1.2 Synthesis of [$^{125}$I]VK-02-90-Lu

The ethanol solution of [$^{125}$I]VK-02-90 was concentrated to almost dryness under a stream of nitrogen. To this is added 150 μL 0.1M NaOAc (pH 4.5), and 25 μL 5 mM Lu(NO$_3$)$_3$ in 0.1M HCl and mixed by micropipette. This solution was heated at 70° C. for 20 min, quenched with 100 μL 5 mM EDTA, diluted with 600 μL water and purified by radio-HPLC (250×10 mm, 10 micron, Phenomenex Luna C18 column. Water/acetonitrile (both containing 0.1% TFA) Gradient elution. 15% acetonitrile to 40% acetonitrile over 30 min, flow 4 mL/m. [$^{125}$I]VK-02-90-Lu (2.8 mCi) eluted at 21.5 min. Under these conditions, [$^{125}$I]VK-02-90 eluted at 20.5 min. Specific Activity of [$^{125}$I]VK-02-90-Lu was 2000 C$_i$/mmole. [$^{125}$I]VK-02-90-Lu in the HPLC mobile phase was diluted to 20 mL with water and loaded onto a Waters Oasis HLB Sep-Pak, washed with 5 mL water, blown dry with a stream of nitrogen and eluted with 2 mL ethanol. This was concentrated under a stream of nitrogen.

3.1.3 Synthesis of [$^{211}$At]VK-02-90

680 μg of VK-02-85 was dissolved in 190 μL of a solution consisting of 0.2 mg N-chlorosuccinimide/mL methanol and $^{211}$At (12.0 mCi) in a borosilicate screw capped vial. To this is added 2 μL glacial acetic acid. Vial was capped, shaken, and allow to stand 20 min at room temperature. The reaction was concentrated to almost dryness under a stream of nitrogen with gentle heating. To this is added 200 μL trifluoroacetic acid and the vial was heated at 70° C. for 45 min, then concentrated under nitrogen, redissolved in 2 mL 20% acetonitrile in water, and purified by radio-HPLC (250×10 mm, 10 micron, Phenomenex Luna C18 column. Water/acetonitrile (both containing 0.1% TFA) Gradient elution. 15% acetonitrile to 40% acetonitrile over 30 min, flow 4 mL/m. [$^{211}$At]VK-02-90 (1.5 mCi) eluted at 20 min. [$^{211}$At]VK-02-90 in the HPLC mobile phase was diluted to 20 mL with water and loaded onto a Waters Oasis HLB Sep-Pak, washed with 5 mL water, blown dry with a stream of nitrogen and eluted with 2 mL ethanol. This was concentrated under a stream of nitrogen.

3.1.4 Synthesis of [$^{211}$At]VK-02-90-Lu

The ethanol solution of [$^{211}$At]VK-02-90 was concentrated to almost dryness under a stream of nitrogen. To this is added 150 μL 0.1M NaOAc (pH 4.5), and 25 μL 5 mM Lu(NO$_3$)$_3$ in 0.1M HCl and mixed by micropipette. This solution was heated at 70° C. for 20 min, quenched with 100 μL 5 mM EDTA, diluted with 600 μL water and purified by radio-HPLC (250×10 mm, 10 micron, Phenomenex Luna C18 column. Water/acetonitrile (both containing 0.1% TFA) Gradient elution. 15% acetonitrile to 40% acetonitrile over 30 min, flow 4 mL/m. [$^{211}$At]VK-02-90-Lu (0.6 mCi) eluted at 19 min. [$^{211}$At]VK-02-90-Lu in the HPLC mobile phase was diluted to 20 mL with water and loaded onto a Waters Oasis HLB Sep-Pak, washed with 5 mL water, blown dry with a stream of nitrogen and eluted with 2 mL ethanol. This was concentrated under a stream of nitrogen.

3.2 Multi-Step One Pot Synthesis

3.2.1 Multi-Step One Pot Synthesis of [$^{125}$I]VK-02-90-Lu 100-160 μg of VK-02-85 was placed in a borosilicate screw capped vial. To this is added 200 μL of a solution consisting of 0.2 mg N-chlorosuccinimide/mL methanol. To this was added 1.3-1.7 mCi Na$^{125}$I (Perkin Elmer) dissolved in 20 μL water. Finally, 8 μL glacial acetic acid was added and the vial capped, shaken and allowed to stand 10 min at room temperature. The reaction was concentrated to almost dryness under a stream of nitrogen on a 57-60° C. heating bath. To this is added 200 μL 95/5 trifluoroacetic acid/water and the vial was heated at 60° C. for 30 min, then concentrated under nitrogen on a 57-60° C. heating bath. To this is added 200 μL 0.1M NaOAc (pH 4.5), and 30 μL 5 mM Lu(NO$_3$)$_3$ in 0.1M HCl and mixed by micropipette. This solution was heated at 60° C. for 20 min, quenched with 100 μL 5 mM EDTA, diluted with 600 μL water and purified by radio-HPLC (250×4.6 mm, 10 micron, Phenomenex Luna C18 column. Water/acetonitrile (both containing 0.1% TFA) Gradient elution. 15% acetonitrile to 40% acetonitrile over 30 min, flow 1 mL/m. [$^{125}$I]VK-02-90-Lu elutes at 22.5 min. [$^{125}$I]VK-02-90-Lu in the HPLC mobile phase was diluted to 20 mL with water and loaded onto a Waters Oasis HLB light Sep-Pak, washed with 5 mL water, blown dry with a stream of nitrogen, and eluted with 0.5 mL ethanol.

3.2.2 Multi-Step One Pot Synthesis of [$^{211}$At]VK-02-90-Lu

200 μg of VK-02-85 was placed in a borosilicate screw capped vial. To this was added $^{211}$At in 200 μL of a solution consisting of 0.2 mg N-chlorosuccinimide/mL methanol. To this was added 8 μL glacial acetic acid and the vial capped, shaken and allowed to stand 10 min at room temperature. The reaction was concentrated to dryness under a stream of nitrogen on a 60° C. heating bath. To this is added 200 μL 95/5 trifluoroacetic acid/water and the vial was heated at 60° C. for 30 min, then concentrated under nitrogen on a 60° C. heating bath. To this is added 200 μL 0.1M NaOAc (pH 4.5), and 30 μL 5 mM Lu(NO$_3$)$_3$ in 0.1M HCl and mixed by micropipette. This solution was heated at 60° C. for 20 min, quenched with 100 μL 5 mM EDTA, diluted with 600 μL water and purified by radio-HPLC (250×4.6 mm, 10 micron, XTerra C18 column. Water/acetonitrile (both containing 0.1% TFA) Gradient elution. 15% acetonitrile to 40% acetonitrile over 30 min, flow 1 mL/m. [$^{211}$At]VK-02-90-Lu elutes at 16.5-18 min. [$^{211}$At]VK-02-90-Lu in the HPLC mobile phase was diluted to 20 mL with water and loaded onto a Waters Oasis HLB light Sep-Pak, washed with 5 mL water, blown dry with a stream of nitrogen, and eluted with 0.5 mL ethanol.

TABLE 1

| Labeling method | Age of At-211 | Product and Non-decay corrected yield |
|---|---|---|
| A | NA | [$^{125}$I]VK-02-90-Lu 39% |
| B | NA | [$^{125}$I]VK-02-90-Lu 50-63% |
| A | Fresh | [$^{211}$At]VK-02-90-Lu 9% |
| A | 18 hour post-production | [$^{211}$At]VK-02-90-Lu 5% |
| B | Fresh | [$^{211}$At]VK-02-90-Lu 23% |
| B | 18 hour post-production | [$^{211}$At]VK-02-90-Lu 15% |

Method A: HPLC purification and isolation of both [$^{125}$I/$^{211}$At]VK-02-90 and [$^{125}$I/$^{211}$At]VK-02-90-Lu
Method B: Multi-step-single pot, HPLC purification of [$^{125}$I/$^{211}$At]VK-02-90-Lu only.

Example 4

Biodistribution Studies [$^{125}$I]VK-02-90-Lu and [$^{211}$At]VK-02-90-Lu

Referring now to Table 2, comparative biodistribution of [$^{125}$I]VK-02-90 and [$^{125}$I]VK-02-90-Lu demonstrates the faster clearance of [$^{125}$I]VK-02-90-Lu from the spleen, salivary glands, lacrimal glands and kidneys.

TABLE 2

Biodistribution (% injected dose/g) of I-125 Labeled PSMA inhibitors in 6-8 week old athymic mice (25 g) bearing both PSMA + PC3-PIP and PSMA − PC3-flu flank xenografts without cold blocking agent.

| | [$^{125}$I]VK-02-90 | | | [$^{125}$I] VK-02-90-Lu | | |
|---|---|---|---|---|---|---|
| Organs | 1 H | 4 H | 24 H | 1 H | 4 H | 24 H |
| blood | 1.1 ± 0.3 | 0.2 ± 0.03 | 0.02 ± 0.01 | 1.2 ± 0.4 | 0.06 ± 0.06 | 0.1 ± 0.01 |
| stomach | 1.1 ± 0.3 | 0.4 ± 0.2 | 0.05 ± 0.03 | 0.7 ± 0.4 | 0.1 ± 0.1 | 0.04 ± 0.01 |
| spleen | 40.2 ± 16.4 | 4.7 ± 1.2 | 0.7 ± 0.4 | 7.4 ± 2.6 | 0.6 ± 0.2 | 0.1 ± 0.06 |
| thyroid | NC | NC | NC | NC | NC | NC |
| salivary glands | 5.1 ± 3.4 | 0.7 ± 0.2 | 0.3 ± 0.3 | 1.0 ± 0.3 | 0.1 ± 0.05 | 0.03 ± 0.01 |
| Lacrimal glands | 17.4 ± 6.0 | 1.9 ± 0.45 | 0.5 ± 0.2 | 4.1 ± 1.3 | 0.3 ± 0.1 | 0.06 ± 0.03 |
| kidneys | 194 ± 25 | 162 ± 36 | 30.6 ± 14.0 | 180 ± 36 | 18.2 ± 4.9 | 3.3 ± 1.1 |
| Pip (tumor) | 58 ± 14 | 38 ± 13 | 51 ± 7 | 51 ± 8.5 | 27.8 ± 17 | 24.0 ± 6.2 |
| Flu (tumor) | 1.4 ± 0.6 | 0.3 ± 0.06 | 0.04 ± 0.02 | 0.9 ± 0.3 | 0.3 ± 0.5 | 0.03 ± 0.01 |

NC—Not Collected

Tables 3, 4, and 5 are comparisons of cold blocking agents YC—I-27 and VK-02-90 at doses of 0.5, 1.0, and 5 nmoles on the biodistribution (% injected dose/g) of [$^{125}$I]VK-02-90-Lu in 6-8 week old athymic mice bearing both PSMA+ PC3-PIP and PSMA-PC3-flu flank xenografts at 1, 4, and 24 hours, respectively.

TABLE 3

1-hour Biodistribution

| | Blocker | | | | | | |
|---|---|---|---|---|---|---|---|
| Organ | None | YC-I-27 0.5 nmole | YC-I-27 1.0 nmole | YC-I-27 5 nmole | VK-02-90 0.5 nmole | VK-02-90 1.0 nmole | VK-02-90 5.0 nmole |
| Blood | 1.1 ± 0.1 | 1.1 ± 0.1 | 1.0 ± 0.1 | 1.1 ± 0.2 | 0.4 ± 0.1 | 0.4 ± 0.1 | 0.5 ± 0.1 |
| Stomach | 1.7 ± 0.3 | 1.8 ± 0.2 | 1.8 ± 0.3 | 2.2 ± 0.7 | 0.2 ± 0.1 | 0.2 ± 0.04 | 0.2 ± 0.06 |
| Spleen | 4.3 ± 0.9 | 0.8 ± 0.2 | 0.6 ± 0.1 | 0.7 ± 0.1 | 1.1 ± 0.4 | 1.1 ± 0.4 | 0.7 ± 0.2 |
| Salivary glands | 2.3 ± 0.5 | 3.2 ± 0.7 | 2.9 ± 0.4 | 5.1 ± 1.7 | 0.2 ± 0.03 | 0.2 ± 0.06 | 0.3 ± 0.1 |

TABLE 3-continued

1-hour Biodistribution

| | | Blocker | | | | | |
|---|---|---|---|---|---|---|---|
| Organ | None | YC-I-27 0.5 nmole | YC-I-27 1.0 nmole | YC-I-27 5 nmole | VK-02-90 0.5 nmole | VK-02-90 1.0 nmole | VK-02-90 5.0 nmole |
| Lacrimal Glands | 2.1 ± 0.9 | 0.5 ± 0.1 | 0.6 ± 0.05 | 1.1 ± 0.6 | 0.4 ± 0.1 | 0.4 ± 0.1 | 0.4 ± 0.03 |
| Kidneys | 129 ± 15 | 4.2 ± 1.3 | 2.4 ± 0.8 | 2.3 ± 0.7 | 9.9 ± 2.5 | 6.5 ± 0.9 | 4.2 ± 0.5 |
| PIP tumor | 26.0 ± 3.0 | 41.8 ± 4.2 | 29.1 ± 2.4 | 20.1 ± 2.8 | 36.7 ± 6.8 | 35.1 ± 9.0 | 23.5 ± 4.3 |
| Flu tumor | 1.0 ± 0.2 | 1.0 ± 0.3 | 0.8 ± 0.2 | 0.8 ± 0.2 | 0.6 ± 0.3 | 0.5 ± 0.1 | 0.9 ± 0.3 |

TABLE 4

4-hr Biodistribution

| | | Blocker | | | | | |
|---|---|---|---|---|---|---|---|
| Organ | None | YC-I-27 0.5 nmole | YC-I-27 1.0 nmole | YC-I-27 5 nmole | 9VK-02-0 0.5 nmole | 9VK-02-0 1.0 nmole | VK-02-90 5.0 nmole |
| Blood | 0.3 ± 0.2 | 0.4 ± 0.06 | 0.4 ± 0.05 | 0.4 ± 0.1 | 0.02 ± 0.01 | 0.2 ± 0.01 | 0 |
| Stomach | 0.8 ± 0.5 | 1.3 ± 0.2 | 1.2 ± 0.2 | 1.6 ± 0.4 | 0.06 ± 0.01 | 0.1 ± 0.03 | 0.1 ± 0.04 |
| Spleen | 0.6 ± 0.2 | 0.25 ± 0.07 | 0.2 ± 0.04 | 0.3 ± 0.06 | 0.2 ± 0.1 | 0.2 ± 0.1 | 0.15 ± 0.08 |
| Salivary glands | 1.8 ± 0.2 | 3.3 ± 0.8 | 3.2 ± 0.7 | 5.0 ± 1.4 | 0.08 ± 0.04 | 0.1 ± 0.02 | 0.05 ± 0.02 |
| Lacrimal glands | 0.4 ± 0.2 | 0.2 ± 0.02 | 0.2 ± 0.03 | 0.5 ± 0.5 | 0.1 ± 0.03 | 0.1 ± 0.05 | 0.1 ± 0.1 |
| Kidneys | 9.5 ± 2.5 | 0.9 ± 0.1 | 0.6 ± 0.03 | 0.7 ± 0.1 | 2.1 ± 0.7 | 1.4 ± 0.4 | 0.9 ± 0.3 |
| PIP tumor | 27.4 ± 7.5 | 24.0 ± 3.2 | 23.8 ± 1.1 | 14.3 ± 5.0 | 24.8 ± 2.0 | 27.1 ± 3.6 | 18.8 ± 2.0 |
| Flu tumor | 0.25 ± 0.1 | 0.3 ± 0.1 | 0.3 ± 0.1 | 0.3 ± 0.1 | 0.10.02 | 0.1 ± 0.03 | 0.1 ± 0.01 |

TABLE 5

24-hour Biodistribution

| | | Blocker | | | | | |
|---|---|---|---|---|---|---|---|
| Organ | None | YC-I-27 0.5 nmole | YC-I-27 1.0 nmole | YC-I-27 5 nmole | VK-02-90 0.5 nmole | VK-02-90 1.0 nmole | VK-02-90 5.0 nmole |
| Blood | 0 | 0.03 ± 0.03 | 0.02 ± 0.01 | 0.02 ± 0.01 | 0.1 ± 0.01 | 0 | 0 |
| Stomach | 0.1 ± 0.04 | 0.1 ± 0.1 | 0.08 ± 0.03 | 0.07 ± 0.1 | 0.04 ± 0.04 | 0.03 ± 0.02 | 0.04 ± 0.03 |
| Spleen | 0.1 ± 0.05 | 0.02 ± 0.02 | 0.04 ± 0.02 | 0.01 ± 0.03 | 0.04 ± 0.01 | 0 | 0.01 ± 0.03 |
| Salivary glands | 0.2 ± 0.08 | 0.6 ± 0.5 | 0.4 ± 0.2 | 0.4 ± 0.1 | 0.02 ± 0.01 | 0 | 0.01 ± 0.01 |
| Lacrimal glands | 0.05 ± 0.04 | 0.03 ± 0.04 | 0.02 ± 0.02 | 0.01 ± 0.02 | 0.03 ± 0.02 | 0 | 0.01 ± 0.03 |
| Kidneys | 1.3 ± 0.7 | 0.1 ± 0.05 | 0.08 ± 0.05 | 0.05 ± 0.02 | 0.5 ± 0.2 | 0.4 ± 0.1 | 0.2 ± 0.2 |
| PIP tumor | 18.0 ± 6.0 | 13.4 ± 3.8 | 12.6 ± 3.1 | 6.6 ± 3.2 | 16.3 ± 4.2 | 18.3 ± 3.7 | 10.6 ± 3.2 |
| Flu tumor | 0.05 ± 0.01 | 0.04 ± 0.02 | 0.03 ± 0.01 | 0.03 ± 0.01 | 0.04 ± 0.01 | 0.03 ± 0.01 | 0.02 ± 0.01 |

Referring now to Table 6, Table 7, and Table 8 are the biodistributions of At-211 labeled compounds showing the lower kidney and stomach uptake of [$^{211}$At]VK-02-90-Lu compared to other At-211 labeled PSMA inhibitors reported in International PCT Patent Application Publication No. WO2017070482 A2, to Pomper et al., published Apr. 27, 2017, at 1 hour, 2-4 hours, and 21-24 hours, respectively.

TABLE 6

1 Hour Biodistribution (% injected dose/g) of At-211 Labeled PSMA inhibitors in 6-8 week old athymic mice (25 g) bearing both PSMA + PC3-PIP and PSMA − PC3-flu flank xenografts with and without cold blocking agent.

| | Agent | | | | | | | |
|---|---|---|---|---|---|---|---|---|
| Organ | YC-I-27 (no blocker) | YC-IV-11 (no blocker) | PSMA-620 (no blocker) | PSMA-904 (no blocker) | HS-549 (no blocker) | [Lu]VK-02-90 (no blocker) | [Lu]VK-02-90 + (0.25 nmole YC-I-27) | [Lu]VK-02-90 (0.5 nmole YC-I-27) |
| blood | 1.7 ± 0.3 | 1.8 ± 1.6 | 1.0 ± 0.2 | 0.6 ± 0.3 | 5.5 ± 0.8 | 0.8 ± 0.2 | 0.6 ± 0.04 | 0.5 ± 0.1 |
| stomach | 10.1 ± 1.7 | 5.4 ± 0.6 | 2.0 ± 0.4 | 1.6 ± 0.6 | 7.1 ± 2.2 | 0.4 ± 0.1 | 0.4 ± 0.2 | 0.4 ± 0.2 |
| spleen | 29 ± 10 | 8.9 ± 1.3 | 17.1 ± 3.7 | 9.5 ± 2.8 | 8.8 ± 2.1 | 2.5 ± 0.9 | 0.5 ± 0.4 | 0.3 ± 0.4 |
| thyroid | 3.7 ± 1.1 | 1.6 ± 0.2 | 0.8 ± 0.2 | 0.5 ± 0.2 | 3.2 ± 0.6 | NC | NC | NC |
| salivary gland | NC | NC | NC | NC | NC | 0.5 ± 0.2 | 0.4 ± 0.15 | 0.4 ± 0.15 |
| lacrimal gland | NC | NC | NC | NC | NC | 0.8 ± 0.9 | 0.1 ± 0.4 | 0 |
| kidney | 71 ± 12 | 135 ± 19 | 103 ± 24 | 87 ± 15 | 46.7 ± 8.2 | 90 ± 43 | 5.0 ± 1.6 | 2.2 ± 0.6 |
| PIP (tumor) | 17.9 ± 3.0 | 13.8 ± 5.1 | 16.5 ± 4.8 | 22.7 ± 5.4 | 43.2 ± 9.8 | 30.6 ± 4.8 | 34.2 ± 7.8 | 25.4 ± 4.4 |
| Flu (tumor) | 2.2 ± 0.4 | 1.4 ± 0.2 | 1.1 ± 0.2 | 0.8 ± 0.3 | 3.5 ± 0.5 | 0.4 ± 0.2 | 0.4 ± 0.1 | 0.4 ± 0.1 |

TABLE 7

2-4 Hour Biodistribution (% injected dose/g) of At-211 Labeled PSMA inhibitors in 6-8 week old athymic mice (25 g) bearing both PSMA + PC3-PIP and PSMA − PC3-flu flank xenografts with and without cold blocking agent.

| | Agent | | | | | | | |
|---|---|---|---|---|---|---|---|---|
| Organ | YC-I-27[a] (no blocker) | YC-IV-11[a] (no blocker) | PSMA-620[a] (no blocker) | PSMA-904[b] (no blocker) | HS-549[b] (no blocker) | [Lu]VK-02-90[a] (no blocker) | [Lu]VK-02-90[a] + (0.25 nmole YC-I-27) | [Lu]VK-02-90[a] (0.5 nmole YC-I-27) |
| Blood | 1.0 ± 0.1 | 0.6 ± 0.1 | 0.3 ± 0.1 | 0.4 ± 0.03 | 2.9 ± 0.4 | 0.1 ± 0.03 | 0.2 ± 0.1 | 0.2 ± 0.1 |
| Stomach | 13.3 ± 3.1 | 8.0 ± 2.3 | 2.9 ± 0.6 | 2.9 ± 0.7 | 14.3 ± 3.2 | 0.3 ± 0.2 | 0.5 ± 0.3 | 0.4 ± 0.05 |
| Spleen | 20.3 ± 3.6 | 5.8 ± 1.9 | 3.6 ± 2.4 | 4.3 ± 2.0 | 6.1 ± 1.6 | 0 | 0.1 ± 0.5 | 0.8 ± 0.5 |
| Thy roid | 3.8 ± 1.2 | 2.0 ± 0.3 | 0.8 ± 0.2 | 1.0 ± 0.3 | 4.1 ± 2.0 | NC | NC | NC |
| Salivary gland | NC | NC | NC | NC | NC | 0.2 ± 0.1 | 0.2 ± 0.1 | 0.3 ± 0.2 |
| Lacrimal gland | NC | NC | NC | NC | NC | 0.3 ± 1.1 | 0.4 ± 0.4 | 0 |
| Kidney | 60 ± 12 | 70 ± 43 | 78 ± 39 | 88 ± 11 | 40 ± 15 | 2.1 ± 0.6 | 1.4 ± 0.3 | 0.7 ± 0.1 |
| PIP (tumor) | 18.3 ± 2.9 | 13.3 ± 4.2 | 18.3 ± 4.3 | 21.1 ± 6.2 | 42 ± 7.2 | 17.1 ± 5.2 | 27.8 ± 8.7 | 18.7 ± 5.4 |
| Flu (tumor) | 1.5 ± 0.2 | 1.1 ± 0.2 | 0.6 ± 0.2 | 0.5 ± 0.05 | 2.8 ± 0.6 | 0.1 ± 0.1 | 0.1 ± 0.2 | 0.1 ± 0.04 |

[a]4 H;

[b]2 H;

NC—not collected

TABLE 8

21-24 Hour Biodistribution (% injected dose/g) of At-211 Labeled PSMA inhibitors in 6-8 week old athymic mice (25 g) bearing both PSMA + PC3-PIP and PSMA − PC3-flu flank xenografts with and without cold blocking agent.

| Organ | YC-I-27[a] (no blocker) | YC-IV-11[a] (no blocker) | PSMA-620[a] (no blocker) | PSMA-904[a] (no blocker) | HS-549[a] (no blocker) | [Lu]VK-02-90[b] (no blocker) | [Lu]VK-02-90[b] + (0.25 nmole YC-I-27) | [Lu]VK-02-90[b] (0.5 nmole YC-I-27) |
|---|---|---|---|---|---|---|---|---|
| blood | 0.5 ± 0.05 | 0.3 ± 0.1 | 0.1 ± 0.1 | 0.5 ± 0.1 | 0.9 ± 0.2 | 0 | 0.3 ± 1.0 | 0.03 ± 0.3 |
| stomach | 9.4 ± 3.0 | 4.3 ± 1.2 | 1.9 ± 1.0 | 9.4 ± 2.2 | 12.6 ± 6.2 | 0 | 0.3 ± 0.4 | 0.4 ± 0.7 |
| spleen | 8.0 ± 2.0 | 4.2 ± 0.8 | 0.9 ± 0.4 | 2.1 ± 0.7 | 2.3 ± 0.7 | 0 | 0 | 2.5 ± 4.3 |
| thyroid | 6.5 ± 2.0 | 2.2 ± 1.0 | 0.9 ± 0.1 | 3.7 ± 1.4 | 3.8 ± 0.6 | NC | NC | NC |
| salivary gland | NC | NC | NC | NC | NC | 0 | 0 | 0 |
| lacrimal gland | NC | NC | NC | NC | NC | 0 | 0 | 0 |
| kidney | 57.4 ± 7.4 | 5.4 ± 15 | 7.5 ± 1.8 | 4.4 ± 3.5 | 2.6 ± 0.8 | 0.02 ± 0.2 | 0.3 ± 0.4 | 0.4 ± 0.5 |
| PIP (tumor) | 31.1 ± 9.8 | 12.3 ± 3.0 | 13.6 ± 3.3 | 12.1 ± 5.0 | 10.6 ± 9.9 | 9.5 ± 1.0 | 15.3 ± 8.0 | 17.5 ± 7.9 |
| Flu (tumor) | 1.2 ± 0.2 | 0.6 ± 0.2 | 0.2 ± 0.1 | 0.8 ± 0.2 | 1.1 ± 0.3 | 0 | 0.04 ± 0.2 | 0.2 ± 0.3 |

[a]21 H;
[b]24 H;
NC—not collected

TABLE 9

Biodistribution Data for [125I]VK-03-03 and [125I]VK-03-03-Lu in Mice.

| | [125I]VK-03-03 | | [125I]VK-03-03-Lu | |
|---|---|---|---|---|
| | 1 H | 24 H | 4 H | 24 H |
| blood | 1.6 ± 0.26 | 0.49 ± 0.08 | 0.09 ± 0.02 | 0.46 ± 0.15 | 0.09 ± 0.03 |
| heart | 1.6 ± 0.5 | 0.9 ± 0.03 | 0.17 ± 0.08 | 0.57 ± 0.27 | 0.09 ± 0.04 |
| lung | 4.5 ± 0.6 | 2.3 ± 0.3 | 0.58 ± 0.2 | 1.56 ± 0.5 | 0.15 ± 0.05 |
| liver | 0.9 ± 0.15 | 0.4 ± 0.2 | 0.09 ± 0.02 | 0.23 ± 0.05 | 0.06 ± 0.02 |
| spleen | 70.0 ± 20.4 | 37.4 ± 8.9 | 4.9 ± 2.7 | 15.7 ± 7.0 | 1.2 ± 0.4 |
| pancreas | 1.8 ± 0.27 | 1.5 ± 0.05 | 0.26 ± 0.07 | 0.82 ± 0.73 | 0.04 ± 0.02 |
| stomach | 1.0 ± 0.12 | 0.95 ± 0.7 | 0.18 ± 0.06 | 0.41 ± 0.18 | 0.07 ± 0.02 |
| small intestine | 0.76 ± 0.13 | 0.37 ± 0.08 | 0.08 ± 0.03 | 0.2 ± 0.05 | 0.03 ± 0.02 |
| large intestine | 1.2 ± 0.06 | 0.58 ± 0.19 | 0.11 ± 0.06 | 0.26 ± 0.11 | 0.04 ± 0.005 |
| fat | 3.2 ± 0.7 | 4.1 ± 1.5 | 0.37 ± 0.28 | 1.5 ± 0.9 | 0.62 ± 0.8 |
| muscle | 1.0 ± 0.2 | 0.64 ± 0.22 | 0.1 ± 0.05 | 0.32 ± 0.18 | 0.03 ± 0.02 |
| salivary gland | 5.0 ± 0.86 | 3.5 ± 0.4 | 0.6 ± 0.16 | 1.4 ± 0.46 | 0.15 ± 0.06 |
| lacrimal gland | 25.4 ± 4.1 | 15.8 ± 4.9 | 2.6 ± 0.76 | 5.5 ± 2.5 | 0.7 ± 0.3 |
| kidney | 132 ± 18.5 | 165 ± 14.4 | 141 ± 18.3 | 199 ± 34 | 50.4 ± 25.9 |
| bladder | 5.0 ± 2.9 | 2.4 ± 0.5 | 1.6 ± 0.75 | 5.5 ± 6.0 | 2.8 ± 1.4 |
| Flu (tumor) | 2.0 ± 0.7 | 1.2 ± 0.28 | 0.2 ± 0.09 | 0.75 ± 0.27 | 0.09 ± 0.02 |
| PiP (tumor) | 44.7 ± 12.2 | 57.0 ± 15.9 | 54.1 ± 6.3 | 60.1 ± 21.0 | 53.0 ± 8.0 |

Example 4
Synthesis of Non-radioactive VK03-03 and Radiohalogenation Precursor VK03-01
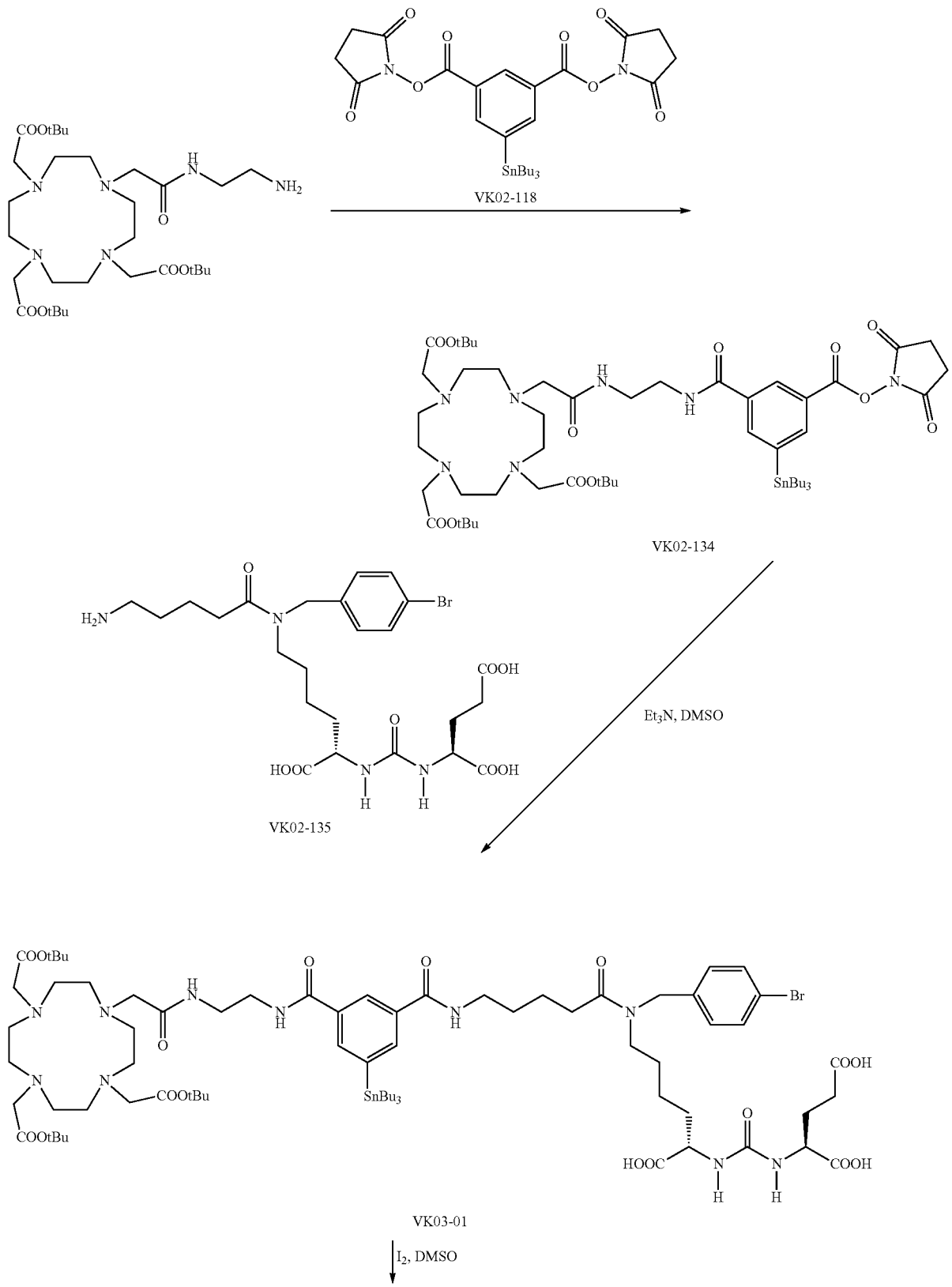

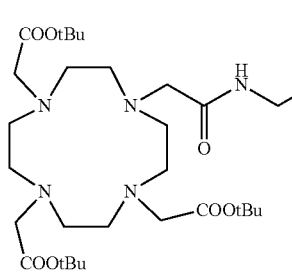
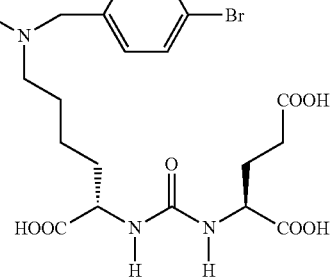

VK03-02

↓ 50% TFA/DCM

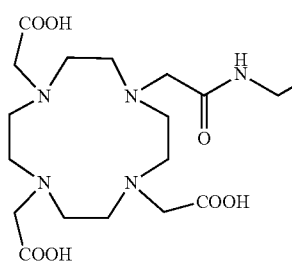
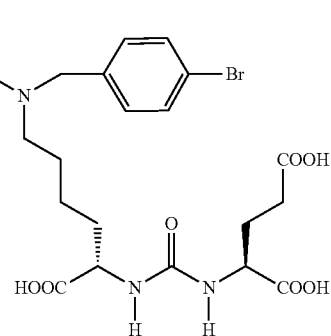

VK03-03

Tri-tert-butyl 2,2',2''-(10-(2-((2-(3-(((2,5-dioxopyrrolidin-1-yl)oxy)carbonyl)-5-(tributylstannyl)benzamido)ethyl) amino)-2-oxoethyl)-1,4,7,10-tetraazacyclododecane-1,4,7-triyl)triacetate (VK02-134): A reaction mixture of commercial 2-aminoethyl-mono-amide-DOTA-tris(t-Bu ester) DOTA-amine (0.051 g, 0.07 mmol), bis(2,5-dioxopyrrolidin-1-yl) 5-(tributylstannyl)isophthalate (VK02-118) (0.048 g, 0.07 mmol) (G. Vaidyanathan et al. Biorg & Med. Chem. 20(24) 6929-6939, 2012) and Et₃N (0.022 g, 0.22 mmol) were stirred in DMSO at RT for 2 h. The reaction mixture was concentrated and purified by flash column chromatography eluting with 2% MeOH/CH₂Cl₂ to produce 0.032 g (38%) of oily material. $^1$H NMR (500 MHz, CDCl₃) δ ppm 8.71 (s, 1H), 8.42 (s, 1H), 8.32 (s, 1H), 3.45 (s, 2H), 2.91 (bs, 4H), 2.61 (s, 47H, peak merged with DMSO), 1.63 (m, 1H), 1.54-1.44 (m, 7H), 1.33-1.23 (m, 12H), 1.11 (t, J=5.0 Hz, 6H), 0.87 (t, J=5.0 Hz, 9H). ESMS m/z: 1150.8 (M+H)⁺.

(13S,17S)-8-(4-Bromobenzyl)-1,7,15-trioxo-1-(3-(tributylstannyl)-5-((2-(2-(4,7,10-tris(2-(tert-butoxy)-2-oxoethyl)-1,4,7,10-tetraazacyclododecan-1-yl)acetamido)ethyl)carbamoyl)phenyl)-2,8,14,16-tetraazanonadecane-13,17,19-tricarboxylic acid (VK03-01): A reaction mixture of VK02-134 (0.270 g, 0.23 mmol), VK02-135 (0.138 g, 0.23 mmol) and Et₃N (0.071 g, 0.70 mmol) were stirred in DMSO at RT for 2 h. The reaction mixture was concentrated and purified by C-18 column chromatography eluting with 70-100% acetonitrile/water, lyophilized to provide 0.095 g (25%) of white solid product. $^1$H NMR (500 MHz, CDCl₃) δ ppm 8.69-8.55 (m, 3H), 8.31 (s, 1H), 8.00-7.94 (m, 2H), 7.60-7.56 (m, 1H), 7.50-7.48 (m, 1H), 7.41 (bs, 2H), 7.17-7.14 (m, 1H), 6.36-6.29 (m, 1H), 4.46 (s, 1H), 4.19 (bs, 2H), 4.10 (m, 2H), 3.11 (m, 6H), 2.94 (m, 5H), 2.41 (m, 1H), 2.27 (m, 2H), 1.93 (m, 1H), 1.61-1.55 (m, 10H), 1.49 (s, 16H), 1.41 (s, 28H), 1.33-1.28 (m, 11H), 1.14 (t, J=5.0 Hz, 8H), 0.87 (t, J=5.0 Hz, 9H). ESMS m/z: 809.9 (M/2+H)⁺.

(13S,17S)-8-(4-Bromobenzyl)-1-(3-iodo-5-((2-(2-(4,7,10-tris(2-(tert-butoxy)-2-oxoethyl)-1,4,7,10-tetraazacyclododecan-1-yl)acetamido)ethyl)carbamoyl)phenyl)-1,7,15-trioxo-2,8,14,16-tetraazanonadecane-13,17,19-tricarboxylic acid (VK03-02): Iodine (0.012 g) was added to a solution of VK03-01 (0.050 g, 0.031 mmol) in CH₂Cl₂ (2 mL) and stirred for 2 h at RT. The reaction mixture was concentrated and purified by C-18 column chromatography eluting with 40-60% acetonitrile/water. The brown product was used as such for next step. ESMS m/z: 1457.8 (M−H)⁺.

(13S,17S)-8-(4-Bromobenzyl)-1-(3-iodo-5-((2-(2-(4,7,10-tris(carboxymethyl)-1,4,7,10-tetraazacyclododecan-1-yl)acetamido)ethyl)carbamoyl)phenyl)-1,7,15-trioxo-2,8,14,16-tetraazanonadecane-13,17,19-tricarboxylic acid (VK03-03): A chilled solution of 50% TFA/CH₂Cl₂ (2 mL) was added to VK03-02 (0.066 g, 0.04 mmol) and stirred at RT for 2 h. The reaction mixture was concentrated and purified by HPLC using C-18 column. $^1$H NMR (500 MHz, CD₃CN+D₂O) δ ppm 8.24-8.22 (m, 1H), 8.13-8.11 (m, 1H), 7.89 (m, 1H), 7.53 (m, 1H), 7.46-7.40 (m, 2H), 7.08-7.05 (m, 2H), 4.48 (s, 1H), 4.43 (s, 1H), 4.16-4.13 (m, 2H), 3.64 (bs, 7H), 3.44 (s, 3H), 3.31 (m, 4H), 3.24-3.14 (m, 10H), 2.41 (m, 1H), 2.34-2.29 (m, 3H), 1.83-1.79 (m, 2H), 1.67-1.42 (m, 9H), 1.38-1.36 (m, 5H), 1.23 (m, 4H). ESMS m/z: 1291.8 (M+H)⁺.

Example 5

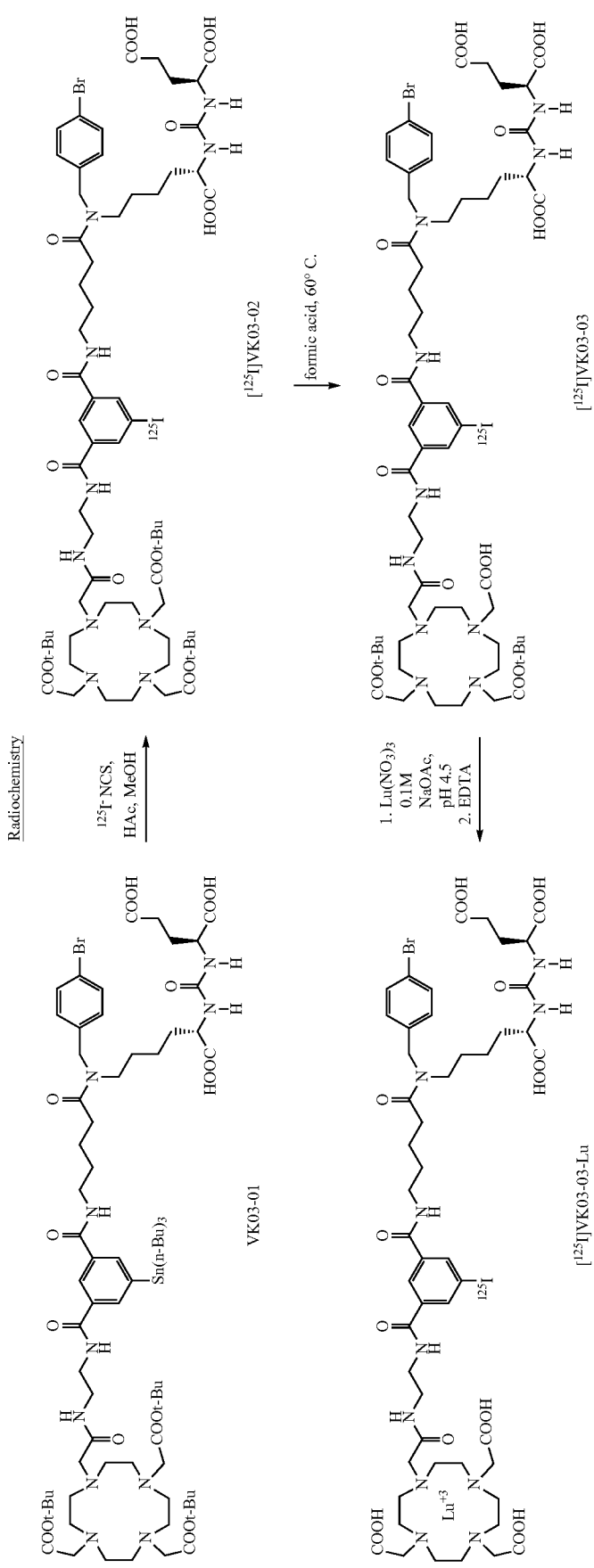

Multi-Step Synthesis with Isolation and Purification at Each Step.

Synthesis of [$^{125}$I]VK03-03.

200 μg of VK03-01 was dissolved in 100 μL methanol in a borosilicate screw capped vial. To this is added 2 μL glacial acetic acid and 7.0 mCi of a solution of Na$^{125}$I (Perkin Elmer), followed by 25 μL of a solution consisting of 1 mg N-chlorosuccinimide dissolved in 1 mL methanol. Vial was capped, shaken, and allowed to stand 20 min at room temperature. The reaction was concentrated to almost dryness under a stream of nitrogen with gentle heating. To this was added 200 μL concentrated formic acid and the vial was heated at 60° C. for 60 min, cooled, diluted to 1 mL with water, and purified by radio-HPLC (250×10 mm, 10 micron, Phenomenex Luna C18 column. Water/acetonitrile (both containing 0.1% TFA) Gradient elution. 15% acetonitrile to 50% acetonitrile over 30 min, flow 4 mL/m. [$^{125}$I]VK03-03 (1.0 mCi) eluted @ 21.5 min. [$^{125}$I]VK03-03 in the HPLC mobile phase was diluted to 20 mL with water and loaded onto a Waters Oasis HLB Sep-Pak, washed with 5 mL water, blown dry was a stream of nitrogen and eluted with 2 mL ethanol. This was concentrated under a stream of nitrogen.

Synthesis of [$^{125}$I]VK03-03-Lu

The ethanol solution of [$^{151}$1]VK03-03 (690 uCi) was concentrated to almost dryness under a stream of nitrogen. To this is added 150 μL 0.1M NaOAc (pH 4.5), and 25 μL 5 mM Lu(NO$_3$)$_3$ in 0.1M HCl and mixed by micropipette. This solution was heated at 60° C. for 20 min, quenched with 100 μL 5 mM EDTA, diluted with 600 μL water and purified by radio-HPLC (250×10 mm, 10 micron, Phenomenex Luna C18 column. Water/acetonitrile (both containing 0.1% TFA) Gradient elution. 15% acetonitrile to 50% acetonitrile over 30 min, flow 4 mL/m. [$^{125}$I]VK03-03-Lu (270 μCi) eluted at 22.5 min. Under these conditions, [$^{125}$I]VK03-03 eluted at 21.5 min. Specific Activity of [$^{125}$I]VK03-03-Lu was estimated to be 645Ci/mmole based on the standard curve for [$^{125}$I]VK03-03. [$^{125}$I]VK03-03-Lu in the HPLC mobile phase was diluted to 20 mL with water and loaded onto a Waters Oasis HLB Sep-Pak, washed with 5 mL water, blown dry with a stream of nitrogen and eluted with 2 mL ethanol. This was concentrated under a stream of nitrogen.

Example 6

Results

Radiolabeled small-molecule PSMA inhibitors are currently under clinical investigation as imaging and radiotherapeutic agents for prostate cancer (PC). Astatine-211 is a 7.2 h radiohalogen emitting short range, high linear energy transfer alpha particles well suited for treatment of PC micrometastases. $^{211}$At labeled PSMA binding agents known in the art suffered from high renal retention, resulting in radiation nephropathy, and deastatination in vivo. The presently disclosed subject matter provides strategies for addressing those problems using a DOTA containing $^{211}$At—or $^{125}$I-labeled PSMA agent, its nonradioactive Lu complex, and co-injection of a well-characterized competing PSMA ligand, DCIBzL (YC—I-27).

Radiosyntheses were done using a one-pot multistep reaction sequence consisting of a) radiohalogenation of 1 with $^{125}$I$^-$ or $^{211}$At in methanol containing N-chlorosuccinimide and acetic acid, b) concentration, c) acid hydrolysis to give [$^{125}$I/$^{211}$At]2, and d) metal complexation with non-radioactive Lu to give [$^{125}$I/$^{211}$At]3. Final compounds were purified by HPLC. Biodistribution was performed after i.v. bolus of 37 kBq (1 μCi) into athymic mice bearing both PSMA+ PC3-PIP and PSMA− PC3-flu flank xenografts with and without co-injection of 0.5 nmol DCIBzL (YC—I-27). Organs were harvested 1, 4, and 24 h post-injection (n=5 per time point).

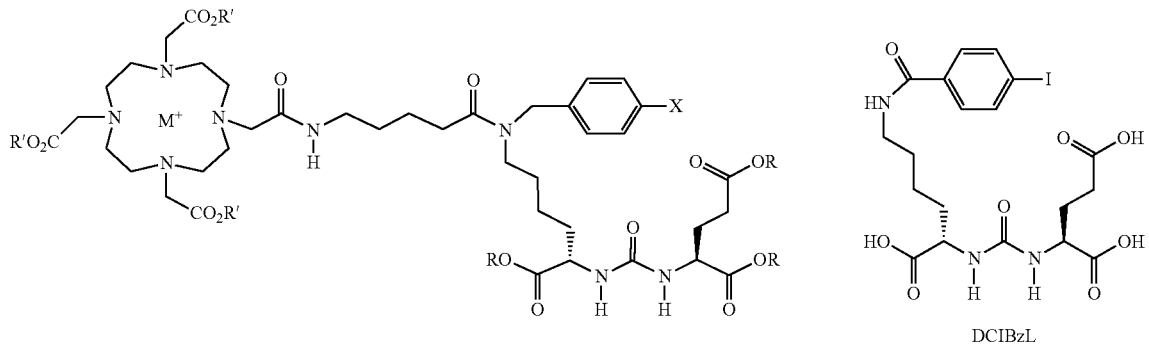

1. R = R' = t-Bu, X = Sn(n-Bu)$_3$, M$^+$ none
[$^{125}$I]2. R = R' = H, X = $^{125}$I, M$^+$ none
[$^{125}$I]3. R = R' = H, X = $^{125}$I, M$^+$ = Lu$^{+3}$
[$^{211}$At]2. R = R' = H, X = $^{211}$At, M$^+$ none
[$^{211}$At]3. R = R' = H, X = $^{211}$At, M$^+$ = Lu+3

Radiochemical yields (non-decay corrected) were 53-60% for [$^{125}$I]3 and 12-26% for [$^{211}$At]3. All agents had high uptake in PIP tumors (10-50% ID/g) with minimal uptake in flu tumors. Lutetium complexation ([$^{125}$I]3 compared to [$^{125}$I]2) reduced retention of radioactivity in potentially problematic tissues: a) kidneys (K) (4 h; 162±36 vs 18.2±4.9% ID/g; 24 h, 30.6±14.0 vs 3.3±1.1% ID/g); b) salivary glands (SG) at 1 h (5.1±3.4 vs 1.0±0.3% ID/g); and c) lacrimal glands (LG) at 1 h (17.4±6.0 vs 4.1±1.3% ID/g). Co-injection of DCIBzL with [$^{125}$I]3 or [$^{211}$At]3 further reduced retention in K, SG, and LG: [$^{125}$I]3 @1 h, K 4.2±1.3, SG 3.2±0.7, LG 0.5±0.1% ID/g; [$^{211}$At]3 @ 1 h, K 2.2±0.6, SG 0.4±0.15% ID/g, LG below detection, resulting in T/K ratios of 11, 27, and 44 @ 1, 4, and 24 h; and T/SG ratio of 64 @ 1 h for [$^{211}$At]3. Stomach uptake of [$^{125}$I]3 and [$^{211}$At]3 was low and comparable ([$^{125}$I]3, 1.8±0.2, 0.8±0.5, and 0.1±0.04% ID/g; [$^{211}$At]3, 0.4±0.2, 0.4±0.05, 0.4±0.7% ID/g @ 1, 4, and 24 h, respectively, suggesting negligible deastatination occurred in vivo.

By combining a lutetium loaded radiohalogenated agent with an appropriate competitive PSMA ligand, ([$^{211}$At]3 and DCIBzL), it was possible to obtain high (25.4±4.4% ID/g) and prolonged $^{211}$At uptake in PSMA+ PC3-PIP xenografts with low levels of activity in normal tissues including kidneys, salivary glands, and lacrimal glands, with no evidence of deastatination in vivo. These results represent a considerable improvement compared with previously described $^{211}$At-labeled PSMA inhibitors and further evaluation of the therapeutic potential of this promising combination strategy is warranted.

Example 7

PSMA-Targeted Alpha Therapeutic Agent with Fast Kidney Clearance 7.1 Overview. [$^{211}$At]DCIBzL exhibited high efficacy as a PSMA-targeted radiopharmaceutical therapy (RPT) agent in preclinical models of human prostate cancer (PC), but it caused renal failure due to its high uptake and long retention in kidney. See Kiess et al., 2016. To enhance the therapeutic index of the $^{211}$At-based PSMA-targeted agents, [$^{211}$At]VK-02-90-Lu was developed and previously shown to have rapid renal clearance while exhibiting persistent retention in PSMA+ tumors. Mease et al., 2018. This example demonstrates the efficacy and toxicity of [$^{211}$At]VK-02-90-Lu in experimental models of PC and in healthy immunocompetent mice, respectively.

7.2 Methods. Two murine models of human PC were generated, a subcutaneous (SC) model of PSMA+ PC3-PIP and PSMA− PC3-flu cells and a metastatic model of PSMA+ PC3ML/PSMA/fLuc in NOD/SCID/IL-2rγ_/_ (NSG) mice. Single intravenous injection of different doses (FIG. 3) was given to each animal and the tumor progression was monitored by measuring the SC tumor volume or by performing bioluminescence imaging for the metastatic model. CD-1 mice were injected with individual doses of 1.48 MBq (40 μCi), 0.74 MBq (20 μCi), and 0.244 MBq (6.6 μCi), and the animals were monitored for long-term toxicity.

7.3 Results. [$^{211}$At]VK-02-90-Lu showed a favorable SC tumor-specific uptake as the ratios of tumor/kidney, tumor/salivary gland, and tumor/lacrimal gland at 4 h post injection were 2.9, 14.8, and 62.1, respectively. These ratios further improved at 24 h to 14.1, 85.7, and 360.0. A dose-dependent response was observed in the PSMA+ PC3-PIP SC model, whereas there was no effect on the PSMA− PC3-flu model (FIG. 3A). There was also a dose-dependent therapeutic effect of [$^{211}$At]VK-02-90-Lu also was observed in the metastatic model (FIG. 3B). Lower doses were required for the SC model due to higher levels of PSMA within the cells than in the metastatic model. No CD-1 animals showed treatment-related toxicity up to 4 months after treatment measured by overall health status and urinalysis 7.4 Summary. [$^{211}$At]VK-02-90-Lu is a promising candidate PSMA-targeted RPT with a favorable therapeutic index.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Pomper M G, Zhang J, Kozikowski A P, Musachio J L. Imaging agents and methods of imaging NAALADase of PSMA. PCT Patent Application Publication No. WO 03/060523.

Pomper M G, Zhang J, Kozikowski A P, Musachio J L. Imaging agents and methods of imaging NAALADase of PSMA. U.S. Patent Application Publication No. 2004/0054190.

Pomper, M. Pomper, Martin Gilbert; Ray, Sangeeta; Mease, Ronnie C.; Foss, Catherine. Labeled inhibitors of prostate specific membrane antigen (PSMA), biological evaluation, and use as imaging agents. PCT Patent Application Publication No. WO 2009002529.

Pomper M G, Mease R C, Chen Y. Preparation of glutamic acid heterodimer prostate-specific membrane antigen PSMA binding agents for therapeutic and imaging use. PCT Patent Application Publication No. WO 2010014933.

Pomper, Martin G.; Mease, Ronnie C.; Ray, Sangeeta; Chen, Ying. PSMA− targeting compounds and uses thereof. PCT Patent Application Publication No. WO 2010108125.

Pomper, Martin G. Mease, Ronnie C., Ray, Sangeeta, Shallal, Hassan. Homomultivalent and heteromultivalent inhibitors of prostate specific membrane antigen (PSMA) and uses thereof. PCT Patent Application Publication No. WO 2013082338.

Babich J W, Zimmerman C N, Maresca K P. Heterodimers of glutamic acid. U.S. Patent Application Publication No. 2008/0193381.

Babich J W, Ziommerman C, Joyal J L, Lu G. Radiolabeled prostate specific membrane antigen inhibitors U.S. Patent Application Publication No. 2013/0034494.

Low P S, Chelvam V, Kim Y. PSMA binding ligand-linker conjugates and methods for using. PCT Patent Application Publication Nos. WO 2011/106639, WO 2010/045598, and WO 2009/026177.

Pomper M G, Mease R C, Chen Y, Ray S, Zalutsky M, Vaidyanathan G. Preparation of PSMA targeted radiohalogenated urea peptidomimetics for cancer therapy. PCT Patent Application Publication No. WO 2017070482.

Ray S, Pomper M G. Prostate-specific membrane antigen targeted high affinity agents for endoradiotherapy of prostate cancer. PCT Patent Application Publication No. WO 2017165473.

Kiess A P, Minn I, Vaidyanathan G, et al. (2S)-2-(3-(1-Carboxy-5-(4-211At-Astatobenzamido)Pentyl)Ureido)-Pentanedioic Acid for PSMA-Targeted alpha-Particle Radiopharmaceutical Therapy. *J Nucl Med.* 2016; 57:1569-1575.

Mease R, Kang C, Kumar V, et al. Small Molecule Radiohalogenated (125I/211At), DOTA Containing PSMA Inhibitors: Metal Complexation and Competing Inhibitor Improve Biodistribution in Mice. *Journal of Nuclear Medicine.* 2018; 59:537

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of the following formula:

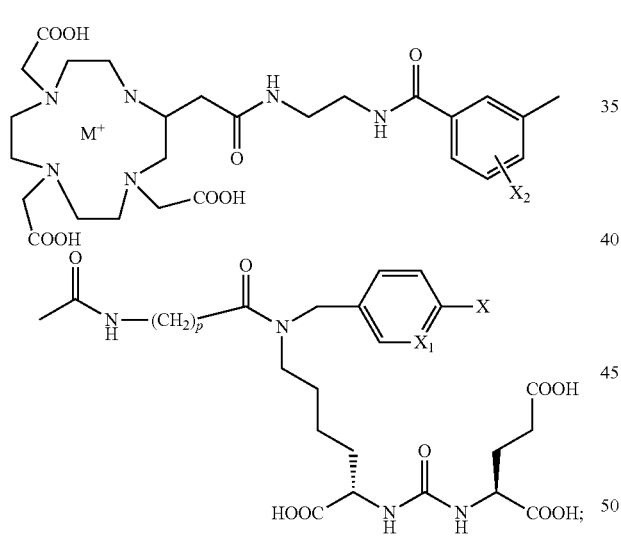

wherein:
- p is an integer selected from the group consisting of 1, 2, 3, 4, 5, and 6; and
- X is halogen;
- $X_1$ is —$CR^3$ or N, wherein $R^3$ is H or $C_1$-$C_4$ alkyl; and
- $X_2$ is selected from the group consisting of a radioisotope of iodine, a radioisotope of bromine, and a radioisotope of astatine; and
- wherein $M^+$ is a metal, which can be present or absent.

2. The compound of claim 1, wherein $M^+$ is a metal selected from the group consisting of: Y, Lu, Tc, Zr, In, Sm, Re, Cu, Pb, Ac, Bi, Al, Ga, Re, Ho and Sc, and radioisotopes thereof.

3. The compound of claim 1, wherein the compound of formula (I) is selected from the group consisting of:

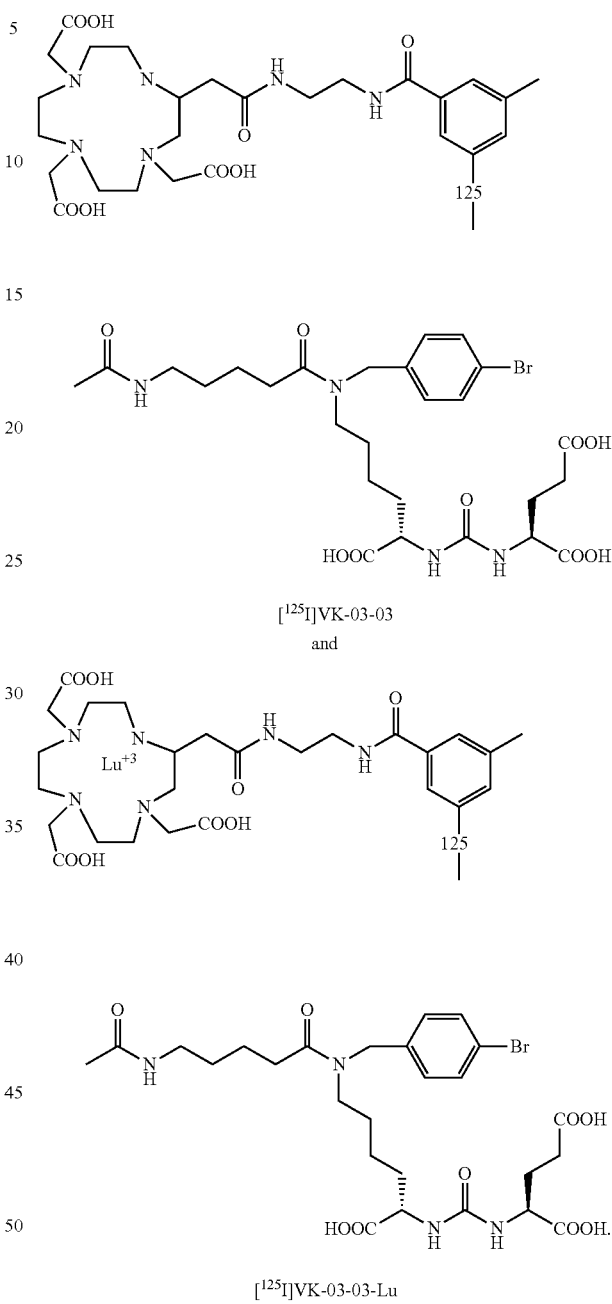

4. A method for treating one or more PSMA expressing tumors or cells, the method comprising administering or contacting the one or more PSMA expressing tumors or cells with an effective amount of a compound of claim 1.

5. The method of claim 4, wherein the one or more PSMA-expressing tumor or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

6. The method of claim 4, wherein the one or more PSMA-expressing tumor or cells is a prostate tumor or cell.

7. The method of claim 4, wherein the one or more PSMA-expressing tumor or cells is in vitro, in vivo, or ex vivo.

8. The method of claim 4, wherein the one or more PSMA-expressing tumor or cells is present in a subject.

9. The method of claim 8, wherein the subject is human.

10. The method of claim 4, wherein the method results in inhibition of tumor growth.

11. The method of claim 4, further comprising administering a blocking agent in combination with the compound of formula (I), wherein the blocking agent reduces accumulation of the compound of formula (I) in one or more PSMA expressing cells in an off-target organ.

12. The method of claim 11, wherein the off-target organ is selected from the group consisting of blood, stomach, spleen, thyroid gland, salivary gland, lacrimal gland, and kidney.

13. The method of claim 12, wherein the off-target organ is the kidney or salivary gland.

14. The method of claim 11, wherein the blocking agent comprises a PSMA-based blocking agent.

15. The method of claim 14, wherein the PSMA-based blocking agent is a compound of formula (I) that is not radiohalogenated, wherein the compound of formula (I) used as a blocking agent and the compound of formula (I) used as a therapeutic agent can be the same or different.

16. The method of claim 14, wherein the PSMA-based blocking agent is:

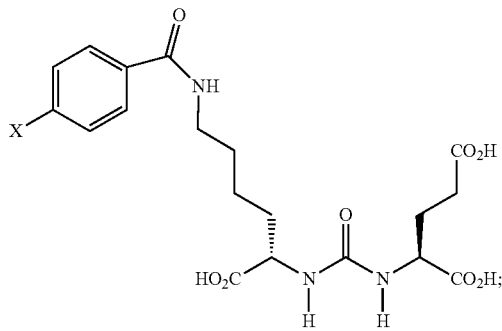

YC-I-27 wherein X is halogen.

17. A pharmaceutical composition comprising a compound of claim 1 and a pharmaceutically acceptable carrier.

18. A kit for treating on or more PSMA expressing tumors or cells, the kit comprising a compound of claim 1.

19. The kit of claim 18, further comprising a blocking agent.

20. The compound of claim 1, wherein $X_2$ is selected from the group consisting of $^{211}$At, $^{131}$I, $^{125}$I, $^{124}$I, $^{123}$I, $^{77}$Br, and $^{80m}$Br.

* * * * *

UNITED STATES PATENT AND TRADEMARK OFFICE
CERTIFICATE OF CORRECTION

PATENT NO. : 12,233,137 B1
APPLICATION NO. : 18/448682
DATED : February 25, 2025
INVENTOR(S) : Martin G. Pomper et al.

Page 1 of 1

It is certified that error appears in the above-identified patent and that said Letters Patent is hereby corrected as shown below:

In the Claims

Column 115, Claim 1, Line 33-52 should read:

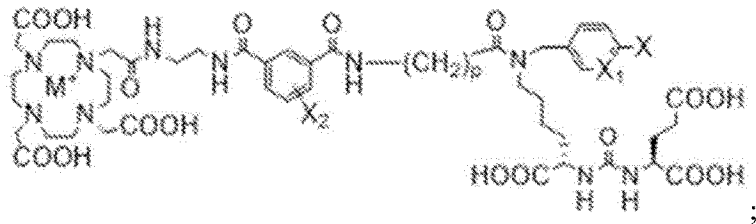
;

Column 116, Claim 3, Line 5-53 should read:

.

Signed and Sealed this
Eighth Day of April, 2025

Coke Morgan Stewart
*Acting Director of the United States Patent and Trademark Office*